(12) United States Patent
Heyes et al.

(10) Patent No.: US 10,077,232 B2
(45) Date of Patent: Sep. 18, 2018

(54) CYCLIC CATIONIC LIPIDS AND METHODS OF USE

(75) Inventors: James Heyes, Vancouver (CA); Mark Wood, Port Moody (CA); Alan Martin, Vancouver (CA)

(73) Assignee: ARBUTUS BIOPHARMA CORPORATION, Burnaby, BC (CA)

( * ) Notice: Subject to any disclaimer, the term of this patent is extended or adjusted under 35 U.S.C. 154(b) by 1565 days.

(21) Appl. No.: 13/696,999

(22) PCT Filed: May 12, 2011

(86) PCT No.: PCT/GB2011/000722
§ 371 (c)(1),
(2), (4) Date: Jan. 17, 2013

(87) PCT Pub. No.: WO2011/141704
PCT Pub. Date: Nov. 17, 2011

(65) Prior Publication Data
US 2013/0116307 A1    May 9, 2013

Related U.S. Application Data

(60) Provisional application No. 61/334,096, filed on May 12, 2010.

(51) Int. Cl.
*A61K 47/18*    (2017.01)
*C07C 217/28*    (2006.01)
(Continued)

(52) U.S. Cl.
CPC .......... *C07C 217/28* (2013.01); *A61K 9/1272* (2013.01); *A61K 9/5123* (2013.01);
(Continued)

(58) Field of Classification Search
CPC ...................................................... A61K 9/127
See application file for complete search history.

(56) References Cited

U.S. PATENT DOCUMENTS 6,251,939 B1 *    6/2001    Schwartz ............. A61K 9/1272
514/506

FOREIGN PATENT DOCUMENTS

| WO | WO 2005/120152 A2 | 12/2005 |
|----|-------------------|---------|
| WO | WO 2009/086558 A1 | 7/2009 |
| WO | WO 2009/132131 A1 | 10/2009 |
| WO | WO 2010/042877 A1 | 4/2010 |
| WO | WO 2010/054401 A1 | 5/2010 |

OTHER PUBLICATIONS

Hung et al. (1996). "Syntheses of Discodermolides Useful for Investigating Microtubule Binding and Stabilization." J. Am. Chem. Soc., 118: 11054-11080.*

(Continued)

*Primary Examiner* — Benjamin Packard
(74) *Attorney, Agent, or Firm* — Viksnins Harris Padys Malen LLP

(57) ABSTRACT

The present invention provides compositions and methods for the delivery of therapeutic agents to cells. In particular, these include novel cationic lipids and nucleic acid-lipid particles that provide efficient encapsulation of nucleic acids and efficient delivery of the encapsulated nucleic acid to cells in vivo. The compositions of the present invention are highly potent, thereby allowing effective knock-down of a specific target protein at relatively low doses. In addition, the compositions and methods of the present invention are less toxic and provide a greater therapeutic index compared to compositions and methods previously known in the art.

30 Claims, 7 Drawing Sheets

Specification includes a Sequence Listing.

(51) Int. Cl.
  C07C 229/12 (2006.01)
  C07D 317/28 (2006.01)
  C12N 15/11 (2006.01)
  A61K 9/127 (2006.01)
  A61K 9/51 (2006.01)
  A61K 31/7105 (2006.01)
  A61K 31/713 (2006.01)

(52) U.S. Cl.
  CPC ........ *A61K 31/713* (2013.01); *A61K 31/7105* (2013.01); *A61K 47/18* (2013.01); *C07C 229/12* (2013.01); *C07D 317/28* (2013.01); *C12N 15/111* (2013.01); C07C 2601/02 (2017.05); C12N 2310/14 (2013.01); C12N 2310/3515 (2013.01); C12N 2320/32 (2013.01)

(56) References Cited

OTHER PUBLICATIONS

Ambegia et al. (2005). "Stabilized plasmid-lipid particles containing PEG-diacylglycerols exhibit extended circulation lifetimes and tumor selective gene expression." Biochimica et Biophysica Acta, 1669: 155-163.*

Patent Cooperation Treaty, International Searching Authority, Search Report and Written Opinion for PCT/GB2011/000722, 10 pages, dated Sep. 7, 2011.

Silvius et al., "Effects of phospholipid acylchain structure on thermotropic phase properties. 2: Phosphatidylcholines with unsaturated or cyclopropane acyl chains", *Chemistry and Physics of Lipids*, vol. 25 (2), 125-134 (1979).

* cited by examiner

SEQUENCE LISTING

```
<160> NUMBER OF SEQ ID NOS: 2

<210> SEQ ID NO 1
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (4)..(4)
<223> OTHER INFORMATION: 2'OMe nucleotide
<220> FEATURE:
<221> NAME/KEY: modified_base
<222> LOCATION: (8)..(8)
<223> OTHER INFORMATION: 2'OMe nucleotide
<220> FEATURE:
<221> NAME/KEY: modified_base
<222> LOCATION: (14)..(14)
<223> OTHER INFORMATION: 2'OMe nucleotide
<220> FEATURE:
<223> OTHER INFORMATION: See specification as filed for detailed
      description of substitutions and preferred embodiments

<400> SEQUENCE: 1
agugucauca cacugaauac c                                              21

<210> SEQ ID NO 2
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (4)..(4)
<223> OTHER INFORMATION: 2'OMe nucleotide
<220> FEATURE:
<221> NAME/KEY: modified_base
<222> LOCATION: (7)..(7)
<223> OTHER INFORMATION: 2'OMe nucleotide
<220> FEATURE:
<221> NAME/KEY: modified_base
<222> LOCATION: (9)..(9)
<223> OTHER INFORMATION: 2'OMe nucleotide
<220> FEATURE:
<221> NAME/KEY: modified_base
<222> LOCATION: (19)..(19)
<223> OTHER INFORMATION: 2'OMe nucleotide
<220> FEATURE:
<223> OTHER INFORMATION: See specification as filed for detailed
      description of substitutions and preferred embodiments

<400> SEQUENCE: 2
uauucagugu gaugacacuu g                                              21
```

CYCLIC CATIONIC LIPIDS AND METHODS OF USE

CROSS-REFERENCE TO RELATED APPLICATION

The present application claims priority to U.S. Provisional Application No. 61/334,096, filed May 12, 2010, the disclosure of which is hereby incorporated by reference in its entirety for all purposes.

SEQUENCE LISTING

The instant application contains a Sequence Listing which has been submitted in ASCII format via EFS-Web and is hereby incorporated by reference in its entirety. Said ASCII copy, created on Jul. 12, 2018, is named 08155_007US1_SL.txt and is 1,560 bytes in size.

BACKGROUND OF THE INVENTION

Therapeutic nucleic acids include, e.g., small interfering RNA (siRNA), microRNA (miRNA), antisense oligonucleotides, ribozymes, plasmids, and immune-stimulating nucleic acids. These nucleic acids act via a variety of mechanisms. In the case of interfering RNA molecules such as siRNA and miRNA, these nucleic acids can down-regulate intracellular levels of specific proteins through a process termed RNA interference (RNAi). Following introduction of interfering RNA into the cell cytoplasm, these double-stranded RNA constructs can bind to a protein termed RISC. The sense strand of the interfering RNA is displaced from the RISC complex, providing a template within RISC that can recognize and bind mRNA with a complementary sequence to that of the bound interfering RNA. Having bound the complementary mRNA, the RISC complex cleaves the mRNA and releases the cleaved strands. RNAi can provide down-regulation of specific proteins by targeting specific destruction of the corresponding mRNA that encodes for protein synthesis.

The therapeutic applications of RNAi are extremely broad, since interfering RNA constructs can be synthesized with any nucleotide sequence directed against a target protein. To date, siRNA constructs have shown the ability to specifically down-regulate target proteins in both in vitro and in vivo models. In addition, siRNA constructs are currently being evaluated in clinical studies.

However, two problems currently faced by interfering RNA constructs are, first, their susceptibility to nuclease digestion in plasma and, second, their limited ability to gain access to the intracellular compartment where they can bind RISC when administered systemically as free interfering RNA molecules. These double-stranded constructs can be stabilized by the incorporation of chemically modified nucleotide linkers within the molecule, e.g., phosphothioate groups. However, such chemically modified linkers provide only limited protection from nuclease digestion and may decrease the activity of the construct. Intracellular delivery of interfering RNA can be facilitated by the use of carrier systems such as polymers, cationic liposomes, or by the covalent attachment of a cholesterol moiety to the molecule. However, improved delivery systems are required to increase the potency of interfering RNA molecules such as siRNA and miRNA and to reduce or eliminate the requirement for chemically modified nucleotide linkers.

In addition, problems remain with the limited ability of therapeutic nucleic acids such as interfering RNA to cross cellular membranes (see, Vlassov et al., *Biochim. Biophys. Acta,* 1197:95-1082 (1994)) and in the problems associated with systemic toxicity, such as complement-mediated anaphylaxis, altered coagulatory properties, and cytopenia (Galbraith et al., *Antisense Nucl. Acid Drug Des.,* 4:201-206 (1994)).

To attempt to improve efficacy, investigators have also employed lipid-based carrier systems to deliver chemically modified or unmodified therapeutic nucleic acids. Zelphati et al. (*J. Contr. Rel.,* 41:99-119 (1996)) describes the use of anionic (conventional) liposomes, pH sensitive liposomes, immunoliposomes, fusogenic liposomes, and cationic lipid/antisense aggregates. Similarly, siRNA has been administered systemically in cationic liposomes, and these nucleic acid-lipid particles have been reported to provide improved down-regulation of target proteins in mammals including non-human primates (Zimmermann et al., *Nature,* 441: 111-114 (2006)).

In spite of this progress, there remains a need in the art for improved lipid-therapeutic nucleic acid compositions that are suitable for general therapeutic use. Preferably, these compositions would encapsulate nucleic acids with high efficiency, have high drug:lipid ratios, protect the encapsulated nucleic acid from degradation and clearance in serum, be suitable for systemic delivery, and provide intracellular delivery of the encapsulated nucleic acid. In addition, these nucleic acid-lipid particles should be well-tolerated and provide an adequate therapeutic index, such that patient treatment at an effective dose of the nucleic acid is not associated with significant toxicity and/or risk to the patient. The present invention provides such compositions, methods of making the compositions, and methods of using the compositions to introduce nucleic acids into cells, including for the treatment of diseases.

BRIEF SUMMARY OF THE INVENTION

The present invention provides novel cationic (amino) lipids and lipid particles comprising these lipids, which are advantageous for the in vivo delivery of active agents or therapeutic agents such as nucleic acids, as well as lipid particles such as nucleic acid-lipid particle compositions suitable for in vivo therapeutic use. The present invention also provides methods of making these lipid compositions, as well as methods of introducing active agents or therapeutic agents such as nucleic acids into cells using these lipid compositions, e.g., for the treatment of various disease conditions.

In one aspect, the present invention provides a cationic lipid of Formula I having the following structure:

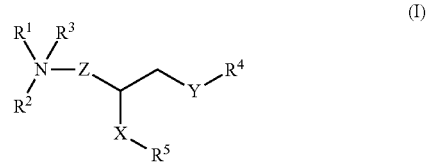

or salts thereof, wherein:
  $R^1$ and $R^2$ are either the same or different and are independently hydrogen (H) or an optionally substituted $C_1$-$C_6$ alkyl, $C_2$-$C_6$ alkenyl, or $C_2$-$C_6$ alkynyl, or $R^1$ and $R^2$ may join to form an optionally substituted heterocyclic ring;

R³ is either absent or, if present, is hydrogen (H) or a C₁-C₆ alkyl to provide a quaternary amine;

R⁴ and R⁵ are either the same or different and are independently an optionally substituted C₁₀-C₂₄ alkyl, C₁₀-C₂₄ alkenyl, C₁₀-C₂₄ alkynyl, or C₁₀-C₂₄ acyl, wherein at least one of R⁴ and R⁵ comprises at least one optionally substituted cyclic alkyl group;

X and Y are either the same or different and are independently O, S, N(R⁶), C(O), C(O)O, OC(O), C(O)N(R⁶), N(R⁶)C(O), OC(O)N(R⁶), N(R⁶)C(O)O, C(O)S, C(S)O, S(O), S(O)(O), C(S), or an optionally substituted heterocyclic ring, wherein R⁶ is hydrogen (H) or an optionally substituted C₁-C₁₀ alkyl, C₂-C₁₀ alkenyl, or C₂-C₁₀ alkynyl; and Z is either absent or, if present, is an optionally substituted C₁-C₆ alkyl, C₂-C₆ alkenyl, or C₂-C₆ alkynyl.

In one embodiment, R¹ and R² are independently selected from the group consisting of a methyl group and an ethyl group, i.e., R¹ and R² are both methyl groups, R¹ and R² are both ethyl groups, or R¹ and R² are a combination of one methyl group and one ethyl group. In another embodiment, R¹ and R² are joined to form an optionally substituted heterocyclic ring having from 2 to 5 carbon atoms (e.g., 2, 3, 4, or 5 carbon atoms, or from 2-5, 2-4, 2-3, 3-5, 3-4, or 4-5 carbon atoms) and from 1 to 3 heteroatoms (e.g., 1, 2, or 3 heteroatoms, or from 1-3, 1-2, or 2-3 heteroatoms) selected from the group consisting of nitrogen (N), oxygen (O), sulfur (S), and combinations thereof. In certain instances, R¹ and R² are joined to form an optionally substituted diazole (e.g., an optionally substituted imidazole) or an optionally substituted triazole.

In yet another embodiment, X and Y are either the same or different and are independently O, C(O)O, C(O)N(R⁶), N(R⁶)C(O)O, or C(O)S. In certain instances, R⁶ is hydrogen (H), an optionally substituted methyl group, an optionally substituted ethyl group, or an optionally substituted C₃-C₁₀ alkyl, alkenyl, or alkynyl group (e.g., an optionally substituted C₃, C₄, C₅, C₆, C₇, C₈, C₉, or C₁₀ alkyl, alkenyl, or alkynyl group). In a further embodiment, X and Y are independently an optionally substituted heterocyclic ring having from 2 to 5 carbon atoms (e.g., 2, 3, 4, or 5 carbon atoms, or from 2-5, 2-4, 2-3, 3-5, 3-4, or 4-5 carbon atoms) and from 1 to 3 heteroatoms (e.g., 1, 2, or 3 heteroatoms, or from 1-3, 1-2, or 2-3 heteroatoms) selected from the group consisting of nitrogen (N), oxygen (O), sulfur (S), and combinations thereof. In certain instances, X and Y are independently an optionally substituted diazole (e.g., an optionally substituted imidazole) or an optionally substituted triazole. In preferred embodiments, X and Y are both O. In other embodiments, Z is (CH₂)ₙ and n is 0, 1, 2, 3, 4, 5, or 6. In particular embodiments, n is 1, 2, 3, or 4 (e.g., n is 1-4, 1-3, 1-2, 2-4, 2-3, or 3-4).

In certain embodiments, at least one of R⁴ and R⁵ comprises at least one, two, three, or more optionally substituted cyclic alkyl groups. In particular embodiments, both R⁴ and R⁵ independently comprise at least one, two, three, or more optionally substituted cyclic alkyl groups. In some instances, both R⁴ and R⁵ comprise the same number of (e.g., 1, 2, 3, 4, 5, 6, or more) optionally substituted cyclic alkyl groups. In other instances, R⁴ and R⁵ comprise a different number of optionally substituted cyclic alkyl groups. In one embodiment, each of the optionally substituted cyclic alkyl groups in R⁴ and/or R⁵ comprises an independently selected optionally substituted saturated cyclic alkyl group or an optionally substituted unsaturated cyclic alkyl group. In certain instances, at least one, two, three, or more of the optionally substituted cyclic alkyl groups present in one or both of R⁴ and R⁵ independently comprises an optionally substituted C₃₋₈ cycloalkyl group such as, e.g., a cyclopropyl group, an optionally substituted C₃₋₈ cycloalkenyl group, and combinations thereof. In some embodiments, one of R⁴ or R⁵ comprises at least one, two, three, or more optionally substituted cyclic alkyl groups and the other side-chain comprises an optionally substituted C₁₀-C₂₄ alkyl, C₁₀-C₂₄ alkenyl, C₁₀-C₂₄ alkynyl, or C₁₀-C₂₄ acyl group (e.g., a side-chain comprising at least one, two, or three sites of unsaturation). In some instances, R⁴ and R⁵ both comprise the same type or types of optionally substituted cyclic alkyl groups. In other instances, R⁴ and R⁵ comprise different types of optionally substituted cyclic alkyl groups.

In particular embodiments, R⁴ and R⁵ are both C₁₂-C₂₀ alkyl groups (e.g., C₁₈ alkyl groups) having at least one, two, three, or more optionally substituted cyclic alkyl groups. In preferred embodiments, R⁴ and R⁵ are both C₁₂-C₂₀ (e.g., C₁₈) alkyl groups having the same number of (e.g., at least one, two, three, or more) optionally substituted cyclic alkyl groups. In certain embodiments, the at least one, two, three, or more optionally substituted cyclic alkyl groups present in both R⁴ and R⁵ independently comprises an optionally substituted saturated cyclic alkyl group (e.g., a C₃₋₈ cycloalkyl group such as a cyclopropyl group) or an optionally substituted unsaturated cyclic alkyl group (e.g., a C₃₋₈ cycloalkenyl group).

In some embodiments, at least one, two, three, or more optionally substituted cyclic alkyl groups are present on each of R⁴ and/or R⁵ in combination with at least one, two, three, or more sites of unsaturation and/or branched alkyl and/or acyl groups. For example, R⁴ may comprise one, two, or three C₃₋₈ cycloalkyl groups such as cyclopropyl groups and one, two, or three sites of unsaturation, while R⁵ may comprise the same or different number and type of substituents.

In particular embodiments, the cationic lipid of Formula I has one of the following structures:

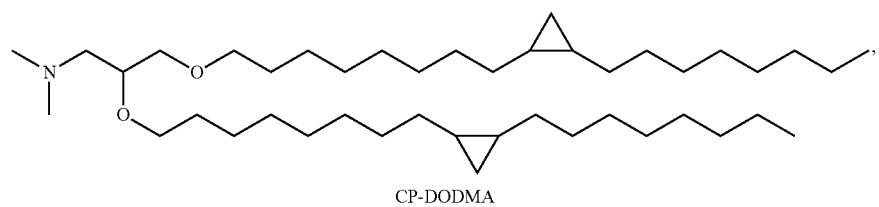

CP-DODMA

-continued

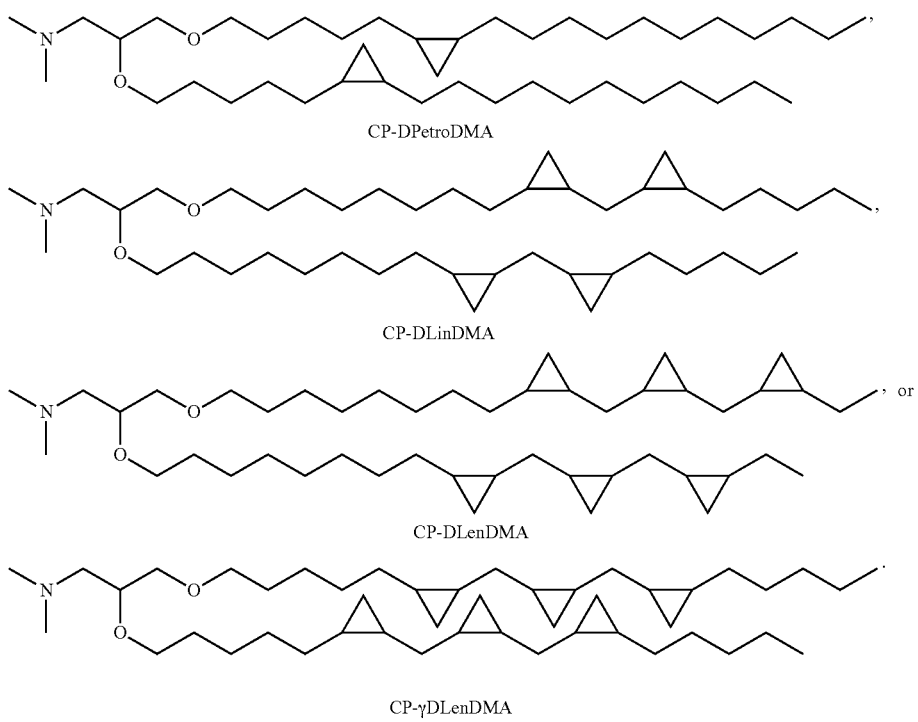

CP-DPetroDMA

CP-DLinDMA

CP-DLenDMA

CP-γDLenDMA

In another aspect, the present invention provides a cationic lipid of Formula II having the following structure:

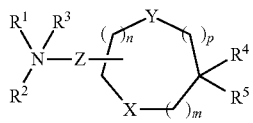

(II)

or salts thereof, wherein:
- $R^1$ and $R^2$ are either the same or different and are independently an optionally substituted $C_1$-$C_6$ alkyl, $C_2$-$C_6$ alkenyl, or $C_2$-$C_6$ alkynyl, or $R^1$ and $R^2$ may join to form an optionally substituted heterocyclic ring;
- $R^3$ is either absent or, if present, is hydrogen (H) or a $C_1$-$C_6$ alkyl to provide a quaternary amine;
- $R^4$ and $R^5$ are either the same or different and are independently an optionally substituted $C_{10}$-$C_{24}$ alkyl, $C_{10}$-$C_{24}$ alkenyl, $C_{10}$-$C_{24}$ alkynyl, or $C_{10}$-$C_{24}$ acyl, wherein at least one of $R^4$ and $R^5$ comprises at least one optionally substituted cyclic alkyl group;
- m, n, and p are either the same or different and are independently either 0, 1, or 2, with the proviso that m, n, and p are not simultaneously 0;
- X and Y are either the same or different and are independently O, S, N($R^6$), C(O), C(O)O, OC(O), C(O)N($R^6$), N($R^6$)C(O), OC(O)N($R^6$), N($R^6$)C(O)O, C(O)S, C(S)O, S(O), S(O)(O), or C(S), wherein $R^6$ is hydrogen (H) or an optionally substituted $C_1$-$C_{10}$ alkyl, $C_2$-$C_{10}$ alkenyl, or $C_2$-$C_{10}$ alkynyl; and
- Z is either absent or, if present, is an optionally substituted $C_1$-$C_6$ alkyl, $C_2$-$C_6$ alkenyl, or $C_2$-$C_6$ alkynyl.

In one embodiment, $R^1$ and $R^2$ are independently selected from the group consisting of a methyl group and an ethyl group, i.e., $R^1$ and $R^2$ are both methyl groups, $R^1$ and $R^2$ are both ethyl groups, or $R^1$ and $R^2$ are a combination of one methyl group and one ethyl group. In another embodiment, $R^1$ and $R^2$ are joined to form an optionally substituted heterocyclic ring having from 2 to 5 carbon atoms (e.g., 2, 3, 4, or 5 carbon atoms, or from 2-5, 2-4, 2-3, 3-5, 3-4, or 4-5 carbon atoms) and from 1 to 3 heteroatoms (e.g., 1, 2, or 3 heteroatoms, or from 1-3, 1-2, or 2-3 heteroatoms) selected from the group consisting of nitrogen (N), oxygen (O), sulfur (S), and combinations thereof. In certain instances, $R^1$ and $R^2$ are joined to form an optionally substituted diazole (e.g., an optionally substituted imidazole) or an optionally substituted triazole.

In yet another embodiment, X and Y are either the same or different and are independently O, C(O)O, C(O)N($R^6$), N($R^6$)C(O)O, or C(O)S. In certain instances, $R^6$ is hydrogen (H), an optionally substituted methyl group, an optionally substituted ethyl group, or an optionally substituted $C_3$-$C_{10}$ alkyl, alkenyl, or alkynyl group (e.g., an optionally substituted $C_3$, $C_4$, $C_5$, $C_6$, $C_7$, $C_8$, $C_9$, or $C_{10}$ alkyl, alkenyl, or alkynyl group). In preferred embodiments, X and Y are both O. In other embodiments, Z is $(CH_2)_q$ and q is 0, 1, 2, 3, 4, 5, or 6. In particular embodiments, q is 1, 2, 3, or 4 (e.g., q is 1-4, 1-3, 1-2, 2-4, 2-3, or 3-4).

In certain embodiments, at least one of $R^4$ and $R^5$ comprises at least one, two, three, or more optionally substituted cyclic alkyl groups. In particular embodiments, both $R^4$ and $R^5$ independently comprise at least one, two, three, or more optionally substituted cyclic alkyl groups. In some instances, both $R^4$ and $R^5$ comprise the same number of (e.g., 1, 2, 3, 4, 5, 6, or more) optionally substituted cyclic alkyl groups. In other instances, $R^4$ and $R^5$ comprise a different number of optionally substituted cyclic alkyl groups. In one embodiment, each of the optionally substituted cyclic alkyl groups in $R^4$ and/or $R^5$ comprises an independently selected optionally substituted saturated cyclic alkyl group or an optionally substituted unsaturated cyclic alkyl group. In certain instances, at least one, two, three, or more of the optionally substituted cyclic alkyl groups present in one or both of $R^4$ and R⁵ independently comprises an optionally substituted C$_{3-8}$ cycloalkyl group such as, e.g., a cyclopropyl group, an optionally substituted C$_{3-8}$ cycloalkenyl group, and combinations thereof. In some embodiments, one of R⁴ or R⁵ comprises at least one, two, three, or more optionally substituted cyclic alkyl groups and the other side-chain comprises an optionally substituted C$_{10}$-C$_{24}$ alkyl, C$_{10}$-C$_{24}$ alkenyl, C$_{10}$-C$_{24}$ alkynyl, or C$_{10}$-C$_{24}$ acyl group (e.g., a side-chain comprising at least one, two, or three sites of unsaturation). In some instances, R⁴ and R⁵ both comprise the same type or types of optionally substituted cyclic alkyl groups. In other instances, R⁴ and R⁵ comprise different types of optionally substituted cyclic alkyl groups.

In particular embodiments, R⁴ and R⁵ are both C$_{12}$-C$_{20}$ alkyl groups (e.g., C$_{18}$ alkyl groups) having at least one, two, three, or more optionally substituted cyclic alkyl groups. In preferred embodiments, R⁴ and R⁵ are both C$_{12}$-C$_{20}$ (e.g., C$_{18}$) alkyl groups having the same number of (e.g., at least one, two, three, or more) optionally substituted cyclic alkyl groups. In certain embodiments, the at least one, two, three, or more optionally substituted cyclic alkyl groups present in both R⁴ and R⁵ independently comprises an optionally substituted saturated cyclic alkyl group (e.g., a C$_{3-8}$ cycloalkyl group such as a cyclopropyl group) or an optionally substituted unsaturated cyclic alkyl group (e.g., a C$_{3-8}$ cycloalkenyl group).

In some embodiments, at least one, two, three, or more optionally substituted cyclic alkyl groups are present on each of R⁴ and/or R⁵ in combination with at least one, two, three, or more sites of unsaturation and/or branched alkyl and/or acyl groups. For example, R⁴ may comprise one, two, or three C$_{3-8}$ cycloalkyl groups such as cyclopropyl groups and one, two, or three sites of unsaturation, while R⁵ may comprise the same or different number and type of substituents.

In particular embodiments, the cationic lipid of Formula II has one of the following structures:

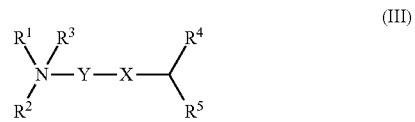

or salts thereof, wherein:

R¹ and R² are either the same or different and are independently hydrogen (H) or an optionally substituted C$_1$-C$_6$ alkyl, C$_2$-C$_6$ alkenyl, or C$_2$-C$_6$ alkynyl, or R¹ and R² may join to form an optionally substituted heterocyclic ring;

R³ is either absent or, if present, is hydrogen (H) or a C$_1$-C$_6$ alkyl to provide a quaternary amine;

R⁴ and R⁵ are either the same or different and are independently an optionally substituted C$_{10}$-C$_{24}$ alkyl, C$_{10}$-C$_{24}$ alkenyl, C$_{10}$-C$_{24}$ alkynyl, or C$_{10}$-C$_{24}$ acyl, wherein at least one of R⁴ and R⁵ comprises at least one optionally substituted cyclic alkyl group;

X is O, S, N(R⁶), C(O), C(O)O, OC(O), C(O)N(R⁶), N(R⁶)C(O), OC(O)N(R⁶), N(R⁶)C(O)O, C(O)S, C(S) O, S(O), S(O)(O), C(S), or an optionally substituted heterocyclic ring, wherein R⁶ is hydrogen (H) or an optionally substituted C$_1$-C$_{10}$ alkyl, C$_2$-C$_{10}$ alkenyl, or C$_2$-C$_{10}$ alkynyl; and Y is either absent or, if present, is an optionally substituted C$_1$-C$_6$ alkyl, C$_2$-C$_6$ alkenyl, or C$_2$-C$_6$ alkynyl.

In one embodiment, R¹ and R² are independently selected from the group consisting of a methyl group and an ethyl group, i.e., R¹ and R² are both methyl groups, R¹ and R² are both ethyl groups, or R¹ and R² are a combination of one methyl group and one ethyl group. In another embodiment, R¹ and R² are joined to form an optionally substituted heterocyclic ring having from 2 to 5 carbon atoms (e.g., 2, 3, 4, or 5 carbon atoms, or from 2-5, 2-4, 2-3, 3-5, 3-4, or

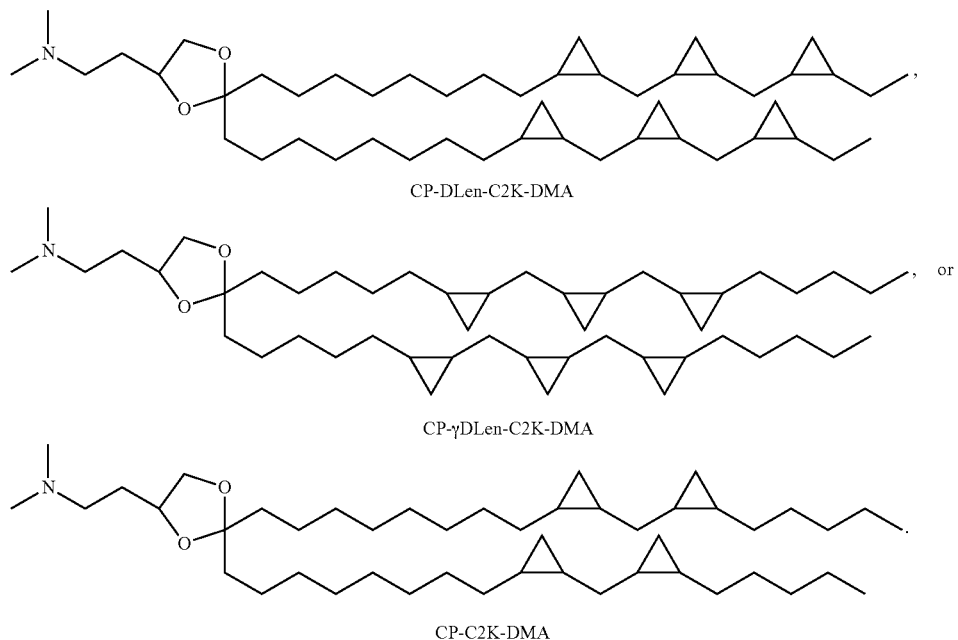

In yet another aspect, the present invention provides a cationic lipid of Formula III having the following structure:

4-5 carbon atoms) and from 1 to 3 heteroatoms (e.g., 1, 2, or 3 heteroatoms, or from 1-3, 1-2, or 2-3 heteroatoms)

selected from the group consisting of nitrogen (N), oxygen (O), sulfur (S), and combinations thereof. In certain instances, $R^1$ and $R^2$ are joined to form an optionally substituted diazole (e.g., an optionally substituted imidazole) or an optionally substituted triazole.

In yet another embodiment, X is O, C(O)O, C(O)N($R^6$), N($R^6$)C(O)O, or C(O)S. In certain instances, $R^6$ is hydrogen (H), an optionally substituted methyl group, an optionally substituted ethyl group, or an optionally substituted $C_3$-$C_{10}$ alkyl, alkenyl, or alkynyl group (e.g., an optionally substituted $C_3$, $C_4$, $C_5$, $C_6$, $C_7$, $C_8$, $C_9$, or $C_{10}$ alkyl, alkenyl, or alkynyl group). In a further embodiment, X is an optionally substituted heterocyclic ring having from 2 to 5 carbon atoms (e.g., 2, 3, 4, or 5 carbon atoms, or from 2-5, 2-4, 2-3, 3-5, 3-4, or 4-5 carbon atoms) and from 1 to 3 heteroatoms (e.g., 1, 2, or 3 heteroatoms, or from 1-3, 1-2, or 2-3 heteroatoms) selected from the group consisting of nitrogen (N), oxygen (O), sulfur (S), and combinations thereof. In certain instances, X is an optionally substituted diazole (e.g., an optionally substituted imidazole) or an optionally substituted triazole. In preferred embodiments, X is C(O)O. In other embodiments, Y is $(CH_2)_n$ and n is 0, 1, 2, 3, 4, 5, or 6. In particular embodiments, n is 1, 2, 3, or 4 (e.g., n is 1-4, 1-3, 1-2, 2-4, 2-3, or 3-4).

In certain embodiments, at least one of $R^4$ and $R^5$ comprises at least one, two, three, or more optionally substituted cyclic alkyl groups. In particular embodiments, both $R^4$ and $R^5$ independently comprise at least one, two, three, or more optionally substituted cyclic alkyl groups. In some instances, both $R^4$ and $R^5$ comprise the same number of (e.g., 1, 2, 3, 4, 5, 6, or more) optionally substituted cyclic alkyl groups. In other instances, $R^4$ and $R^5$ comprise a different number of optionally substituted cyclic alkyl groups. In one embodiment, each of the optionally substituted cyclic alkyl groups in $R^4$ and/or $R^5$ comprises an independently selected optionally substituted saturated cyclic alkyl group or an optionally substituted unsaturated cyclic alkyl group. In certain instances, at least one, two, three, or more of the optionally substituted cyclic alkyl groups present in one or both of $R^4$ and $R^5$ independently comprises an optionally substituted $C_{3-8}$ cycloalkyl group such as, e.g., a cyclopropyl group, an optionally substituted $C_{3-8}$ cycloalkenyl group, and combinations thereof. In some embodiments, one of $R^4$ or $R^5$ comprises at least one, two, three, or more optionally substituted cyclic alkyl groups and the other side-chain comprises an optionally substituted $C_{10}$-$C_{24}$ alkyl, $C_{10}$-$C_{24}$ alkenyl, $C_{10}$-$C_{24}$ alkynyl, or $C_{10}$-$C_{24}$ acyl group (e.g., a side-chain comprising at least one, two, or three sites of unsaturation). In some instances, $R^4$ and $R^5$ both comprise the same type or types of optionally substituted cyclic alkyl groups. In other instances, $R^4$ and $R^5$ comprise different types of optionally substituted cyclic alkyl groups.

In particular embodiments, $R^4$ and $R^5$ are both $C_{12}$-$C_{20}$ alkyl groups (e.g., $C_{18}$ alkyl groups) having at least one, two, three, or more optionally substituted cyclic alkyl groups. In preferred embodiments, $R^4$ and $R^5$ are both $C_{12}$-$C_{20}$ (e.g., $C_{18}$) alkyl groups having the same number of (e.g., at least one, two, three, or more) optionally substituted cyclic alkyl groups. In certain embodiments, the at least one, two, three, or more optionally substituted cyclic alkyl groups present in both $R^4$ and $R^5$ independently comprises an optionally substituted saturated cyclic alkyl group (e.g., a $C_{3-8}$ cycloalkyl group such as a cyclopropyl group) or an optionally substituted unsaturated cyclic alkyl group (e.g., a $C_{3-8}$ cycloalkenyl group).

In some embodiments, at least one, two, three, or more optionally substituted cyclic alkyl groups are present on each of $R^4$ and/or $R^5$ in combination with at least one, two, three, or more sites of unsaturation and/or branched alkyl and/or acyl groups. For example, $R^4$ may comprise one, two, or three $C_{3-8}$ cycloalkyl groups such as cyclopropyl groups and one, two, or three sites of unsaturation, while $R^5$ may comprise the same or different number and type of substituents.

In particular embodiments, the cationic lipid of Formula III has one of the following structures:

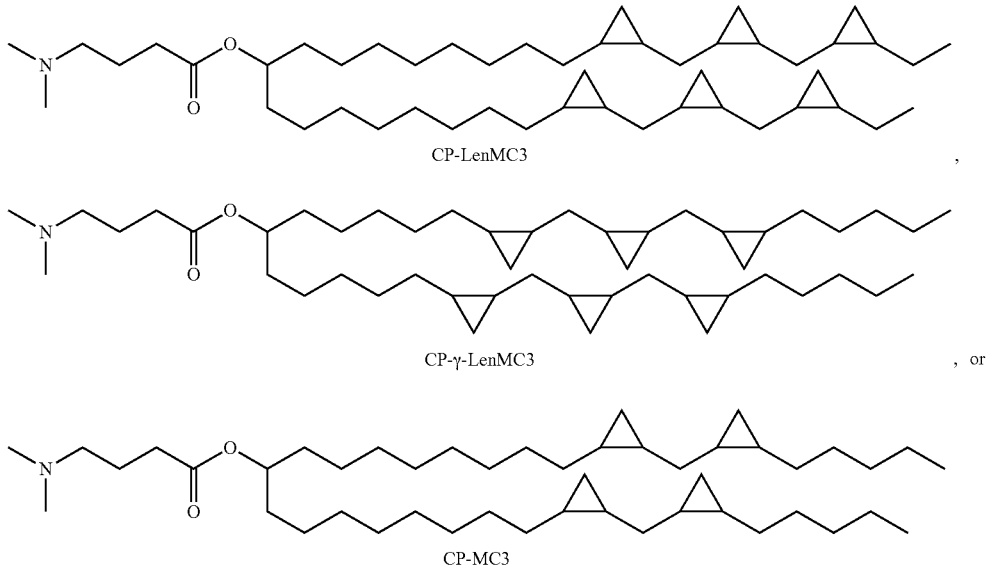

CP-LenMC3

CP-γ-LenMC3, or

CP-MC3

In a further aspect, the present invention provides a lipid particle comprising one or more of the above cationic lipids of Formulas I-III or salts thereof. In certain embodiments, the lipid particle further comprises one or more non-cationic lipids such as neutral lipids. In certain other embodiments, the lipid particle further comprises one or more conjugated lipids capable of reducing or inhibiting particle aggregation. In additional embodiments, the lipid particle further comprises one or more active agents or therapeutic agents.

In certain embodiments, the non-cationic lipid component of the lipid particle may comprise a phospholipid, cholesterol (or cholesterol derivative), or a mixture thereof. In one particular embodiment, the phospholipid comprises dipalmitoylphosphatidylcholine (DPPC), distearoylphosphatidylcholine (DSPC), or a mixture thereof. In some embodiments, the conjugated lipid component of the lipid particle comprises a polyethyleneglycol (PEG)-lipid conjugate. In certain instances, the PEG-lipid conjugate comprises a PEG-diacylglycerol (PEG-DAG) conjugate, a PEG-dialkyloxypropyl (PEG-DAA) conjugate, or a mixture thereof. In other embodiments, the lipid conjugate comprises a polyoxazoline (POZ)-lipid conjugate such as a POZ-DAA conjugate.

In some embodiments, the active agent or therapeutic agent comprises a nucleic acid. In certain instances, the nucleic acid comprises an interfering RNA molecule which includes any double-stranded RNA capable of mediating RNAi, such as, e.g., an siRNA, Dicer-substrate dsRNA, shRNA, aiRNA, pre-miRNA, or mixtures thereof. In certain other instances, the nucleic acid comprises single-stranded or double-stranded DNA, RNA, or a DNA/RNA hybrid such as, e.g., an antisense oligonucleotide, a ribozyme, a plasmid, an immunostimulatory oligonucleotide, or mixtures thereof.

In other embodiments, the active agent or therapeutic agent is fully encapsulated within the lipid portion of the lipid particle such that the active agent or therapeutic agent in the lipid particle is resistant in aqueous solution to enzymatic degradation, e.g., by a nuclease or protease. In further embodiments, the lipid particle is substantially non-toxic to mammals such as humans.

In preferred embodiments, the present invention provides serum-stable nucleic acid-lipid particles (SNALP) comprising: (a) one or more nucleic acids such as interfering RNA molecules; (b) one or more cationic lipids of Formulas I-III or salts thereof; (c) one or more non-cationic lipids; and (d) one or more conjugated lipids that inhibit aggregation of particles.

In some embodiments, the present invention provides nucleic acid-lipid particles (e.g., SNALP) comprising: (a) one or more nucleic acids; (b) one or more cationic lipids of Formulas I-III or salts thereof comprising from about 50 mol % to about 85 mol % of the total lipid present in the particle; (c) one or more non-cationic lipids comprising from about 13 mol % to about 49.5 mol % of the total lipid present in the particle; and (d) one or more conjugated lipids that inhibit aggregation of particles comprising from about 0.5 mol % to about 2 mol % of the total lipid present in the particle.

In one aspect of this embodiment, the nucleic acid-lipid particle comprises: (a) one or more nucleic acids; (b) one or more cationic lipids of Formulas I-III or a salt thereof comprising from about 50 mol % to about 65 mol % of the total lipid present in the particle; (c) one or more non-cationic lipids comprising a mixture of one or more phospholipids and cholesterol or a derivative thereof, wherein the one or more phospholipids comprises from about 4 mol % to about 10 mol % of the total lipid present in the particle and the cholesterol or derivative thereof comprises from about 30 mol % to about 40 mol % of the total lipid present in the particle; and (d) one or more PEG-lipid conjugates comprising from about 0.5 mol % to about 2 mol % of the total lipid present in the particle. This embodiment of nucleic acid-lipid particle is generally referred to herein as the "1:57" formulation.

In certain instances, the 1:57 formulation comprises: (a) one or more nucleic acids; (b) one or more cationic lipids of Formulas I-III or a salt thereof comprising from about 52 mol % to about 62 mol % of the total lipid present in the particle; (c) a mixture of one or more phospholipids and cholesterol or a derivative thereof comprising from about 36 mol % to about 47 mol % of the total lipid present in the particle; and (d) one or more PEG-lipid conjugates comprising from about 1 mol % to about 2 mol % of the total lipid present in the particle. In one particular embodiment, the 1:57 formulation is a four-component system comprising about 1.4 mol % PEG-lipid conjugate (e.g., PEG2000-C-DMA), about 57.1 mol % cationic lipid of Formulas I-III or a salt thereof, about 7.1 mol % DPPC (or DSPC), and about 34.3 mol % cholesterol (or derivative thereof).

In another aspect of this embodiment, the nucleic acid-lipid particle comprises: (a) one or more nucleic acids; (b) one or more cationic lipids of Formulas I-III or a salt thereof comprising from about 56.5 mol % to about 66.5 mol % of the total lipid present in the particle; (c) cholesterol and/or one or more derivatives thereof comprising from about 31.5 mol % to about 42.5 mol % of the total lipid present in the particle; and (d) one or more PEG-lipid conjugates comprising from about 1 mol % to about 2 mol % of the total lipid present in the particle. This embodiment of nucleic acid-lipid particle is generally referred to herein as the "1:62" formulation. In one particular embodiment, the 1:62 formulation is a three-component system which is phospholipid-free and comprises about 1.5 mol % PEG-lipid conjugate (e.g., PEG2000-C-DMA), about 61.5 mol % cationic lipid of Formulas I-III or a salt thereof, and about 36.9 mol % cholesterol (or derivative thereof).

Additional embodiments related to the 1:57 and 1:62 formulations are described in PCT Publication No. WO 09/127,060 and U.S. Publication No. 20110071208, the disclosures of which are herein incorporated by reference in their entirety for all purposes.

In other embodiments, the present invention provides nucleic acid-lipid particles (e.g., SNALP) comprising: (a) one or more nucleic acids; (b) one or more cationic lipids of Formulas I-III or salts thereof comprising from about 2 mol % to about 50 mol % of the total lipid present in the particle; (c) one or more non-cationic lipids comprising from about 5 mol % to about 90 mol % of the total lipid present in the particle; and (d) one or more conjugated lipids that inhibit aggregation of particles comprising from about 0.5 mol % to about 20 mol % of the total lipid present in the particle.

In one aspect of this embodiment, the nucleic acid-lipid particle comprises: (a) one or more nucleic acids; (b) one or more cationic lipids of Formulas I-III or a salt thereof comprising from about 30 mol % to about 50 mol % of the total lipid present in the particle; (c) a mixture of one or more phospholipids and cholesterol or a derivative thereof comprising from about 47 mol % to about 69 mol % of the total lipid present in the particle; and (d) one or more PEG-lipid conjugates comprising from about 1 mol % to about 3 mol % of the total lipid present in the particle. This embodiment of nucleic acid-lipid particle is generally referred to herein as the "2:40" formulation. In one particular embodiment, the 2:40 formulation is a four-component system which comprises about 2 mol % PEG-lipid conjugate (e.g., PEG2000-C-DMA), about 40 mol % cationic lipid of Formulas I-III or a salt thereof, about 10 mol % DPPC (or DSPC), and about 48 mol % cholesterol (or derivative thereof).

In further embodiments, the present invention provides nucleic acid-lipid particles (e.g., SNALP) comprising: (a) one or more nucleic acids; (b) one or more cationic lipids of Formulas I-III or salts thereof comprising from about 50 mol % to about 65 mol % of the total lipid present in the particle; (c) one or more non-cationic lipids comprising from about 25 mol % to about 45 mol % of the total lipid present in the particle; and (d) one or more conjugated lipids that inhibit aggregation of particles comprising from about 5 mol % to about 10 mol % of the total lipid present in the particle.

In one aspect of this embodiment, the nucleic acid-lipid particle comprises: (a) one or more nucleic acids; (b) one or more cationic lipids of Formulas I-III or a salt thereof comprising from about 50 mol % to about 60 mol % of the total lipid present in the particle; (c) a mixture of one or more phospholipids and cholesterol or a derivative thereof comprising from about 35 mol % to about 45 mol % of the total lipid present in the particle; and (d) one or more PEG-lipid conjugates comprising from about 5 mol % to about 10 mol % of the total lipid present in the particle. This embodiment of nucleic acid-lipid particle is generally referred to herein as the "7:54" formulation. In certain instances, the non-cationic lipid mixture in the 7:54 formulation comprises: (i) a phospholipid of from about 5 mol % to about 10 mol % of the total lipid present in the particle; and (ii) cholesterol or a derivative thereof of from about 25 mol % to about 35 mol % of the total lipid present in the particle. In one particular embodiment, the 7:54 formulation is a four-component system which comprises about 7 mol % PEG-lipid conjugate (e.g., PEG750-C-DMA), about 54 mol % cationic lipid of Formulas I-III or a salt thereof, about 7 mol % DPPC (or DSPC), and about 32 mol % cholesterol (or derivative thereof).

In another aspect of this embodiment, the nucleic acid-lipid particle comprises: (a) one or more nucleic acids; (b) one or more cationic lipids of Formulas I-III or a salt thereof comprising from about 55 mol % to about 65 mol % of the total lipid present in the particle; (c) cholesterol and/or one or more derivatives thereof comprising from about 30 mol % to about 40 mol % of the total lipid present in the particle; and (d) one or more PEG-lipid conjugates comprising from about 5 mol % to about 10 mol % of the total lipid present in the particle. This embodiment of nucleic acid-lipid particle is generally referred to herein as the "7:58" formulation. In one particular embodiment, the 7:58 formulation is a three-component system which is phospholipid-free and comprises about 7 mol % PEG-lipid conjugate (e.g., PEG750-C-DMA), about 58 mol % cationic lipid of Formulas I-III or a salt thereof, and about 35 mol % cholesterol (or derivative thereof).

Additional embodiments related to the 7:54 and 7:58 formulations are described in U.S. Patent Publication No. 20110076335, the disclosure of which is herein incorporated by reference in its entirety for all purposes.

The present invention also provides pharmaceutical compositions comprising a lipid particle such as a nucleic acid-lipid particle (e.g., SNALP) and a pharmaceutically acceptable carrier.

In another aspect, the present invention provides methods for introducing one or more therapeutic agents such as nucleic acids into a cell, the method comprising contacting the cell with a lipid particle described herein (e.g., SNALP). In one embodiment, the cell is in a mammal and the mammal is a human.

In yet another aspect, the present invention provides methods for the in vivo delivery of one or more therapeutic agents such as nucleic acids, the method comprising administering to a mammal a lipid particle described herein (e.g., SNALP). In certain embodiments, the lipid particles (e.g., SNALP) are administered by one of the following routes of administration: oral, intranasal, intravenous, intraperitoneal, intramuscular, intraarticular, intralesional, intratracheal, subcutaneous, and intradermal. In particular embodiments, the lipid particles (e.g., SNALP) are administered systemically, e.g., via enteral or parenteral routes of administration. In preferred embodiments, the mammal is a human.

In a further aspect, the present invention provides methods for treating a disease or disorder in a mammal in need thereof, the method comprising administering to the mammal a therapeutically effective amount of a lipid particle (e.g., SNALP) comprising one or more therapeutic agents such as nucleic acids. Non-limiting examples of diseases or disorders include a viral infection, a liver disease or disorder, and cancer. Preferably, the mammal is a human.

In certain embodiments, the present invention provides methods for treating a liver disease or disorder by administering a nucleic acid such as an interfering RNA (e.g., siRNA) in nucleic acid-lipid particles (e.g., SNALP), alone or in combination with a lipid-lowering agent. Examples of lipid diseases and disorders include, but are not limited to, dyslipidemia (e.g., hyperlipidemias such as elevated triglyceride levels (hypertriglyceridemia) and/or elevated cholesterol levels (hypercholesterolemia)), atherosclerosis, coronary heart disease, coronary artery disease, atherosclerotic cardiovascular disease (CVD), fatty liver disease (hepatic steatosis), abnormal lipid metabolism, abnormal cholesterol metabolism, diabetes (including Type 2 diabetes), obesity, cardiovascular disease, and other disorders relating to abnormal metabolism. Non-limiting examples of lipid-lowering agents include statins, fibrates, ezetimibe, thiazolidinediones, niacin, beta-blockers, nitroglycerin, calcium antagonists, and fish oil.

In one particular embodiment, the present invention provides a method for lowering or reducing cholesterol levels in a mammal (e.g., human) in need thereof (e.g., a mammal with elevated blood cholesterol levels), the method comprising administering to the mammal a therapeutically effective amount of a nucleic acid-lipid particle (e.g., a SNALP formulation) described herein comprising one or more interfering RNAs (e.g., siRNAs) that target one or more genes associated with metabolic diseases and disorders. In another particular embodiment, the present invention provides a method for lowering or reducing triglyceride levels in a mammal (e.g., human) in need thereof (e.g., a mammal with elevated blood triglyceride levels), the method comprising administering to the mammal a therapeutically effective amount of a nucleic acid-lipid particle (e.g., a SNALP formulation) described herein comprising one or more interfering RNAs (e.g., siRNAs) that target one or more genes associated with metabolic diseases and disorders. These methods can be carried out in vitro using standard tissue culture techniques or in vivo by administering the interfering RNA (e.g., siRNA) using any means known in the art. In preferred embodiments, the interfering RNA (e.g., siRNA) is delivered to a liver cell (e.g., hepatocyte) in a mammal such as a human.

Additional embodiments related to treating a liver disease or disorder using a lipid particle are described in, e.g., PCT Publication No. WO 2010/083615, and U.S. Patent Publication No. 20060134189, the disclosures of which are herein incorporated by reference in their entirety for all purposes.

In other embodiments, the present invention provides methods for treating a cell proliferative disorder such as cancer by administering a nucleic acid such as an interfering RNA (e.g., siRNA) in nucleic acid-lipid particles (e.g., SNALP), alone or in combination with a chemotherapy drug. The methods can be carried out in vitro using standard tissue culture techniques or in vivo by administering the interfering RNA (e.g., siRNA) using any means known in the art. In preferred embodiments, the interfering RNA (e.g., siRNA) is delivered to a cancer cell in a mammal such as a human, alone or in combination with a chemotherapy drug. The nucleic acid-lipid particles and/or chemotherapy drugs may also be co-administered with conventional hormonal, immunotherapeutic, and/or radiotherapeutic agents.

Additional embodiments related to treating a cell proliferative disorder using a lipid particle are described in, e.g., PCT Publication No. WO 09/082,817, U.S. Patent Publication No. 20090149403, PCT Publication No. WO 09/129, 319, and PCT Publication No. WO 2011/038160, the disclosures of which are herein incorporated by reference in their entirety for all purposes.

In further embodiments, the present invention provides methods for preventing or treating a viral infection such as an arenavirus (e.g., Lassa virus) or filovirus (e.g., Ebola virus, Marburg virus, etc.) infection which causes hemorrhagic fever or a hepatitis (e.g., Hepatitis C virus) infection which causes acute or chronic hepatitis by administering a nucleic acid such as an interfering RNA (e.g., siRNA) in nucleic acid-lipid particles (e.g., SNALP), alone or in combination with the administration of conventional agents used to treat or ameliorate the viral condition or any of the symptoms associated therewith. The methods can be carried out in vitro using standard tissue culture techniques or in vivo by administering the interfering RNA using any means known in the art. In certain preferred embodiments, the interfering RNA (e.g., siRNA) is delivered to cells, tissues, or organs of a mammal such as a human that are infected and/or susceptible of being infected with the hemorrhagic fever virus, such as, e.g., cells of the reticuloendothelial system (e.g., monocytes, macrophages, etc.), endothelial cells, liver cells (e.g., hepatocytes), fibroblast cells, and/or platelet cells. In certain other preferred embodiments, the interfering RNA (e.g., siRNA) is delivered to cells, tissues, or organs of a mammal such as a human that are infected and/or susceptible of being infected with the hepatitis virus, such as, e.g., cells of the liver (e.g., hepatocytes).

Additional embodiments related to preventing or treating a viral infection using a lipid particle are described in, e.g., U.S. Patent Publication No. 20070218122, U.S. Patent Publication No. 20070135370, PCT Publication No. WO 2011/011447, PCT Publication No. WO 2010/105372, and U.S. patent application Ser. No. 13/077,856, filed Mar. 31, 2011, the disclosures of which are herein incorporated by reference in their entirety for all purposes.

The lipid particles of the invention (e.g., SNALP) comprising one or more cationic lipids of Formulas I-III or salts thereof are particularly advantageous and suitable for use in the administration of nucleic acids such as interfering RNA to a subject (e.g., a mammal such as a human) because they are stable in circulation, of a size required for pharmacodynamic behavior resulting in access to extravascular sites, and are capable of reaching target cell populations.

Other objects, features, and advantages of the present invention will be apparent to one of skill in the art from the following detailed description and figures.

DETAILED DESCRIPTION OF THE INVENTION

I. Introduction

Figure 1:
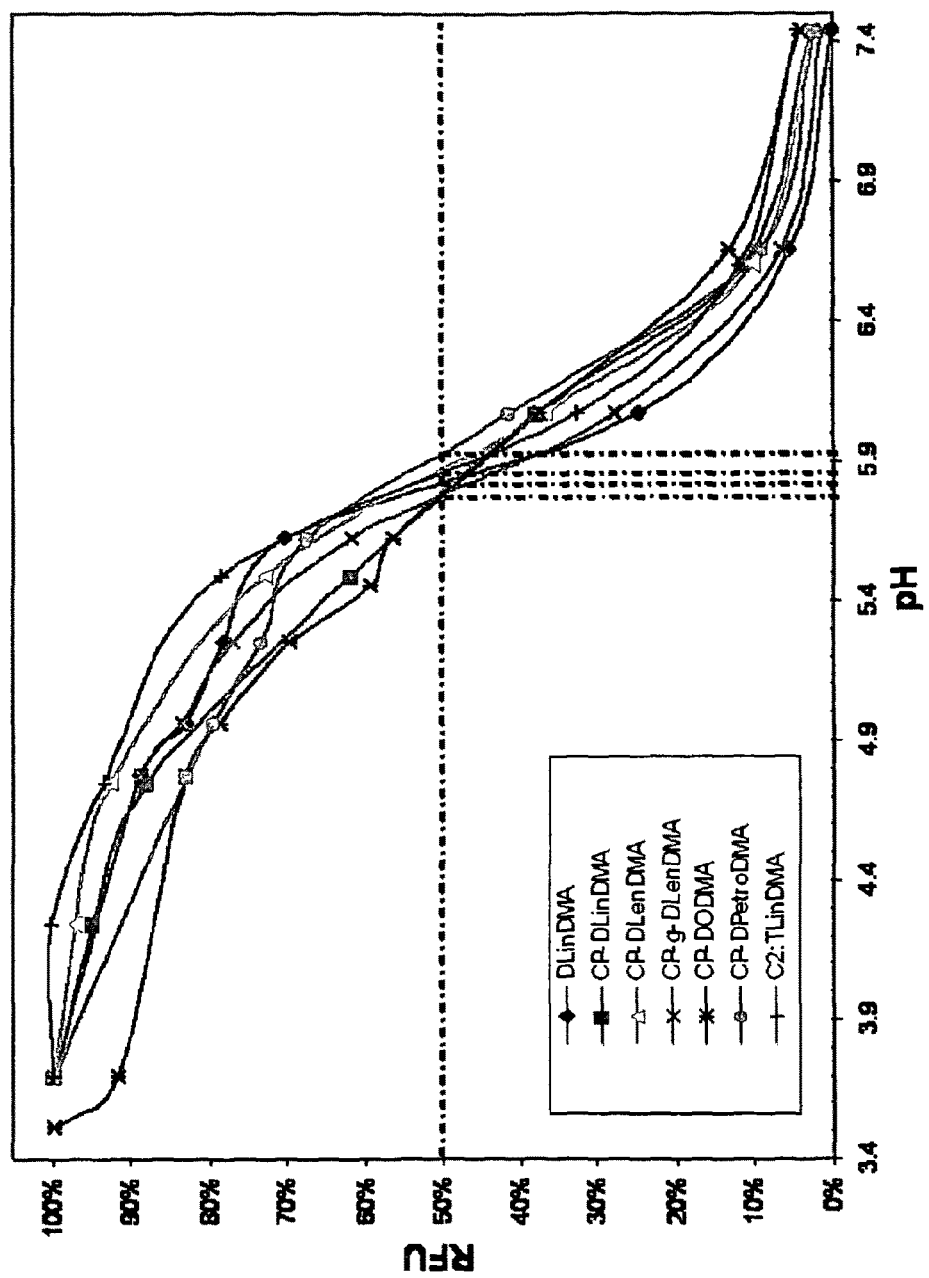
FIG. 1 shows the apparent $pK_a$ values of exemplary SNALP formulations containing cationic lipids of Formula I.

The present invention is based, in part, upon the discovery of novel cationic (amino) lipids that provide advantages when used in lipid particles for the in vivo delivery of an active or therapeutic agent such as a nucleic acid into a cell of a mammal. In particular, the present invention provides nucleic acid-lipid particle compositions comprising one or more of the novel cationic lipids described herein that provide increased activity of the nucleic acid (e.g., interfering RNA) and improved tolerability of the compositions in vivo, resulting in a significant increase in the therapeutic index as compared to nucleic acid-lipid particle compositions previously described.

In particular embodiments, the present invention provides novel cationic lipids that enable the formulation of improved compositions for the in vitro and in vivo delivery of interfering RNA such as siRNA. It is shown herein that these improved lipid particle compositions are effective in down-regulating (e.g., silencing) the protein levels and/or mRNA levels of target genes. Furthermore, it is shown herein that the activity of these improved lipid particle compositions is dependent on the presence of the novel cationic lipids of the invention.

The lipid particles and compositions of the present invention may be used for a variety of purposes, including the delivery of encapsulated or associated (e.g., complexed) therapeutic agents such as nucleic acids to cells, both in vitro and in vivo. Accordingly, the present invention further provides methods of treating diseases or disorders in a subject in need thereof by contacting the subject with a lipid particle that encapsulates or is associated with a suitable therapeutic agent, wherein the lipid particle comprises one or more of the novel cationic lipids described herein.

As described herein, the lipid particles of the present invention are particularly useful for the delivery of nucleic acids, including, e.g., interfering RNA molecules such as siRNA. Therefore, the lipid particles and compositions of the present invention may be used to decrease the expression of target genes and proteins both in vitro and in vivo by contacting cells with a lipid particle comprising one or more novel cationic lipids described herein, wherein the lipid particle encapsulates or is associated with a nucleic acid that reduces target gene expression (e.g., an siRNA). Alternatively, the lipid particles and compositions of the present invention may be used to increase the expression of a desired protein both in vitro and in vivo by contacting cells with a lipid particle comprising one or more novel cationic lipids described herein, wherein the lipid particle encapsulates or is associated with a nucleic acid that enhances expression of the desired protein (e.g., a plasmid encoding the desired protein).

Various exemplary embodiments of the cationic lipids of the present invention, lipid particles and compositions comprising the same, and their use to deliver active or therapeutic agents such as nucleic acids to modulate gene and protein expression, are described in further detail below.

II. Definitions

As used herein, the following terms have the meanings ascribed to them unless specified otherwise.

The term "interfering RNA" or "RNAi" or "interfering RNA sequence" as used herein includes single-stranded RNA (e.g., mature miRNA, ssRNAi oligonucleotides, ssDNAi oligonucleotides), double-stranded RNA (i.e., duplex RNA such as siRNA, Dicer-substrate dsRNA, shRNA, aiRNA, or pre-miRNA), a DNA-RNA hybrid (see, e.g., PCT Publication No. WO 2004/078941), or a DNA-DNA hybrid (see, e.g., PCT Publication No. WO 2004/104199) that is capable of reducing or inhibiting the expression of a target gene or sequence (e.g., by mediating the degradation or inhibiting the translation of mRNAs which are complementary to the interfering RNA sequence) when the interfering RNA is in the same cell as the target gene or sequence. Interfering RNA thus refers to the single-stranded RNA that is complementary to a target mRNA sequence or to the double-stranded RNA formed by two complementary strands or by a single, self-complementary strand. Interfering RNA may have substantial or complete identity to the target gene or sequence, or may comprise a region of mismatch (i.e., a mismatch motif). The sequence of the interfering RNA can correspond to the full-length target gene, or a subsequence thereof. Preferably, the interfering RNA molecules are chemically synthesized. The disclosures of each of the above patent documents are herein incorporated by reference in their entirety for all purposes.

Interfering RNA includes "small-interfering RNA" or "siRNA," e.g., interfering RNA of about 15-60, 15-50, or 15-40 (duplex) nucleotides in length, more typically about 15-30, 15-25, or 19-25 (duplex) nucleotides in length, and is preferably about 20-24, 21-22, or 21-23 (duplex) nucleotides in length (e.g., each complementary sequence of the double-stranded siRNA is 15-60, 15-50, 15-40, 15-30, 15-25, or 19-25 nucleotides in length, preferably about 20-24, 21-22, or 21-23 nucleotides in length, and the double-stranded siRNA is about 15-60, 15-50, 15-40, 15-30, 15-25, or 19-25 base pairs in length, preferably about 18-22, 19-20, or 19-21 base pairs in length). siRNA duplexes may comprise 3' overhangs of about 1 to about 4 nucleotides or about 2 to about 3 nucleotides and 5' phosphate termini. Examples of siRNA include, without limitation, a double-stranded polynucleotide molecule assembled from two separate stranded molecules, wherein one strand is the sense strand and the other is the complementary antisense strand; a double-stranded polynucleotide molecule assembled from a single stranded molecule, where the sense and antisense regions are linked by a nucleic acid-based or non-nucleic acid-based linker; a double-stranded polynucleotide molecule with a hairpin secondary structure having self-complementary sense and antisense regions; and a circular single-stranded polynucleotide molecule with two or more loop structures and a stem having self-complementary sense and antisense regions, where the circular polynucleotide can be processed in vivo or in vitro to generate an active double-stranded siRNA molecule. As used herein, the term "siRNA" includes RNA-RNA duplexes as well as DNA-RNA hybrids (see, e.g., PCT Publication No. WO 2004/078941).

Preferably, siRNA are chemically synthesized. siRNA can also be generated by cleavage of longer dsRNA (e.g., dsRNA greater than about 25 nucleotides in length) with the E. coli RNase III or Dicer. These enzymes process the dsRNA into biologically active siRNA (see, e.g., Yang et al., Proc. Natl. Acad. Sci. USA, 99:9942-9947 (2002); Calegari et al., Proc. Natl. Acad. Sci. USA, 99:14236 (2002); Byrom et al., Ambion TechNotes, 10(1):4-6 (2003); Kawasaki et al., Nucleic Acids Res., 31:981-987 (2003); Knight et al., Science, 293:2269-2271 (2001); and Robertson et al., J. Biol. Chem., 243:82 (1968)). Preferably, dsRNA are at least 50 nucleotides to about 100, 200, 300, 400, or 500 nucleotides in length. A dsRNA may be as long as 1000, 1500, 2000, 5000 nucleotides in length, or longer. The dsRNA can encode for an entire gene transcript or a partial gene transcript. In certain instances, siRNA may be encoded by a plasmid (e.g., transcribed as sequences that automatically fold into duplexes with hairpin loops).

As used herein, the term "mismatch motif" or "mismatch region" refers to a portion of an interfering RNA (e.g., siRNA) sequence that does not have 100% complementarity to its target sequence. An interfering RNA may have at least one, two, three, four, five, six, or more mismatch regions. The mismatch regions may be contiguous or may be separated by 1, 2, 3, 4, 5, 6, 7, 8, 9, 10, 11, 12, or more nucleotides. The mismatch motifs or regions may comprise a single nucleotide or may comprise two, three, four, five, or more nucleotides.

The phrase "inhibiting expression of a target gene" refers to the ability of a nucleic acid such as an interfering RNA (e.g., siRNA) to silence, reduce, or inhibit the expression of a target gene. To examine the extent of gene silencing, a test sample (e.g., a sample of cells in culture expressing the target gene) or a test mammal (e.g., a mammal such as a human or an animal model such as a rodent (e.g., mouse) or a non-human primate (e.g., monkey) model) is contacted with a nucleic acid such as an interfering RNA (e.g., siRNA) that silences, reduces, or inhibits expression of the target gene. Expression of the target gene in the test sample or test animal is compared to expression of the target gene in a control sample (e.g., a sample of cells in culture expressing the target gene) or a control mammal (e.g., a mammal such as a human or an animal model such as a rodent (e.g., mouse) or non-human primate (e.g., monkey) model) that is not contacted with or administered the nucleic acid (e.g., interfering RNA). The expression of the target gene in a control sample or a control mammal may be assigned a value of 100%. In particular embodiments, silencing, inhibition, or reduction of expression of a target gene is achieved when the level of target gene expression in the test sample or the test mammal relative to the level of target gene expression in the control sample or the control mammal is about 95%, 90%, 85%, 80%, 75%, 70%, 65%, 60%, 55%, 50%, 45%, 40%, 35%, 30%, 25%, 20%, 15%, 10%, 5%, or 0%. In other words, the nucleic acids (e.g., interfering RNAs) are capable of silencing, reducing, or inhibiting the expression of a target gene by at least about 5%, 10%, 15%, 20%, 25%, 30%, 35%, 40%, 45%, 50%, 55%, 60%, 65%, 70%, 75%, 80%, 85%, 90%, 95%, or 100% in a test sample or a test mammal relative to the level of target gene expression in a control sample or a control mammal not contacted with or administered the nucleic acid (e.g., interfering RNA). Suitable assays for determining the level of target gene expression include, without limitation, examination of protein or mRNA levels using techniques known to those of skill in the art, such as, e.g., dot blots, Northern blots, in situ hybridization, ELISA, immunoprecipitation, enzyme function, as well as phenotypic assays known to those of skill in the art.

An "effective amount" or "therapeutically effective amount" of an active agent or therapeutic agent such as a therapeutic nucleic acid (e.g., interfering RNA such as an siRNA) is an amount sufficient to produce the desired effect, e.g., an inhibition of expression of a target sequence in comparison to the normal expression level detected in the absence of the nucleic acid (e.g., interfering RNA). Inhibition of expression of a target gene or target sequence is achieved when the value obtained with a nucleic acid such as an interfering RNA (e.g., siRNA) relative to the control is about 95%, 90%, 85%, 80%, 75%, 70%, 65%, 60%, 55%, 50%, 45%, 40%, 35%, 30%, 25%, 20%, 15%, 10%, 5%, or 0%. Suitable assays for measuring expression of a target gene or target sequence include, e.g., examination of protein or RNA levels using techniques known to those of skill in the art such as dot blots, northern blots, in situ hybridization, ELISA, immunoprecipitation, enzyme function, as well as phenotypic assays known to those of skill in the art.

By "decrease," "decreasing," "reduce," or "reducing" of an immune response by a nucleic acid such as an interfering RNA (e.g., siRNA) is intended to mean a detectable decrease of an immune response to a given nucleic acid (e.g., a modified interfering RNA). In some instances, the amount of decrease of an immune response by a nucleic acid such as a modified interfering RNA may be determined relative to the level of an immune response in the presence of an unmodified interfering RNA. As a non-limiting example, a detectable decrease can be about 5%, 10%, 15%, 20%, 25%, 30%, 35%, 40%, 45%, 50%, 55%, 60%, 65%, 70%, 75%, 80%, 85%, 90%, 95%, 100%, or more lower than the immune response detected in the presence of the unmodified interfering RNA. A decrease in the immune response to a nucleic acid (e.g., interfering RNA) is typically measured by a decrease in cytokine production (e.g., IFNγ, IFNα, TNFα, IL-6, IL-8, or IL-12) by a responder cell in vitro or a decrease in cytokine production in the sera of a mammalian subject after administration of the nucleic acid (e.g., interfering RNA).

As used herein, the term "responder cell" refers to a cell, preferably a mammalian cell, that produces a detectable immune response when contacted with an immunostimulatory nucleic acid such as an unmodified interfering RNA (e.g., unmodified siRNA). Exemplary responder cells include, without limitation, dendritic cells, macrophages, peripheral blood mononuclear cells (PBMCs), splenocytes, and the like. Detectable immune responses include, e.g., production of cytokines or growth factors such as TNF-α, IFN-α, IFN-γ, IL-1, IL-2, IL-3, IL-4, IL-5, IL-6, IL-8, IL-10, IL-12, IL-13, TGF, and combinations thereof. Detectable immune responses also include, e.g., induction of interferon-induced protein with tetratricopeptide repeats 1 (IFIT1) mRNA.

The term "nucleic acid" as used herein refers to a polymer containing at least two deoxyribonucleotides or ribonucleotides in either single- or double-stranded form and includes DNA, RNA, and hybrids thereof. DNA may be in the form of, e.g., antisense molecules, plasmid DNA, DNA-DNA duplexes, pre-condensed DNA, PCR products, vectors (P1, PAC, BAC, YAC, artificial chromosomes), expression cassettes, chimeric sequences, chromosomal DNA, or derivatives and combinations of these groups. RNA may be in the form of small interfering RNA (siRNA), Dicer-substrate dsRNA, small hairpin RNA (shRNA), asymmetrical interfering RNA (aiRNA), microRNA (miRNA), mRNA, tRNA, rRNA, tRNA, viral RNA (vRNA), and combinations thereof. Nucleic acids include nucleic acids containing known nucleotide analogs or modified backbone residues or linkages, which are synthetic, naturally occurring, and non-naturally occurring, and which have similar binding properties as the reference nucleic acid. Examples of such analogs include, without limitation, phosphorothioates, phosphoramidates, methyl phosphonates, chiral-methyl phosphonates, 2'-O-methyl ribonucleotides, and peptide-nucleic acids (PNAs). Unless specifically limited, the term encompasses nucleic acids containing known analogues of natural nucleotides that have similar binding properties as the reference nucleic acid. Unless otherwise indicated, a particular nucleic acid sequence also implicitly encompasses conservatively modified variants thereof (e.g., degenerate codon substitutions), alleles, orthologs, SNPs, and complementary sequences as well as the sequence explicitly indicated. Specifically, degenerate codon substitutions may be achieved by generating sequences in which the third position of one or more selected (or all) codons is substituted with mixed-base and/or deoxyinosine residues (Batzer et al., *Nucleic Acid Res.*, 19:5081 (1991); Ohtsuka et al., *J. Biol. Chem.*, 260:2605-2608 (1985); Rossolini et al., *Mol. Cell. Probes*, 8:91-98 (1994)). "Nucleotides" contain a sugar deoxyribose (DNA) or ribose (RNA), a base, and a phosphate group. Nucleotides are linked together through the phosphate groups. "Bases" include purines and pyrimidines, which further include natural compounds adenine, thymine, guanine, cytosine, uracil, inosine, and natural analogs, and synthetic derivatives of purines and pyrimidines, which include, but are not limited to, modifications which place new reactive groups such as, but not limited to, amines, alcohols, thiols, carboxylates, and alkylhalides.

The term "gene" refers to a nucleic acid (e.g., DNA or RNA) sequence that comprises partial length or entire length coding sequences necessary for the production of a polypeptide or precursor polypeptide.

"Gene product," as used herein, refers to a product of a gene such as an RNA transcript or a polypeptide.

The term "lipid" refers to a group of organic compounds that include, but are not limited to, esters of fatty acids and are characterized by being insoluble in water, but soluble in many organic solvents. They are usually divided into at least three classes: (1) "simple lipids," which include fats and oils as well as waxes; (2) "compound lipids," which include phospholipids and glycolipids; and (3) "derived lipids" such as steroids.

The term "lipid particle" includes a lipid formulation that can be used to deliver an active agent or therapeutic agent, such as a nucleic acid (e.g., interfering RNA) to a target site of interest (e.g., cell, tissue, organ, tumor, and the like). In preferred embodiments, the lipid particle of the invention is a nucleic acid-lipid particle, which is typically formed from a cationic lipid, a non-cationic lipid, and optionally a conjugated lipid that prevents aggregation of the particle. In other preferred embodiments, the active agent or therapeutic agent, such as a nucleic acid (e.g., interfering RNA), may be encapsulated in the lipid portion of the particle, thereby protecting it from enzymatic degradation.

As used herein, the term "SNALP" refers to a stable nucleic acid-lipid particle. A SNALP represents a particle made from lipids (e.g., a cationic lipid, a non-cationic lipid, and optionally a conjugated lipid that prevents aggregation of the particle), wherein the nucleic acid (e.g., an interfering RNA) is fully encapsulated within the lipid. In certain instances, SNALP are extremely useful for systemic applications, as they can exhibit extended circulation lifetimes following intravenous (i.v.) injection, they can accumulate at distal sites (e.g., sites physically separated from the administration site), and they can mediate silencing of target gene expression at these distal sites. The nucleic acid may be complexed with a condensing agent and encapsulated within a SNALP as set forth in PCT Publication No. WO 00/03683, the disclosure of which is herein incorporated by reference in its entirety for all purposes.

The lipid particles of the invention (e.g., SNALP) typically have a mean diameter of from about 30 nm to about 150 nm, from about 40 nm to about 150 nm, from about 50 nm to about 150 nm, from about 60 nm to about 130 nm, from about 70 nm to about 110 nm, from about 70 nm to about 100 nm, from about 80 nm to about 100 nm, from about 90 nm to about 100 nm, from about 70 to about 90 nm, from about 80 nm to about 90 nm, from about 70 nm to about 80 nm, or about 30 nm, 35 nm, 40 nm, 45 nm, 50 nm, 55 nm, 60 nm, 65 nm, 70 nm, 75 nm, 80 nm, 85 nm, 90 nm, 95 nm, 100 nm, 105 nm, 110 nm, 115 nm, 120 nm, 125 nm, 130 nm, 135 nm, 140 nm, 145 nm, or 150 nm, and are substantially non-toxic. In addition, nucleic acids, when present in the lipid particles of the present invention, are resistant in aqueous solution to degradation with a nuclease. Nucleic acid-lipid particles and their method of preparation are disclosed in, e.g., U.S. Patent Publication Nos. 20040142025 and 20070042031, the disclosures of which are herein incorporated by reference in their entirety for all purposes.

As used herein, "lipid encapsulated" can refer to a lipid particle that provides an active agent or therapeutic agent, such as a nucleic acid (e.g., an interfering RNA such as an siRNA), with full encapsulation, partial encapsulation, or both. In a preferred embodiment, the nucleic acid (e.g., interfering RNA) is fully encapsulated in the lipid particle (e.g., to form a SNALP or other nucleic acid-lipid particle).

The term "lipid conjugate" refers to a conjugated lipid that inhibits aggregation of lipid particles. Such lipid conjugates include, but are not limited to, PEG-lipid conjugates such as, e.g., PEG coupled to dialkyloxypropyls (e.g., PEG-DAA conjugates), PEG coupled to diacylglycerols (e.g., PEG-DAG conjugates), PEG coupled to cholesterol, PEG coupled to phosphatidylethanolamines, and PEG conjugated to ceramides (see, e.g., U.S. Pat. No. 5,885,613), cationic PEG lipids, polyoxazoline (POZ)-lipid conjugates (e.g., POZ-DAA conjugates; see, e.g., U.S. application Ser. No. 13/006,277, filed Jan. 13, 2011), polyamide oligomers (e.g., ATTA-lipid conjugates), and mixtures thereof. Additional examples of POZ-lipid conjugates are described in PCT Publication No. WO 2010/006282. PEG or POZ can be conjugated directly to the lipid or may be linked to the lipid via a linker moiety. Any linker moiety suitable for coupling the PEG or the POZ to a lipid can be used including, e.g., non-ester containing linker moieties and ester-containing linker moieties. In certain preferred embodiments, non-ester containing linker moieties, such as amides or carbamates, are used. The disclosures of each of the above patent documents are herein incorporated by reference in their entirety for all purposes.

The term "amphipathic lipid" refers, in part, to any suitable material wherein the hydrophobic portion of the lipid material orients into a hydrophobic phase, while the hydrophilic portion orients toward the aqueous phase. Hydrophilic characteristics derive from the presence of polar or charged groups such as carbohydrates, phosphate, carboxylic, sulfato, amino, sulfhydryl, nitro, hydroxyl, and other like groups. Hydrophobicity can be conferred by the inclusion of apolar groups that include, but are not limited to, long-chain saturated and unsaturated aliphatic hydrocarbon groups and such groups substituted by one or more aromatic, cycloaliphatic, or heterocyclic group(s). Examples of amphipathic compounds include, but are not limited to, phospholipids, aminolipids, and sphingolipids.

Representative examples of phospholipids include, but are not limited to, phosphatidylcholine, phosphatidylethanolamine, phosphatidylserine, phosphatidylinositol, phosphatidic acid, palmitoyloleoyl phosphatidylcholine, lysophosphatidylcholine, lysophosphatidylethanolamine, dipalmitoylphosphatidylcholine, dioleoylphosphatidylcholine, distearoylphosphatidylcholine, and dilinoleoylphosphatidylcholine. Other compounds lacking in phosphorus, such as sphingolipid, glycosphingolipid families, diacylglycerols, and β-acyloxyacids, are also within the group designated as amphipathic lipids. Additionally, the amphipathic lipids described above can be mixed with other lipids including triglycerides and sterols.

The term "neutral lipid" refers to any of a number of lipid species that exist either in an uncharged or neutral zwitterionic form at a selected pH. At physiological pH, such lipids include, for example, diacylphosphatidylcholine, diacylphosphatidylethanolamine, ceramide, sphingomyelin, cephalin, cholesterol, cerebrosides, and diacylglycerols.

The term "non-cationic lipid" refers to any amphipathic lipid as well as any other neutral lipid or anionic lipid.

The term "anionic lipid" refers to any lipid that is negatively charged at physiological pH. These lipids include, but are not limited to, phosphatidylglycerols, cardiolipins, diacylphosphatidylserines, diacylphosphatidic acids, N-dodecanoyl phosphatidylethanolamines, N-succinyl phosphatidylethanolamines, N-glutarylphosphatidylethanolamines, lysylphosphatidylglycerols, palmitoyloleoylphosphatidylglycerol (POPG), and other anionic modifying groups joined to neutral lipids.

The term "hydrophobic lipid" refers to compounds having apolar groups that include, but are not limited to, long-chain saturated and unsaturated aliphatic hydrocarbon groups and such groups optionally substituted by one or more aromatic, cycloaliphatic, or heterocyclic group(s). Suitable examples include, but are not limited to, diacylglycerol, dialkylglycerol, N—N-dialkylamino, 1,2-diacryloxy-3-aminopropane, and 1,2-dialkyl-3-aminopropane.

The term "fusogenic" refers to the ability of a lipid particle, such as a SNALP, to fuse with the membranes of a cell. The membranes can be either the plasma membrane or membranes surrounding organelles, e.g., endosome, nucleus, etc.

As used herein, the term "aqueous solution" refers to a composition comprising in whole, or in part, water.

As used herein, the term "organic lipid solution" refers to a composition comprising in whole, or in part, an organic solvent having a lipid.

"Distal site," as used herein, refers to a physically separated site, which is not limited to an adjacent capillary bed, but includes sites broadly distributed throughout an organism.

"Serum-stable" in relation to nucleic acid-lipid particles such as SNALP means that the particle is not significantly degraded after exposure to a serum or nuclease assay that would significantly degrade free DNA or RNA. Suitable assays include, for example, a standard serum assay, a DNAse assay, or an RNAse assay.

"Systemic delivery," as used herein, refers to delivery of lipid particles that leads to a broad biodistribution of an active agent such as an interfering RNA (e.g., siRNA) within an organism. Some techniques of administration can lead to the systemic delivery of certain agents, but not others. Systemic delivery means that a useful, preferably therapeutic, amount of an agent is exposed to most parts of the body. To obtain broad biodistribution generally requires a blood lifetime such that the agent is not rapidly degraded or cleared (such as by first pass organs (liver, lung, etc.) or by rapid, nonspecific cell binding) before reaching a disease site distal to the site of administration. Systemic delivery of lipid particles can be by any means known in the art including, for example, intravenous, subcutaneous, and intraperitoneal. In a preferred embodiment, systemic delivery of lipid particles is by intravenous delivery.

"Local delivery," as used herein, refers to delivery of an active agent such as an interfering RNA (e.g., siRNA) directly to a target site within an organism. For example, an agent can be locally delivered by direct injection into a disease site such as a tumor, other target site such as a site of inflammation, or a target organ such as the liver, heart, pancreas, kidney, and the like.

The term "mammal" refers to any mammalian species such as a human, mouse, rat, dog, cat, hamster, guinea pig, rabbit, livestock, and the like.

The term "cancer" refers to any member of a class of diseases characterized by the uncontrolled growth of aberrant cells. The term includes all known cancers and neoplastic conditions, whether characterized as malignant, benign, soft tissue, or solid, and cancers of all stages and grades including pre- and post-metastatic cancers. Examples of different types of cancer include, but are not limited to, liver cancer, lung cancer, colon cancer, rectal cancer, anal cancer, bile duct cancer, small intestine cancer, stomach (gastric) cancer, esophageal cancer; gallbladder cancer, pancreatic cancer, appendix cancer, breast cancer, ovarian cancer; cervical cancer, prostate cancer, renal cancer (e.g., renal cell carcinoma), cancer of the central nervous system, glioblastoma, skin cancer, lymphomas, choriocarcinomas, head and neck cancers, osteogenic sarcomas, and blood cancers. Non-limiting examples of specific types of liver cancer include hepatocellular carcinoma (HCC), secondary liver cancer (e.g., caused by metastasis of some other non-liver cancer cell type), and hepatoblastoma. As used herein, a "tumor" comprises one or more cancerous cells.

III. Novel Cationic Lipids

The present invention provides, inter alia, novel cationic (amino) lipids that can advantageously be used in the lipid particles described herein for the in vitro and/or in vivo delivery of therapeutic agents such as nucleic acids to cells. The novel cationic lipids of the invention have the structures set forth in Formulas herein, and include the (R) and/or (S) enantiomers thereof.

In some embodiments, a lipid of the present invention comprises a racemic mixture. In other embodiments, a lipid of the present invention comprises a mixture of one or more diastereomers. In certain embodiments, a lipid of the present invention is enriched in one enantiomer, such that the lipid comprises at least about 55%, 60%, 65%, 70%, 75%, 80%, 85%, 90%, or 95% enantiomeric excess. In certain other embodiments, a lipid of the present invention is enriched in one diastereomer, such that the lipid comprises at least about 55%, 60%, 65%, 70%, 75%, 80%, 85%, 90%, or 95% diastereomeric excess. In certain additional embodiments, a lipid of the present invention is chirally pure (e.g., comprises a single optical isomer). In further embodiments, a lipid of the present invention is enriched in one optical isomer (e.g., an optically active isomer), such that the lipid comprises at least about 55%, 60%, 65%, 70%, 75%, 80%, 85%, 90%, or 95% isomeric excess. The present invention provides the synthesis of the cationic lipids of Formula I-III as a racemic mixture or in optically pure form.

The terms "cationic lipid" and "amino lipid" are used interchangeably herein to include those lipids and salts thereof having one, two, three, or more fatty acid or fatty alkyl chains and a pH-titratable amino head group (e.g., an alkylamino or dialkylamino head group). The cationic lipid is typically protonated (i.e., positively charged) at a pH below the $pK_a$ of the cationic lipid and is substantially neutral at a pH above the $pK_a$. The cationic lipids of the invention may also be termed titratable cationic lipids.

The term "salts" includes any anionic and cationic complex, such as the complex formed between a cationic lipid disclosed herein and one or more anions. Non-limiting examples of anions include inorganic and organic anions, e.g., hydride, fluoride, chloride, bromide, iodide, oxalate (e.g., hemioxalate), phosphate, phosphonate, hydrogen phosphate, dihydrogen phosphate, oxide, carbonate, bicarbonate, nitrate, nitrite, nitride, bisulfite, sulfide, sulfite, bisulfate, sulfate, thiosulfate, hydrogen sulfate, borate, formate, acetate, benzoate, citrate, tartrate, lactate, acrylate, polyacrylate, fumarate, maleate, itaconate, glycolate, gluconate, malate, mandelate, tiglate, ascorbate, salicylate, polymethacrylate, perchlorate, chlorate, chlorite, hypochlorite, bromate, hypobromite, iodate, an alkylsulfonate, an arylsulfonate, arsenate, arsenite, chromate, dichromate, cyanide, cyanate, thiocyanate, hydroxide, peroxide, permanganate, and mixtures thereof. In particular embodiments, the salts of the cationic lipids disclosed herein are crystalline salts.

The term "alkyl" includes a straight chain or branched, noncyclic or cyclic, saturated aliphatic hydrocarbon containing from 1 to 24 carbon atoms. Representative saturated straight chain alkyls include, but are not limited to, methyl, ethyl, n-propyl, n-butyl, n-pentyl, n-hexyl, and the like, while saturated branched alkyls include, without limitation, isopropyl, sec-butyl, isobutyl, tert-butyl, isopentyl, and the like. Representative saturated cyclic alkyls include, but are not limited to, the $C_{3-8}$ cycloalkyls described herein, while unsaturated cyclic alkyls include, without limitation, the $C_{3-8}$ cycloalkenyls described herein.

The term "heteroalkyl," includes a straight chain or branched, noncyclic or cyclic, saturated aliphatic hydrocarbon as defined above having from about 1 to about 5 heteroatoms (i.e., 1, 2, 3, 4, or 5 heteroatoms) such as, for example, O, N, Si, and/or S, wherein the nitrogen and sulfur atoms may optionally be oxidized and the nitrogen heteroatom may optionally be quaternized. The heteroalkyl group can be attached to the remainder of the molecule through a carbon atom or a heteroatom.

The term "cyclic alkyl" includes any of the substituted or unsubstituted cycloalkyl, heterocycloalkyl, cycloalkenyl, and heterocycloalkenyl groups described below.

The term "cycloalkyl" includes a substituted or unsubstituted cyclic alkyl group having from about 3 to about 8 carbon atoms (i.e., 3, 4, 5, 6, 7, or 8 carbon atoms) as ring vertices. Preferred cycloalkyl groups include those having from about 3 to about 6 carbon atoms as ring vertices. Examples of $C_{3-8}$ cycloalkyl groups include, but are not limited to, cyclopropyl, methyl-cyclopropyl, dimethyl-cyclopropyl, cyclobutyl, methyl-cyclobutyl, cyclopentyl, methyl-cyclopentyl, cyclohexyl, methyl-cyclohexyl, dimethyl-cyclohexyl, cycloheptyl, and cyclooctyl, as well as other substituted $C_{3-8}$ cycloalkyl groups.

The term "heterocycloalkyl" includes a substituted or unsubstituted cyclic alkyl group as defined above having from about 1 to about 3 heteroatoms as ring members selected from the group consisting of O, N, Si and S, wherein the nitrogen and sulfur atoms may optionally be oxidized and the nitrogen heteroatom may optionally be quaternized. The heterocycloalkyl group can be attached to the remainder of the molecule through a carbon atom or a heteroatom.

The term "cycloalkenyl" includes a substituted or unsubstituted cyclic alkenyl group having from about 3 to about 8 carbon atoms (i.e., 3, 4, 5, 6, 7, or 8 carbon atoms) as ring vertices. Preferred cycloalkenyl groups are those having from about 3 to about 6 carbon atoms as ring vertices. Examples of $C_{3-8}$ cycloalkenyl groups include, but are not limited to, cyclopropenyl, methyl-cyclopropenyl, dimethyl-cyclopropenyl, cyclobutenyl, cyclopentenyl, cyclohexenyl, cycloheptenyl, and cyclooctenyl, as well as other substituted $C_{3-8}$ cycloalkenyl groups.

The term "heterocycloalkenyl" includes a substituted or unsubstituted cyclic alkenyl group as defined above having from about 1 to about 3 heteroatoms as ring members selected from the group consisting of O, N, Si and S, wherein the nitrogen and sulfur atoms may optionally be oxidized and the nitrogen heteroatom may optionally be quaternized. The heterocycloalkenyl group can be attached to the remainder of the molecule through a carbon atom or a heteroatom.

The term "alkoxy" includes a group of the formula alkyl-O—, wherein "alkyl" has the previously given definition. Non-limiting examples of alkoxy groups include methoxy, ethoxy, n-propoxy, iso-propoxy, n-butoxy, iso-butoxy, sec-butoxy and tert-butoxy.

The term "alkenyl" includes an alkyl, as defined above, containing at least one double bond between adjacent carbon atoms. Alkenyls include both cis and trans isomers. Representative straight chain and branched alkenyls include, but are not limited to, ethylenyl, propylenyl, 1-butenyl, 2-butenyl, isobutylenyl, 1-pentenyl, 2-pentenyl, 3-methyl-1-butenyl, 2-methyl-2-butenyl, 2,3-dimethyl-2-butenyl, and the like. Representative cyclic alkenyls are described above.

The term "alkynyl" includes any alkyl or alkenyl, as defined above, which additionally contains at least one triple bond between adjacent carbons. Representative straight chain and branched alkynyls include, without limitation, acetylenyl, propynyl, 1-butynyl, 2-butynyl, 1-pentynyl, 2-pentynyl, 3-methyl-1 butynyl, and the like.

The term "aryl" includes a polyunsaturated, typically aromatic, hydrocarbon group which can be a single ring or multiple rings (up to three rings) which are fused together or linked covalently, and which optionally carries one or more substituents, such as, for example, halogen, trifluoromethyl, amino, alkyl, alkoxy, alkylcarbonyl, cyano, carbamoyl, alkoxycarbamoyl, methylenedioxy, carboxy, alkoxycarbonyl, aminocarbonyl, alkylaminocarbonyl, dialkylaminocarbonyl, hydroxy, nitro, and the like. Non-limiting examples of unsubstituted aryl groups include phenyl, naphthyl, and biphenyl. Examples of substituted aryl groups include, but are not limited to, phenyl, chlorophenyl, trifluoromethyl-phenyl, chlorofluorophenyl, and aminophenyl.

The terms "alkylthio," "alkylsulfonyl," "alkylsulfinyl," and "arylsulfonyl" include groups having the formula —S—$R^i$, —S(O)$_2$—$R^i$, —S(O)—$R^i$ and —S(O)$_2R^j$, respectively, wherein $R^i$ is an alkyl group as previously defined and $R^j$ is an aryl group as previously defined.

The terms "alkenyloxy" and "alkynyloxy" include groups having the formula —O—$R^i$, wherein $R^i$ is an alkenyl or alkynyl group, respectively.

The terms "alkenylthio" and "alkynylthio" include groups having the formula —S—$R^k$, wherein $R^k$ is an alkenyl or alkynyl group, respectively.

The term "alkoxycarbonyl" includes a group having the formula —C(O)O—$R^i$, wherein $R^i$ is an alkyl group as defined above and wherein the total number of carbon atoms refers to the combined alkyl and carbonyl moieties.

The term "acyl" includes any alkyl, alkenyl, or alkynyl wherein the carbon at the point of attachment is substituted with an oxo group, as defined below. The following are non-limiting examples of acyl groups: —C(=O)alkyl, —C(=O)alkenyl, and —C(=O)alkynyl.

The term "heterocycle" includes a 5- to 7-membered monocyclic, or 7- to 10-membered bicyclic, heterocyclic ring which is either saturated, unsaturated, or aromatic, and which contains one, two, three, or more heteroatoms independently selected from nitrogen (N), oxygen (O), and sulfur (S), and wherein the nitrogen and sulfur heteroatoms may be optionally oxidized, and the nitrogen heteroatom may be optionally quaternized, including bicyclic rings in which any of the above heterocycles are fused to a benzene ring. The heterocycle may be attached via any heteroatom or carbon atom. Heterocycles include, but are not limited to, heteroaryls as defined below, as well as morpholinyl, pyrrolidinonyl, pyrrolidinyl, piperidinyl, piperizinyl, hydantoinyl, valerolactamyl, oxiranyl, oxetanyl, tetrahydrofuranyl, tetrahydropyranyl, tetrahydropyridinyl, tetrahydropyrimidinyl, tetrahydrothiophenyl, tetrahydrothiopyranyl, tetrahydropyrimidinyl, tetrahydrothiophenyl, tetrahydrothiopyranyl, and the like.

The term "heteroaryl" includes an aromatic 5- to 10-membered heterocycle which contains one, two, three, or more heteroatoms selected from nitrogen (N), oxygen (O), and sulfur (S). The heteroaryl can be substituted on one or more carbon atoms with substituents such as, for example, halogen, alkyl, alkoxy, cyano, haloalkyl (e.g., trifluoromethyl), heterocyclyl (e.g., morpholinyl or pyrrolidinyl), and the like. Non-limiting examples of heteroaryls include pyridinyl and furanyl.

The term "halogen" includes fluoro, chloro, bromo, and iodo.

The terms "optionally substituted alkyl," "optionally substituted cyclic alkyl," "optionally substituted alkenyl," "optionally substituted alkynyl," "optionally substituted acyl," and "optionally substituted heterocycle" mean that, when substituted, at least one hydrogen atom is replaced with a substituent. In the case of an "oxo" substituent (=O), two hydrogen atoms are replaced. Non-limiting examples of substituents include oxo, halogen, heterocycle, —CN, —OR$^x$, —NR$^x$R$^y$, —NR$^x$C(=O)R$^y$, —NR$^x$SO$_2$R$^y$, —C(=O)R$^x$, —C(=O)OR$^x$, —C(=O)NR$^x$R$^y$, —SO$_n$R$^x$, and —SO$_n$NR$^x$R$^y$, wherein n is 0, 1, or 2, R$^x$ and R$^y$ are the same or different and are independently hydrogen, alkyl, or heterocycle, and each of the alkyl and heterocycle substituents may be further substituted with one or more of oxo, halogen, —OH, —CN, alkyl, —OR$^x$, heterocycle, —NR$^x$R$^y$, —NR$^x$C(=O)R$^y$, —NR$^x$SO$_2$R$^y$, —C(=O)R$^x$, —C(=O)OR$^x$, —C(=O)NR$^x$R$^y$, —SO$_n$R$^x$, and —SO$_n$-NR$^x$R$^y$. The term "optionally substituted," when used before a list of substituents, means that each of the substituents in the list may be optionally substituted as described herein.

In one aspect, the present invention provides a cationic lipid of Formula I having the following structure:

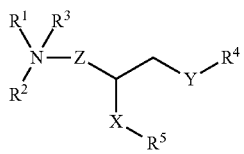

(I)

or salts thereof, wherein:

$R^1$ and $R^2$ are either the same or different and are independently hydrogen (H) or an optionally substituted $C_1$-$C_6$ alkyl, $C_2$-$C_6$ alkenyl, or $C_2$-$C_6$ alkynyl, or $R^1$ and $R^2$ may join to form an optionally substituted heterocyclic ring;

$R^3$ is either absent or is hydrogen (H) or a $C_1$-$C_6$ alkyl to provide a quaternary amine;

$R^4$ and $R^5$ are either the same or different and are independently an optionally substituted $C_{10}$-$C_{24}$ alkyl, $C_{10}$-$C_{24}$ alkenyl, $C_{10}$-$C_{24}$ alkynyl, or $C_{10}$-$C_{24}$ acyl, wherein at least one of $R^4$ and $R^5$ comprises at least 1, 2, 3, 4, 5, 6, or more optionally substituted cyclic alkyl groups (e.g., 1-2, 1-3, 1-4, 1-5, 1-6, 2-3, 2-4, 2-5, or 2-6 optionally substituted cyclic alkyl groups);

X and Y are either the same or different and are independently O, S, $N(R^6)$, C(O), C(O)O, OC(O), $C(O)N(R^6)$, $N(R^6)C(O)$, $OC(O)N(R^6)$, $N(R^6)C(O)O$, C(O)S, C(S) O, S(O), S(O)(O), C(S), or an optionally substituted heterocyclic ring, wherein $R^6$ is hydrogen (H) or an optionally substituted $C_1$-$C_{10}$ alkyl, $C_2$-$C_{10}$ alkenyl, or $C_2$-$C_{10}$ alkynyl; and Z is either absent or is an optionally substituted $C_1$-$C_6$ alkyl, $C_2$-$C_6$ alkenyl, or $C_2$-$C_6$ alkynyl.

In some embodiments, $R^1$ and $R^2$ are each independently hydrogen (H) or an optionally substituted $C_1$-$C_2$ alkyl, $C_1$-$C_3$ alkyl, $C_1$-$C_4$ alkyl, $C_1$-$C_5$ alkyl, $C_2$-$C_3$ alkyl, $C_2$-$C_4$ alkyl, $C_2$-$C_5$ alkyl, $C_2$-$C_6$ alkyl, $C_3$-$C_4$ alkyl, $C_3$-$C_5$ alkyl, $C_3$-$C_6$ alkyl, $C_4$-$C_5$ alkyl, $C_4$-$C_6$ alkyl, $C_5$-$C_6$ alkyl, $C_2$-$C_3$ alkenyl, $C_2$-$C_4$ alkenyl, $C_2$-$C_5$ alkenyl, $C_2$-$C_6$ alkenyl, $C_3$-$C_4$ alkenyl, $C_3$-$C_5$ alkenyl, $C_3$-$C_6$ alkenyl, $C_4$-$C_5$ alkenyl, $C_4$-$C_6$ alkenyl, $C_5$-$C_6$ alkenyl, $C_2$-$C_3$ alkynyl, $C_2$-$C_4$ alkynyl, $C_2$-$C_5$ alkynyl, $C_2$-$C_6$ alkynyl, $C_3$-$C_4$ alkynyl, $C_3$-$C_5$ alkynyl, $C_3$-$C_6$ alkynyl, $C_4$-$C_5$ alkynyl, $C_4$-$C_6$ alkynyl, or $C_5$-$C_6$ alkynyl. In particular embodiments, $R^1$ and $R^2$ are both methyl groups, both ethyl groups, or a combination of one methyl group and one ethyl group. In certain instances, $R^3$ is absent when the pH is above the $pK_a$ of the cationic lipid and $R^3$ is hydrogen (H) when the pH is below the $pK_a$ of the cationic lipid such that the amino head group is protonated. In certain other instances, $R^3$ is an optionally substituted $C_1$-$C_2$ alkyl, $C_1$-$C_3$ alkyl, $C_1$-$C_4$ alkyl, $C_1$-$C_5$ alkyl, $C_2$-$C_3$ alkyl, $C_2$-$C_4$ alkyl, $C_2$-$C_5$ alkyl, $C_2$-$C_6$ alkyl, $C_3$-$C_4$ alkyl, $C_3$-$C_5$ alkyl, $C_3$-$C_6$ alkyl, $C_4$-$C_5$ alkyl, $C_4$-$C_6$ alkyl, or $C_5$-$C_6$ alkyl to provide a quaternary amine.

In certain embodiments, $R^1$ and $R^2$ are joined to form an optionally substituted heterocyclic ring comprising 1, 2, 3, 4, 5, 6, or more carbon atoms and 1, 2, 3, 4, or more heteroatoms such as nitrogen (N), oxygen (O), sulfur (S), and mixtures thereof. In some embodiments, the optionally substituted heterocyclic ring comprises from 2 to 5 carbon atoms and from 1 to 3 heteroatoms such as nitrogen (N), oxygen (O), and/or sulfur (S). In certain embodiments, the heterocyclic ring comprises an optionally substituted imidazole, triazole (e.g., 1,2,3-triazole, 1,2,4-triazole), pyrazole, thiazole, pyrrole, furan, oxazole, isoxazole, oxazoline, oxazolidine, oxadiazole, tetrazole, and the like. In some instances, the optionally substituted heterocyclic ring comprises 5 carbon atoms and 1 nitrogen atom, wherein the heterocyclic ring can be substituted with a substituent such as a hydroxyl (—OH) group at the ortho, meta, and/or para positions. In certain instances, the heterocyclic ring comprises an optionally substituted imidazole group.

In other embodiments, $R^6$ is hydrogen (H) or an optionally substituted $C_1$-$C_2$ alkyl, $C_1$-$C_3$ alkyl, $C_1$-$C_4$ alkyl, $C_1$-$C_5$ alkyl, $C_1$-$C_6$ alkyl, $C_1$-$C_7$ alkyl, $C_1$-$C_8$ alkyl, $C_1$-$C_9$ alkyl, $C_2$-$C_3$ alkyl, $C_2$-$C_4$ alkyl, $C_2$-$C_5$ alkyl, $C_2$-$C_6$ alkyl, $C_2$-$C_7$ alkyl, $C_2$-$C_8$ alkyl, $C_2$-$C_9$ alkyl, $C_2$-$C_{10}$ alkyl, $C_3$-$C_4$ alkyl, $C_3$-$C_5$ alkyl, $C_3$-$C_6$ alkyl, $C_3$-$C_7$ alkyl, $C_3$-$C_8$ alkyl, $C_3$-$C_9$ alkyl, $C_3$-$C_{10}$ alkyl, $C_4$-$C_5$ alkyl, $C_4$-$C_6$ alkyl, $C_4$-$C_7$ alkyl, $C_4$-$C_8$ alkyl, $C_4$-$C_9$ alkyl, $C_4$-$C_{10}$ alkyl, $C_5$-$C_6$ alkyl, $C_5$-$C_7$ alkyl, $C_5$-$C_8$ alkyl, $C_5$-$C_9$ alkyl, $C_5$-$C_{10}$ alkyl, $C_6$-$C_7$ alkyl, $C_6$-$C_8$ alkyl, $C_6$-$C_9$ alkyl, $C_6$-$C_{10}$ alkyl, $C_7$-$C_8$ alkyl, $C_7$-$C_9$ alkyl, $C_7$-$C_{10}$ alkyl, $C_8$-$C_9$ alkyl, $C_8$-$C_{10}$ alkyl, $C_9$-$C_{10}$ alkyl, $C_2$-$C_3$ alkenyl, $C_2$-$C_4$ alkenyl, $C_2$-$C_5$ alkenyl, $C_2$-$C_6$ alkenyl, $C_2$-$C_7$ alkenyl, $C_2$-$C_8$ alkenyl, $C_2$-$C_9$ alkenyl, $C_3$-$C_4$ alkenyl, $C_3$-$C_5$ alkenyl, $C_3$-$C_6$ alkenyl, $C_3$-$C_7$ alkenyl, $C_3$-$C_8$ alkenyl, $C_3$-$C_9$ alkenyl, $C_3$-$C_{10}$ alkenyl, $C_4$-$C_5$ alkenyl, $C_4$-$C_6$ alkenyl, $C_4$-$C_7$ alkenyl, $C_4$-$C_8$ alkenyl, $C_4$-$C_9$ alkenyl, $C_4$-$C_{10}$ alkenyl, $C_5$-$C_6$ alkenyl, $C_5$-$C_7$ alkenyl, $C_5$-$C_8$ alkenyl, $C_5$-$C_9$ alkenyl, $C_5$-$C_{10}$ alkenyl, $C_6$-$C_7$ alkenyl, $C_6$-$C_8$ alkenyl, $C_6$-$C_9$ alkenyl, $C_6$-$C_{10}$ alkenyl, $C_7$-$C_8$ alkenyl, $C_7$-$C_9$ alkenyl, $C_7$-$C_{10}$ alkenyl, $C_8$-$C_9$ alkenyl, $C_8$-$C_{10}$ alkenyl, $C_9$-$C_{10}$ alkenyl, $C_2$-$C_3$ alkynyl, $C_2$-$C_4$ alkynyl, $C_2$-$C_5$ alkynyl, $C_2$-$C_6$ alkynyl, $C_2$-$C_7$ alkynyl, $C_2$-$C_8$ alkynyl, $C_2$-$C_9$ alkynyl, $C_3$-$C_4$ alkynyl, $C_3$-$C_5$ alkynyl, $C_3$-$C_6$ alkynyl, $C_3$-$C_7$ alkynyl, $C_3$-$C_8$ alkynyl, $C_3$-$C_9$ alkynyl, $C_3$-$C_{10}$ alkynyl, $C_4$-$C_5$ alkynyl, $C_4$-$C_6$ alkynyl, $C_4$-$C_7$ alkynyl, $C_4$-$C_8$ alkynyl, $C_4$-$C_9$ alkynyl, $C_4$-$C_{10}$ alkynyl, $C_5$-$C_6$ alkynyl, $C_5$-$C_7$ alkynyl, $C_5$-$C_8$ alkynyl, $C_5$-$C_9$ alkynyl, $C_5$-$C_{10}$ alkynyl, $C_6$-$C_7$ alkynyl, $C_6$-$C_8$ alkynyl, $C_6$-$C_9$ alkynyl, $C_6$-$C_{10}$ alkynyl, $C_7$-$C_8$ alkynyl, $C_7$-$C_9$ alkynyl, $C_7$-$C_{10}$ alkynyl, $C_8$-$C_9$ alkynyl, $C_8$-$C_{10}$ alkynyl, or $C_9$-$C_{10}$ alkynyl. In one particular embodiment, $R^6$ is selected from the group consisting of hydrogen (H), a $C_1$ alkyl (methyl) group, and a $C_2$, $C_3$, $C_4$, $C_5$, $C_6$, $C_7$, $C_8$, $C_9$, and $C_{10}$ alkyl, alkenyl, and alkynyl group.

In one embodiment, X and Y are independently selected from the group consisting of O, C(O)O, $C(O)N(R^6)$, $N(R^6)$ C(O)O, and C(O)S. In one particular embodiment, X and Y are both oxygen (O). In another particular embodiment, at least one of (e.g., both) X and Y is $N(R^6)C(O)O$ and each $R^6$ is independently hydrogen (H), a methyl group, or a $C_2$, $C_3$, $C_4$, $C_5$, $C_6$, $C_7$, $C_8$, $C_9$, or $C_{10}$ alkyl, alkenyl, or alkynyl group. In certain other embodiments, at least one of (e.g., both) X and Y is an independently selected optionally substituted heterocyclic ring. In particular embodiments, the heterocyclic ring comprises 1, 2, 3, 4, 5, 6, or more carbon atoms and 1, 2, 3, 4, or more heteroatoms such as nitrogen (N), oxygen (O), sulfur (S), and mixtures thereof. In some embodiments, the optionally substituted heterocyclic ring comprises from 2 to 5 carbon atoms and from 1 to 3 heteroatoms such as nitrogen (N), oxygen (O), and/or sulfur (S). In certain embodiments, the heterocyclic ring comprises an optionally substituted imidazole, triazole (e.g., 1,2,3-triazole, 1,2,4-triazole), pyrazole, thiazole, pyrrole, furan, oxazole, isoxazole, oxazoline, oxazolidine, oxadiazole, tetrazole, and the like.

In certain embodiments, $R^4$ and $R^5$ are independently an optionally substituted $C_{12}$-$C_{24}$, $C_{12}$-$C_{22}$, $C_{12}$-$C_{20}$, $C_{14}$-$C_{24}$, $C_{14}$-$C_{22}$, $C_{14}$-$C_{20}$, $C_{16}$-$C_{24}$, $C_{16}$-$C_{22}$, or $C_{16}$-$C_{20}$ alkyl, alkenyl, alkynyl, or acyl group (i.e., a $C_{12}$, $C_{13}$, $C_{14}$, $C_{15}$, $C_{16}$, $C_{17}$, $C_{18}$, $C_{19}$, $C_{20}$, $C_{21}$, $C_{22}$, $C_{23}$, or $C_{2-4}$ alkyl, alkenyl, alkynyl, or acyl group), wherein at least one or more of (e.g., both) $R^4$ and $R^5$ independently comprises at least 1, 2, 3, 4, 5, or 6 optionally substituted cyclic alkyl groups (e.g., 1-2, 1-3, 1-4, 1-5, 1-6, 2-3, 2-4, 2-5, or 2-6 optionally substituted cyclic alkyl groups). In particular embodiments, the at least 1, 2, 3, 4, 5, or 6 optionally substituted cyclic alkyl groups present in $R^4$ and/or $R^5$ are independently selected from the group consisting of an optionally substituted saturated cyclic alkyl group, an optionally substituted unsaturated cyclic alkyl group, and combinations thereof. In certain instances, the optionally substituted saturated cyclic alkyl group comprises an optionally substituted $C_{3-8}$ cycloalkyl group (e.g., cyclopropyl, cyclobutyl, cyclopentyl, cyclohexyl, cycloheptyl, cyclooctyl, etc.). In preferred embodiments, the optionally substituted saturated cyclic alkyl group comprises a cyclopropyl group, optionally containing one or more substituents and/or heteroatoms. In other instances, the optionally substituted unsaturated cyclic alkyl group comprises an optionally substituted $C_{3-8}$ cycloalkenyl group (e.g., cyclopropenyl, cyclobutenyl, cyclopentenyl, cyclohexenyl, cycloheptenyl, cyclooctenyl, etc.). In particular embodiments, $R^4$ and $R^5$ are the same length (e.g., $C_{12}$-$C_{20}$ or $C_{18}$ alkyl chains) and contain the same number and type of cyclic alkyl group (e.g., one, two, or three $C_{3-8}$ cycloalkyl groups such as one, two, or three cyclopropyl groups on each of $R^4$ and $R^5$).

In certain other embodiments, one of $R^4$ or $R^5$ comprises at least 1, 2, 3, 4, 5, or 6 sites of unsaturation (e.g., 1-2, 1-3, 1-4, 1-5, 1-6, 2-3, 2-4, 2-5, or 2-6 sites of unsaturation) or a substituted alkyl or acyl group, and the other side-chain comprises at least 1, 2, 3, 4, 5, or 6 optionally substituted cyclic alkyl groups (e.g., 1-2, 1-3, 1-4, 1-5, 1-6, 2-3, 2-4, 2-5, or 2-6 optionally substituted cyclic alkyl groups). In embodiments where one of $R^4$ or $R^5$ comprises at least 1, 2, 3, 4, 5, or 6 sites of unsaturation, the unsaturated side-chain may comprise a dodecenyl moiety, a tetradecenyl (e.g., myristoleyl) moiety, a hexadecenyl (e.g., palmitoleyl) moiety, an octadecenyl (e.g., oleyl) moiety, an icosenyl moiety, a dodecadienyl moiety, a tetradecadienyl moiety, a hexadecadienyl moiety, an octadecadienyl moiety, an icosadienyl moiety, a dodecatrienyl moiety, a tetradectrienyl moiety, a hexadecatrienyl moiety, an octadecatrienyl moiety, an icosatrienyl moiety, or an acyl derivative thereof (e.g., oleoyl, linoleoyl, linolenoyl, γ-linolenoyl, etc.). In some instances, the octadecadienyl moiety is a linoleyl moiety. In other instances, the octadecatrienyl moiety is a linolenyl moiety or a γ-linolenyl moiety. In embodiments where one of $R^4$ or $R^5$ comprises a branched alkyl or acyl group (e.g., a substituted alkyl or acyl group), the branched alkyl or acyl group may comprise a $C_{12}$-$C_{24}$ alkyl or acyl having at least 1-6 (e.g., 1, 2, 3, 4, 5, 6, or more) $C_1$-$C_6$ alkyl substituents. In particular embodiments, the branched alkyl or acyl group comprises a $C_{12}$-$C_{20}$ or $C_{14}$-$C_{22}$ alkyl or acyl with 1-6 (e.g., 1, 2, 3, 4, 5, 6) $C_1$-$C_4$ alkyl (e.g., methyl, ethyl, propyl, or butyl) substituents. In some embodiments, the branched alkyl group comprises a phytanyl (3,7,11,15-tetramethyl-hexadecanyl) moiety and the branched acyl group comprises a phytanoyl (3,7,11,15-tetramethyl-hexadecanoyl) moiety.

In particular embodiments, $R^4$ and $R^5$ are both independently selected $C_{12}$-$C_{20}$ alkyl groups (i.e., $C_{12}$, $C_{13}$, $C_{14}$, $C_{15}$, $C_{16}$, $C_{17}$, $C_{18}$, $C_{19}$, or $C_{20}$ alkyl groups) having at least 1, 2, 3, 4, 5, or 6 optionally substituted cyclic alkyl groups (e.g., 1-2, 1-3, 1-4, 1-5, 1-6, 2-3, 2-4, 2-5, or 2-6 optionally substituted cyclic alkyl groups). In preferred embodiments, $R^4$ and $R^5$ are both $C_{18}$ alkyl groups having at least one, two, three, or more optionally substituted cyclic alkyl groups such as, for example, an optionally substituted $C_{3-8}$ cycloalkyl group (e.g., a cyclopropyl group, optionally containing one or more substituents and/or heteroatoms). In certain embodiments, each of the optionally substituted cyclic alkyl groups is independently selected and can be the same cyclic alkyl group (e.g., all cyclopropyl groups) or different cyclic alkyl groups (e.g., cyclopropyl and other cycloalkyl, heterocycloalkyl, cycloalkenyl, and/or heterocycloalkenyl groups).

In preferred embodiments, the optionally substituted cyclic alkyl groups present in $R^4$ and/or $R^5$ are located at the site(s) of unsaturation in the corresponding unsaturated side-chain. As a non-limiting example, one or both of $R^4$ and $R^5$ are $C_{18}$ alkyl groups having 1, 2, or 3 optionally substituted cyclic alkyl groups, wherein the optionally substituted cyclic alkyl groups (e.g., independently selected cyclopropyl groups) are located at one or more (e.g., all) of the sites of unsaturation present in a corresponding linoleyl moiety, linolenyl moiety, or γ-linolenyl moiety.

In alternative embodiments to the cationic lipid of Formula I, $R^4$ and $R^5$ are different and are independently an optionally substituted $C_1$-$C_{24}$ alkyl, $C_2$-$C_{24}$ alkenyl, $C_2$-$C_{24}$ alkynyl, or $C_1$-$C_{24}$ acyl, wherein at least one of $R^4$ and $R^5$ comprises at least one optionally substituted cyclic alkyl group. In certain embodiments, $R^4$ and $R^5$ are different and are independently an optionally substituted $C_4$-$C_{20}$ alkyl, $C_4$-$C_{20}$ alkenyl, $C_4$-$C_{20}$ alkynyl, or $C_4$-$C_{20}$ acyl. In some instances, $R^4$ is an optionally substituted $C_{12}$-$C_{24}$ alkyl, $C_{12}$-$C_{24}$ alkenyl, $C_{12}$-$C_{24}$ alkynyl, or $C_{12}$-$C_{24}$ acyl, and $R^5$ is an optionally substituted $C_4$-$C_{10}$ alkyl, $C_4$-$C_{10}$ alkenyl, $C_4$-$C_{10}$ alkynyl, or $C_4$-$C_{10}$ acyl. In other instances, $R^4$ is an optionally substituted $C_{12}$-$C_{20}$ or $C_{14}$-$C_{22}$ alkyl, $C_{12}$-$C_{20}$ or $C_{14}$-$C_{22}$ alkenyl, $C_{12}$-$C_{20}$ or $C_{14}$-$C_{22}$ alkynyl, or $C_{12}$-$C_{20}$ or $C_{14}$-$C_{22}$ acyl, and $R^5$ is an optionally substituted $C_4$-$C_8$ or $C_6$ alkyl, $C_4$-$C_8$ or $C_6$ alkenyl, $C_4$-$C_8$ or $C_6$ alkynyl, or $C_4$-$C_8$ or $C_6$ acyl. In certain instances, $R^4$ is an optionally substituted $C_4$-$C_{10}$ alkyl, $C_4$-$C_{10}$ alkenyl, $C_4$-$C_{10}$ alkynyl, or $C_4$-$C_{10}$ acyl, and $R^5$ is an optionally substituted $C_{12}$-$C_{24}$ alkyl, $C_{12}$-$C_{24}$ alkenyl, $C_{12}$-$C_{24}$ alkynyl, or $C_{12}$-$C_{24}$ acyl. In certain other instances, $R^4$ is an optionally substituted $C_4$-$C_8$ or $C_6$ alkyl, $C_4$-$C_8$ or $C_6$ alkenyl, $C_4$-$C_8$ or $C_6$ alkynyl, or $C_4$-$C_8$ or $C_6$ acyl, and $R^5$ is an optionally substituted $C_{12}$-$C_{20}$ or $C_{14}$-$C_{22}$ alkyl, $C_{12}$-$C_{20}$ or $C_{14}$-$C_{22}$ alkenyl, $C_{12}$-$C_{20}$ or $C_{14}$-$C_{22}$ alkynyl, or $C_{12}$-$C_{20}$ or $C_{14}$-$C_{22}$ acyl. In particular embodiments, one or more of the optionally substituted cyclic alkyl groups present in $R^4$ and/or $R^5$ are as described above.

In some groups of embodiments to the cationic lipid of Formula I, $R^4$ and $R^5$ are either the same or different and are independently selected from the group consisting of:

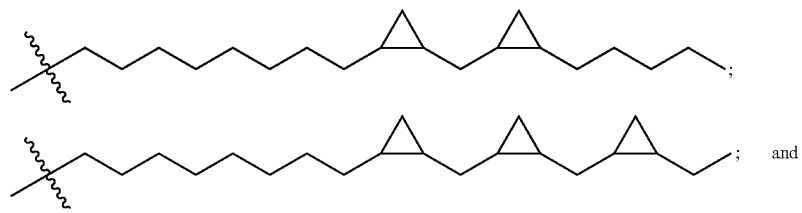

-continued

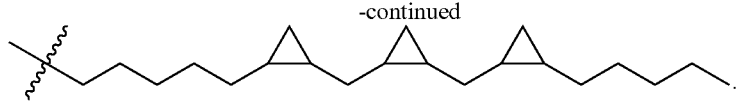

In other groups of embodiments to the cationic lipid of Formula I, one of $R^4$ or $R^5$ is selected from the group consisting of:

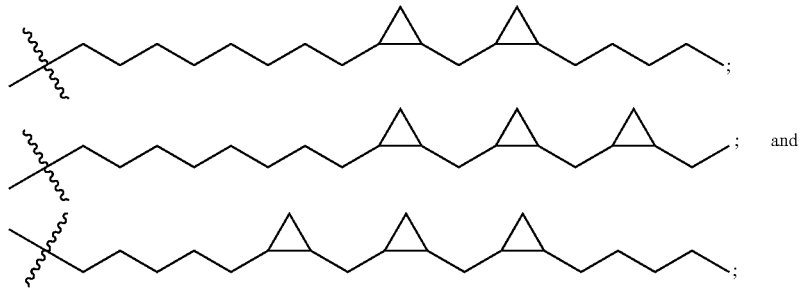

and the other of $R^4$ or $R^5$ is selected from the group consisting of:

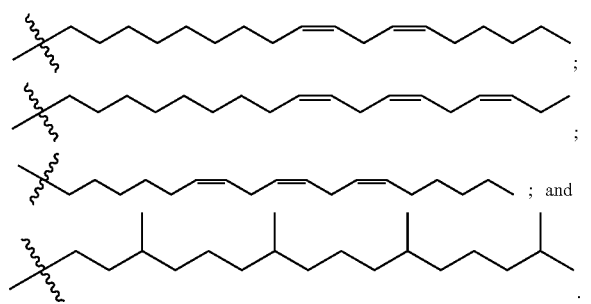

In certain embodiments, Z is an optionally substituted $C_1$-$C_2$ alkyl, $C_1$-$C_3$ alkyl, $C_1$-$C_4$ alkyl, $C_1$-$C_5$ alkyl, $C_2$-$C_3$ alkyl, $C_2$-$C_4$ alkyl, $C_2$-$C_5$ alkyl, $C_2$-$C_6$ alkyl, $C_3$-$C_4$ alkyl, $C_3$-$C_5$ alkyl, $C_3$-$C_6$ alkyl, $C_4$-$C_5$ alkyl, $C_4$-$C_6$ alkyl, $C_5$-$C_6$ alkyl, $C_2$-$C_3$ alkenyl, $C_2$-$C_4$ alkenyl, $C_2$-$C_5$ alkenyl, $C_2$-$C_6$ alkenyl, $C_3$-$C_4$ alkenyl, $C_3$-$C_5$ alkenyl, $C_3$-$C_6$ alkenyl, $C_4$-$C_5$ alkenyl, $C_4$-$C_6$ alkenyl, $C_5$-$C_6$ alkenyl, $C_2$-$C_3$ alkynyl, $C_2$-$C_4$ alkynyl, $C_2$-$C_5$ alkynyl, $C_2$-$C_6$ alkynyl, $C_3$-$C_4$ alkynyl, $C_3$-$C_5$ alkynyl, $C_3$-$C_6$ alkynyl, $C_4$-$C_5$ alkynyl, $C_4$-$C_6$ alkynyl, or $C_5$-$C_6$ alkynyl. In one particular embodiment, Z is $(CH_2)_n$ and n is 0, 1, 2, 3, 4, 5, or 6 (e.g., 1-2, 1-3, 1-4, 1-5, 1-6, 2-3, 2-4, 2-5, or 2-6). In a preferred embodiment, n is 1. In certain other embodiments, n is 2 or 3.

In particular embodiments, the cationic lipid of Formula I has the following structure:

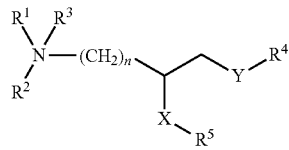

or salts thereof, wherein $R^1$, $R^2$, $R^3$, $R^4$, $R^5$, X, Y, and n are the same as described above.

In some embodiments, the cationic lipid of Formula I forms a salt (preferably a crystalline salt) with one or more anions. In one particular embodiment, the cationic lipid of Formula I is the oxalate (e.g., hemioxalate) salt thereof, which is preferably a crystalline salt.

In particularly preferred embodiments, the cationic lipid of Formula I has one of the following structures:

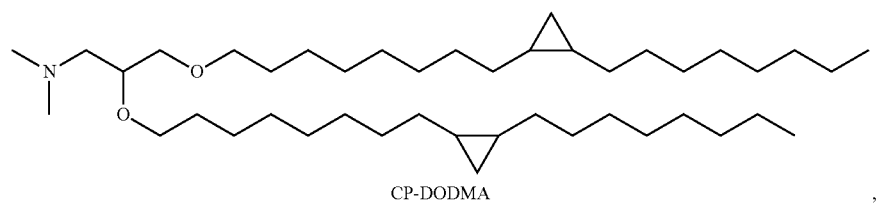

CP-DODMA

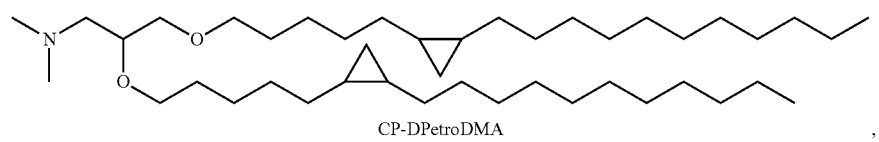

CP-DPetroDMA

-continued

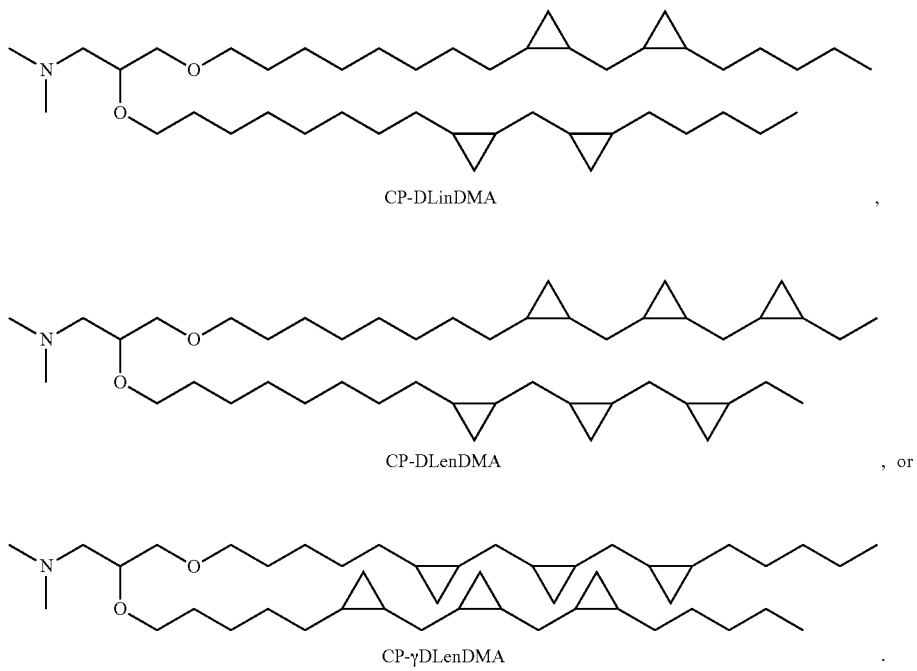

CP-DLinDMA

,

CP-DLenDMA

, or

CP-γDLenDMA

.

In another aspect, the present invention provides a cationic lipid of Formula II having the following structure:

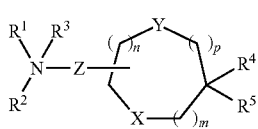

(II)

or salts thereof, wherein:
R$^1$ and R$^2$ are either the same or different and are independently an optionally substituted C$_1$-C$_6$ alkyl, C$_2$-C$_6$ alkenyl, or C$_2$-C$_6$ alkynyl, or R$^1$ and R$^2$ may join to form an optionally substituted heterocyclic ring;
R$^3$ is either absent or is hydrogen (H) or a C$_1$-C$_6$ alkyl to provide a quaternary amine;
R$^4$ and R$^5$ are either the same or different and are independently an optionally substituted C$_{10}$-C$_{24}$ alkyl, C$_{10}$-C$_{24}$ alkenyl, C$_{10}$-C$_{24}$ alkynyl, or C$_{10}$-C$_{24}$ acyl, wherein at least one of R$^4$ and R$^5$ comprises at least 1, 2, 3, 4, 5, 6, or more optionally substituted cyclic alkyl groups (e.g., 1-2, 1-3, 1-4, 1-5, 1-6, 2-3, 2-4, 2-5, or 2-6 optionally substituted cyclic alkyl groups);
m, n, and p are either the same or different and are independently either 0, 1, or 2, with the proviso that m, n, and p are not simultaneously 0;
X and Y are either the same or different and are independently O, S, N(R$^6$), C(O), C(O)O, OC(O), C(O)N(R$^6$), N(R$^6$)C(O), OC(O)N(R$^6$), N(R$^6$)C(O)O, C(O)S, C(S) O, S(O), S(O)(O), or C(S), wherein R$^6$ is hydrogen (H) or an optionally substituted C$_1$-C$_{10}$ alkyl, C$_2$-C$_{10}$ alkenyl, or C$_2$-C$_{10}$ alkynyl; and
Z is either absent or is an optionally substituted C$_1$-C$_6$ alkyl, C$_2$-C$_6$ alkenyl, or C$_2$-C$_6$ alkynyl.

In some embodiments, R$^1$ and R$^2$ are each independently hydrogen (H) or an optionally substituted C$_1$-C$_2$ alkyl, C$_1$-C$_3$ alkyl, C$_1$-C$_4$ alkyl, C$_1$-C$_5$ alkyl, C$_2$-C$_3$ alkyl, C$_2$-C$_4$ alkyl, C$_2$-C$_5$ alkyl, C$_2$-C$_6$ alkyl, C$_3$-C$_4$ alkyl, C$_3$-C$_5$ alkyl, C$_3$-C$_6$ alkyl, C$_4$-C$_5$ alkyl, C$_4$-C$_6$ alkyl, C$_5$-C$_6$ alkyl, C$_2$-C$_3$ alkenyl, C$_2$-C$_4$ alkenyl, C$_2$-C$_5$ alkenyl, C$_2$-C$_6$ alkenyl, C$_3$-C$_4$ alkenyl, C$_3$-C$_5$ alkenyl, C$_3$-C$_6$ alkenyl, C$_4$-C$_5$ alkenyl, C$_4$-C$_6$ alkenyl, C$_5$-C$_6$ alkenyl, C$_2$-C$_3$ alkynyl, C$_2$-C$_4$ alkynyl, C$_2$-C$_5$ alkynyl, C$_2$-C$_6$ alkynyl, C$_3$-C$_4$ alkynyl, C$_3$-C$_5$ alkynyl, C$_3$-C$_6$ alkynyl, C$_4$-C$_5$ alkynyl, C$_4$-C$_6$ alkynyl, or C$_5$-C$_6$ alkynyl. In particular embodiments, R$^1$ and R$^2$ are both methyl groups, both ethyl groups, or a combination of one methyl group and one ethyl group. In certain instances, R$^3$ is absent when the pH is above the pK$_a$ of the cationic lipid and R$^3$ is hydrogen (H) when the pH is below the pK$_a$ of the cationic lipid such that the amino head group is protonated. In certain other instances, R$^3$ is an optionally substituted C$_1$-C$_2$ alkyl, C$_1$-C$_3$ alkyl, C$_1$-C$_4$ alkyl, C$_1$-C$_5$ alkyl, C$_2$-C$_3$ alkyl, C$_2$-C$_4$ alkyl, C$_2$-C$_5$ alkyl, C$_2$-C$_6$ alkyl, C$_3$-C$_4$ alkyl, C$_3$-C$_5$ alkyl, C$_3$-C$_6$ alkyl, C$_4$-C$_5$ alkyl, C$_4$-C$_6$ alkyl, or C$_5$-C$_6$ alkyl to provide a quaternary amine.

In certain embodiments, R$^1$ and R$^2$ are joined to form an optionally substituted heterocyclic ring comprising 1, 2, 3, 4, 5, 6, or more carbon atoms and 1, 2, 3, 4, or more heteroatoms such as nitrogen (N), oxygen (O), sulfur (S), and mixtures thereof. In some embodiments, the optionally substituted heterocyclic ring comprises from 2 to 5 carbon atoms and from 1 to 3 heteroatoms such as nitrogen (N), oxygen (O), and/or sulfur (S). In certain embodiments, the heterocyclic ring comprises an optionally substituted imidazole, triazole (e.g., 1,2,3-triazole, 1,2,4-triazole), pyrazole, thiazole, pyrrole, furan, oxazole, isoxazole, oxazoline, oxazolidine, oxadiazole, tetrazole, and the like. In some instances, the optionally substituted heterocyclic ring comprises 5 carbon atoms and 1 nitrogen atom, wherein the heterocyclic ring can be substituted with a substituent such as a hydroxyl (—OH) group at the ortho, meta, and/or para positions. In certain instances, the heterocyclic ring comprises an optionally substituted imidazole group.

In other embodiments, $R^6$ is hydrogen (H) or an optionally substituted $C_1$-$C_2$ alkyl, $C_1$-$C_3$ alkyl, $C_1$-$C_4$ alkyl, $C_1$-$C_5$ alkyl, $C_1$-$C_6$ alkyl, $C_1$-$C_7$ alkyl, $C_1$-$C_8$ alkyl, $C_1$-$C_9$ alkyl, $C_2$-$C_3$ alkyl, $C_2$-$C_4$ alkyl, $C_2$-$C_5$ alkyl, $C_2$-$C_6$ alkyl, $C_2$-$C_7$ alkyl, $C_2$-$C_8$ alkyl, $C_2$-$C_9$ alkyl, $C_2$-$C_{10}$ alkyl, $C_3$-$C_4$ alkyl, $C_3$-$C_5$ alkyl, $C_3$-$C_6$ alkyl, $C_3$-$C_7$ alkyl, $C_3$-$C_8$ alkyl, $C_3$-$C_9$ alkyl, $C_3$-$C_{10}$ alkyl, $C_4$-$C_5$ alkyl, $C_4$-$C_6$ alkyl, $C_4$-$C_7$ alkyl, $C_4$-$C_8$ alkyl, $C_4$-$C_9$ alkyl, $C_4$-$C_{10}$ alkyl, $C_5$-$C_6$ alkyl, $C_5$-$C_7$ alkyl, $C_5$-$C_8$ alkyl, $C_5$-$C_9$ alkyl, $C_5$-$C_{10}$ alkyl, $C_6$-$C_7$ alkyl, $C_6$-$C_8$ alkyl, $C_6$-$C_9$ alkyl, $C_6$-$C_{10}$ alkyl, $C_7$-$C_8$ alkyl, $C_7$-$C_9$ alkyl, $C_7$-$C_{10}$ alkyl, $C_8$-$C_9$ alkyl, $C_8$-$C_{10}$ alkyl, $C_9$-$C_{10}$ alkyl, $C_2$-$C_3$ alkenyl, $C_2$-$C_4$ alkenyl, $C_2$-$C_5$ alkenyl, $C_2$-$C_6$ alkenyl, $C_2$-$C_7$ alkenyl, $C_2$-$C_8$ alkenyl, $C_2$-$C_9$ alkenyl, $C_3$-$C_4$ alkenyl, $C_3$-$C_5$ alkenyl, $C_3$-$C_6$ alkenyl, $C_3$-$C_7$ alkenyl, $C_3$-$C_8$ alkenyl, $C_3$-$C_9$ alkenyl, $C_3$-$C_{10}$ alkenyl, $C_4$-$C_5$ alkenyl, $C_4$-$C_6$ alkenyl, $C_4$-$C_7$ alkenyl, $C_4$-$C_8$ alkenyl, $C_4$-$C_9$ alkenyl, $C_4$-$C_{10}$ alkenyl, $C_5$-$C_6$ alkenyl, $C_5$-$C_7$ alkenyl, $C_5$-$C_8$ alkenyl, $C_5$-$C_9$ alkenyl, $C_5$-$C_{10}$ alkenyl, $C_6$-$C_7$ alkenyl, $C_6$-$C_8$ alkenyl, $C_6$-$C_9$ alkenyl, $C_6$-$C_{10}$ alkenyl, $C_7$-$C_8$ alkenyl, $C_7$-$C_9$ alkenyl, $C_7$-$C_{10}$ alkenyl, $C_8$-$C_9$ alkenyl, $C_8$-$C_{10}$ alkenyl, $C_9$-$C_{10}$ alkenyl, $C_2$-$C_3$ alkynyl, $C_2$-$C_4$ alkynyl, $C_2$-$C_5$ alkynyl, $C_2$-$C_6$ alkynyl, $C_2$-$C_7$ alkynyl, $C_2$-$C_8$ alkynyl, $C_2$-$C_9$ alkynyl, $C_3$-$C_4$ alkynyl, $C_3$-$C_5$ alkynyl, $C_3$-$C_6$ alkynyl, $C_3$-$C_7$ alkynyl, $C_3$-$C_8$ alkynyl, $C_3$-$C_9$ alkynyl, $C_3$-$C_{10}$ alkynyl, $C_4$-$C_5$ alkynyl, $C_4$-$C_6$ alkynyl, $C_4$-$C_7$ alkynyl, $C_4$-$C_8$ alkynyl, $C_4$-$C_9$ alkynyl, $C_4$-$C_{10}$ alkynyl, $C_5$-$C_6$ alkynyl, $C_5$-$C_7$ alkynyl, $C_5$-$C_8$ alkynyl, $C_5$-$C_9$ alkynyl, $C_5$-$C_{10}$ alkynyl, $C_6$-$C_7$ alkynyl, $C_6$-$C_8$ alkynyl, $C_6$-$C_9$ alkynyl, $C_6$-$C_{10}$ alkynyl, $C_7$-$C_8$ alkynyl, $C_7$-$C_9$ alkynyl, $C_7$-$C_{10}$ alkynyl, $C_8$-$C_9$ alkynyl, $C_8$-$C_{10}$ alkynyl, or $C_9$-$C_{10}$ alkynyl. In one particular embodiment, $R^6$ is selected from the group consisting of hydrogen (H), a $C_1$ alkyl (methyl) group, and a $C_2$, $C_3$, $C_4$, $C_5$, $C_6$, $C_7$, $C_8$, $C_9$, and $C_{10}$ alkyl, alkenyl, and alkynyl group.

In one embodiment, X and Y are independently selected from the group consisting of O, C(O)O, C(O)N($R^6$), N($R^6$)C(O)O, and C(O)S. In one particular embodiment, X and Y are both oxygen (O). In another particular embodiment, at least one of (e.g., both) X and Y is N($R^6$)C(O)O and each $R^6$ is independently hydrogen (H), a methyl group, or a $C_2$, $C_3$, $C_4$, $C_5$, $C_6$, $C_7$, $C_8$, $C_9$, or $C_{10}$ alkyl, alkenyl, or alkynyl group.

In certain embodiments, $R^4$ and $R^5$ are independently an optionally substituted $C_{12}$-$C_{24}$, $C_{12}$-$C_{22}$, $C_{12}$-$C_{20}$, $C_{14}$-$C_{24}$, $C_{14}$-$C_{22}$, $C_{14}$-$C_{20}$, $C_{16}$-$C_{24}$, $C_{16}$-$C_{22}$, or $C_{16}$-$C_{20}$ alkyl, alkenyl, alkynyl, or acyl group (i.e., a $C_{12}$, $C_{13}$, $C_{14}$, $C_{15}$, $C_{16}$, $C_{17}$, $C_{18}$, $C_{19}$, $C_{20}$, $C_{21}$, $C_{22}$, $C_{23}$, or $C_{24}$ alkyl, alkenyl, alkynyl, or acyl group), wherein at least one or more of (e.g., both) $R^4$ and $R^5$ independently comprises at least 1, 2, 3, 4, 5, or 6 optionally substituted cyclic alkyl groups (e.g., 1-2, 1-3, 1-4, 1-5, 1-6, 2-3, 2-4, 2-5, or 2-6 optionally substituted cyclic alkyl groups). In particular embodiments, the at least 1, 2, 3, 4, 5, or 6 optionally substituted cyclic alkyl groups present in $R^4$ and/or $R^5$ are independently selected from the group consisting of an optionally substituted saturated cyclic alkyl group, an optionally substituted unsaturated cyclic alkyl group, and combinations thereof. In certain instances, the optionally substituted saturated cyclic alkyl group comprises an optionally substituted $C_{3-8}$ cycloalkyl group (e.g., cyclopropyl, cyclobutyl, cyclopentyl, cyclohexyl, cycloheptyl, cyclooctyl, etc.). In preferred embodiments, the optionally substituted saturated cyclic alkyl group comprises a cyclopropyl group, optionally containing one or more substituents and/or heteroatoms. In other instances, the optionally substituted unsaturated cyclic alkyl group comprises an optionally substituted $C_{3-8}$ cycloalkenyl group (e.g., cyclopropenyl, cyclobutenyl, cyclopentenyl, cyclohexenyl, cycloheptenyl, cyclooctenyl, etc.). In particular embodiments, $R^4$ and $R^5$ are the same length (e.g., $C_{12}$-$C_{20}$ or $C_{18}$ alkyl chains) and contain the same number and type of cyclic alkyl group (e.g., one, two, or three $C_{3-8}$ cycloalkyl groups such as one, two, or three cyclopropyl groups on each of $R^4$ and $R^5$).

In certain other embodiments, one of $R^4$ or $R^5$ comprises at least 1, 2, 3, 4, 5, or 6 sites of unsaturation (e.g., 1-2, 1-3, 1-4, 1-5, 1-6, 2-3, 2-4, 2-5, or 2-6 sites of unsaturation) or a substituted alkyl or acyl group, and the other side-chain comprises at least 1, 2, 3, 4, 5, or 6 optionally substituted cyclic alkyl groups (e.g., 1-2, 1-3, 1-4, 1-5, 1-6, 2-3, 2-4, 2-5, or 2-6 optionally substituted cyclic alkyl groups). In embodiments where one of $R^4$ or $R^5$ comprises at least 1, 2, 3, 4, 5, or 6 sites of unsaturation, the unsaturated side-chain may comprise a dodecenyl moiety, a tetradecenyl (e.g., myristoleyl) moiety, a hexadecenyl (e.g., palmitoleyl) moiety, an octadecenyl (e.g., oleyl) moiety, an icosenyl moiety, a dodecadienyl moiety, a tetradecadienyl moiety, a hexadecadienyl moiety, an octadecadienyl moiety, an icosadienyl moiety, a dodecatrienyl moiety, a tetradectrienyl moiety, a hexadecatrienyl moiety, an octadecatrienyl moiety, an icosatrienyl moiety, or an acyl derivative thereof (e.g., oleoyl, linoleoyl, linolenoyl, γ-linolenoyl, etc.). In some instances, the octadecadienyl moiety is a linoleyl moiety. In other instances, the octadecatrienyl moiety is a linolenyl moiety or a γ-linolenyl moiety. In embodiments where one of $R^4$ or $R^5$ comprises a branched alkyl or acyl group (e.g., a substituted alkyl or acyl group), the branched alkyl or acyl group may comprise a $C_{12}$-$C_{24}$ alkyl or acyl having at least 1-6 (e.g., 1, 2, 3, 4, 5, 6, or more) $C_1$-$C_6$ alkyl substituents. In particular embodiments, the branched alkyl or acyl group comprises a $C_{12}$-$C_{20}$ or $C_{14}$-$C_{22}$ alkyl or acyl with 1-6 (e.g., 1, 2, 3, 4, 5, 6) $C_1$-$C_4$ alkyl (e.g., methyl, ethyl, propyl, or butyl) substituents. In some embodiments, the branched alkyl group comprises a phytanyl (3,7,11,15-tetramethyl-hexadecanyl) moiety and the branched acyl group comprises a phytanoyl (3,7,11,15-tetramethyl-hexadecanoyl) moiety.

In particular embodiments, $R^4$ and $R^5$ are both independently selected $C_{12}$-$C_{20}$ alkyl groups (i.e., $C_{12}$, $C_{13}$, $C_{14}$, $C_{15}$, $C_{16}$, $C_{17}$, $C_{18}$, $C_{19}$, or $C_{20}$ alkyl groups) having at least 1, 2, 3, 4, 5, or 6 optionally substituted cyclic alkyl groups (e.g., 1-2, 1-3, 1-4, 1-5, 1-6, 2-3, 2-4, 2-5, or 2-6 optionally substituted cyclic alkyl groups). In preferred embodiments, $R^4$ and $R^5$ are both $C_{18}$ alkyl groups having at least one, two, three, or more optionally substituted cyclic alkyl groups such as, for example, an optionally substituted $C_{3-8}$ cycloalkyl group (e.g., a cyclopropyl group, optionally containing one or more substituents and/or heteroatoms). In certain embodiments, each of the optionally substituted cyclic alkyl groups is independently selected and can be the same cyclic alkyl group (e.g., all cyclopropyl groups) or different cyclic alkyl groups (e.g., cyclopropyl and other cycloalkyl, heterocycloalkyl, cycloalkenyl, and/or heterocycloalkenyl groups).

In preferred embodiments, the optionally substituted cyclic alkyl groups present in $R^4$ and/or $R^5$ are located at the site(s) of unsaturation in the corresponding unsaturated side-chain. As a non-limiting example, one or both of $R^4$ and $R^5$ are $C_{18}$ alkyl groups having 1, 2, or 3 optionally substituted cyclic alkyl groups, wherein the optionally substituted cyclic alkyl groups (e.g., independently selected cyclopropyl groups) are located at one or more (e.g., all) of the sites of unsaturation present in a corresponding linoleyl moiety, linolenyl moiety, or γ-linolenyl moiety.

In alternative embodiments to the cationic lipid of Formula II, $R^4$ and $R^5$ are different and are independently an optionally substituted $C_1$-$C_{24}$ alkyl, $C_2$-$C_{24}$ alkenyl, $C_2$-$C_{24}$ alkynyl, or $C_1$-$C_{24}$ acyl, wherein at least one of $R^4$ and $R^5$ comprises at least one optionally substituted cyclic alkyl group. In certain embodiments, $R^4$ and $R^5$ are different and are independently an optionally substituted $C_4$-$C_{20}$ alkyl, $C_4$-$C_{20}$ alkenyl, $C_4$-$C_{20}$ alkynyl, or $C_4$-$C_{20}$ acyl. In some instances, $R^4$ is an optionally substituted $C_{12}$-$C_{24}$ alkyl, $C_{12}$-$C_{24}$ alkenyl, $C_{12}$-$C_{24}$ alkynyl, or $C_{12}$-$C_{24}$ acyl, and $R^5$ is an optionally substituted $C_4$-$C_{10}$ alkyl, $C_4$-$C_{10}$ alkenyl, $C_4$-$C_{10}$ alkynyl, or $C_4$-$C_{10}$ acyl. In other instances, $R^4$ is an optionally substituted $C_{12}$-$C_{20}$ or $C_{14}$-$C_{22}$ alkyl, $C_{12}$-$C_{20}$ or $C_{14}$-$C_{22}$ alkenyl, $C_{12}$-$C_{20}$ or $C_{14}$-$C_{22}$ alkynyl, or $C_{12}$-$C_{20}$ or $C_{14}$-$C_{22}$ acyl, and $R^5$ is an optionally substituted $C_4$-$C_8$ or $C_6$ alkyl, $C_4$-$C_8$ or $C_6$ alkenyl, $C_4$-$C_8$ or $C_6$ alkynyl, or $C_4$-$C_8$ or $C_6$ acyl. In certain instances, $R^4$ is an optionally substituted $C_4$-$C_{10}$ alkyl, $C_4$-$C_{10}$ alkenyl, $C_4$-$C_{10}$ alkynyl, or $C_4$-$C_{10}$ acyl, and $R^5$ is an optionally substituted $C_{12}$-$C_{24}$ alkyl, $C_{12}$-$C_{24}$ alkenyl, $C_{12}$-$C_{24}$ alkynyl, or $C_{12}$-$C_{24}$ acyl. In certain other instances, $R^4$ is an optionally substituted $C_4$-$C_8$ or $C_6$ alkyl, $C_4$-$C_8$ or $C_6$ alkenyl, $C_4$-$C_8$ or $C_6$ alkynyl, or $C_4$-$C_8$ or $C_6$ acyl, and $R^5$ is an optionally substituted $C_{12}$-$C_{20}$ or $C_{14}$-$C_{22}$ alkyl, $C_{12}$-$C_{20}$ or $C_{14}$-$C_{22}$ alkenyl, $C_{12}$-$C_{20}$ or $C_{14}$-$C_{22}$ alkynyl, or $C_{12}$-$C_{20}$ or $C_{14}$-$C_{22}$ acyl. In particular embodiments, one or more of the optionally substituted cyclic alkyl groups present in $R^4$ and/or $R^5$ are as described above.

In some groups of embodiments to the cationic lipid of Formula II, $R^4$ and $R^5$ are either the same or different and are independently selected from the group consisting of:

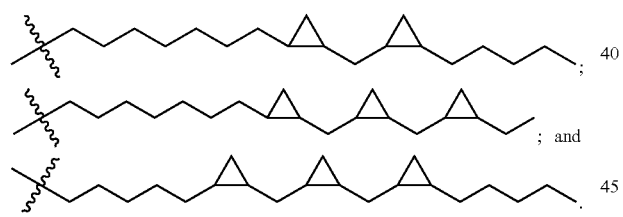

In other groups of embodiments to the cationic lipid of Formula II, one of $R^4$ or $R^5$ is selected from the group consisting of:

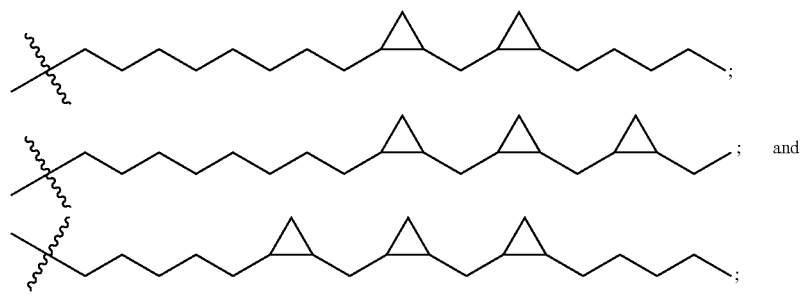

and the other of $R^4$ or $R^5$ is selected from the group consisting of:

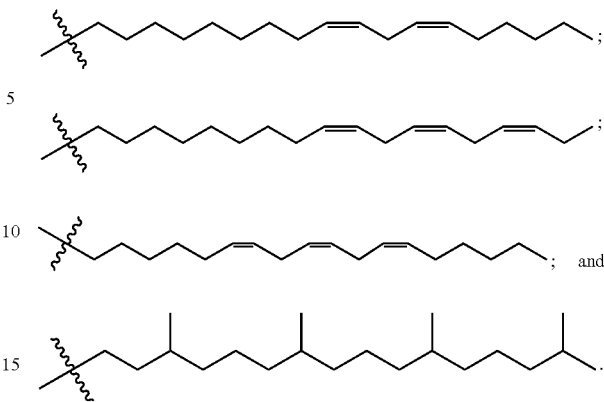

In certain embodiments, Z is an optionally substituted $C_1$-$C_2$ alkyl, $C_1$-$C_3$ alkyl, $C_1$-$C_4$ alkyl, $C_1$-$C_5$ alkyl, $C_2$-$C_3$ alkyl, $C_2$-$C_4$ alkyl, $C_2$-$C_5$ alkyl, $C_2$-$C_6$ alkyl, $C_3$-$C_4$ alkyl, $C_3$-$C_5$ alkyl, $C_3$-$C_6$ alkyl, $C_4$-$C_5$ alkyl, $C_4$-$C_6$ alkyl, $C_5$-$C_6$ alkyl, $C_2$-$C_3$ alkenyl, $C_2$-$C_4$ alkenyl, $C_2$-$C_5$ alkenyl, $C_2$-$C_6$ alkenyl, $C_3$-$C_4$ alkenyl, $C_3$-$C_5$ alkenyl, $C_3$-$C_6$ alkenyl, $C_4$-$C_5$ alkenyl, $C_4$-$C_6$ alkenyl, $C_5$-$C_6$ alkenyl, $C_2$-$C_3$ alkynyl, $C_2$-$C_4$ alkynyl, $C_2$-$C_5$ alkynyl, $C_2$-$C_6$ alkynyl, $C_3$-$C_4$ alkynyl, $C_3$-$C_5$ alkynyl, $C_3$-$C_6$ alkynyl, $C_4$-$C_5$ alkynyl, $C_4$-$C_6$ alkynyl, or $C_5$-$C_6$ alkynyl. In one particular embodiment, Z is $(CH_2)_q$ and q is 0, 1, 2, 3, 4, 5, or 6 (e.g., 1-2, 1-3, 1-4, 1-5, 1-6, 2-3, 2-4, 2-5, or 2-6). In a preferred embodiment, q is 2. In certain other embodiments, q is 1 or 3.

In particular embodiments, the cationic lipid of Formula II has the following structure:

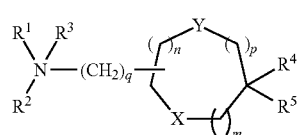

or salts thereof, wherein $R^1$, $R^2$, $R^3$, $R^4$, $R^5$, X, Y, m, n, p, and q are the same as described above.

In some embodiments, the cationic lipid of Formula II forms a salt (preferably a crystalline salt) with one or more anions. In one particular embodiment, the cationic lipid of Formula II is the oxalate (e.g., hemioxalate) salt thereof, which is preferably a crystalline salt.

In particularly preferred embodiments, the cationic lipid of Formula II has one of the following structures:

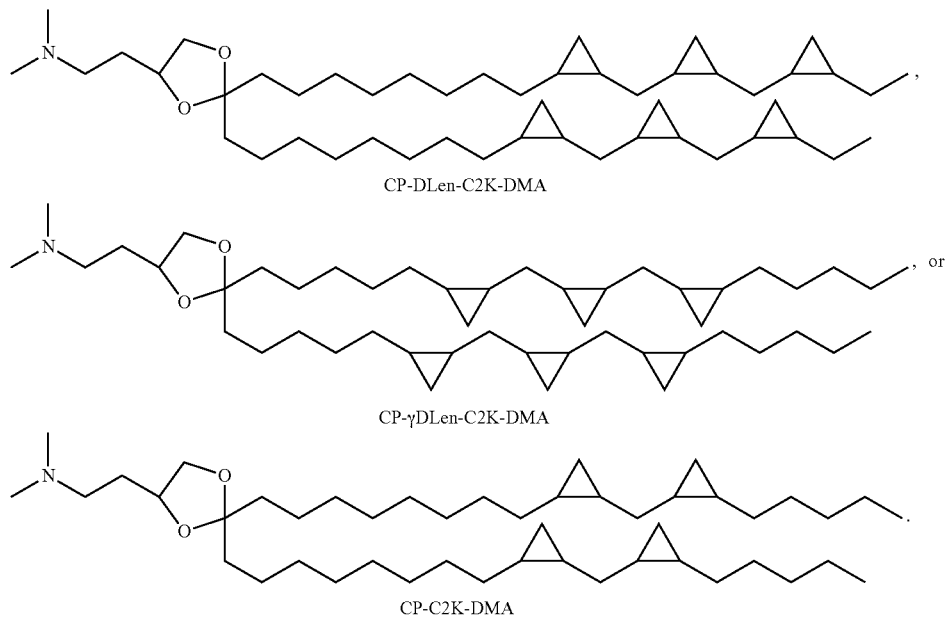

CP-DLen-C2K-DMA

CP-γDLen-C2K-DMA

CP-C2K-DMA

In yet another aspect, the present invention provides a cationic lipid of Formula III having the following structure:

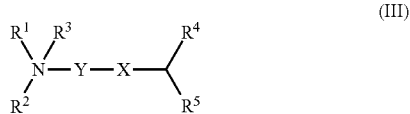

(III)

or salts thereof, wherein:

$R^1$ and $R^2$ are either the same or different and are independently hydrogen (H) or an optionally substituted $C_1$-$C_6$ alkyl, $C_2$-$C_6$ alkenyl, or $C_2$-$C_6$ alkynyl, or $R^1$ and $R^2$ may join to form an optionally substituted heterocyclic ring;

$R^3$ is either absent or is hydrogen (H) or a $C_1$-$C_6$ alkyl to provide a quaternary amine;

$R^4$ and $R^5$ are either the same or different and are independently an optionally substituted $C_{10}$-$C_{24}$ alkyl, $C_{10}$-$C_{24}$ alkenyl, $C_{10}$-$C_{24}$ alkynyl, or $C_{10}$-$C_{24}$ acyl, wherein at least one of $R^4$ and $R^5$ comprises at least 1, 2, 3, 4, 5, 6, or more optionally substituted cyclic alkyl groups (e.g., 1-2, 1-3, 1-4, 1-5, 1-6, 2-3, 2-4, 2-5, or 2-6 optionally substituted cyclic alkyl groups);

X is O, S, N($R^6$), C(O), C(O)O, OC(O), C(O)N($R^6$), N($R^6$)C(O), OC(O)N($R^6$), N($R^6$)C(O)O, C(O)S, C(S) O, S(O), S(O)(O), C(S), or an optionally substituted heterocyclic ring, wherein $R^6$ is hydrogen (H) or an optionally substituted $C_1$-$C_{10}$ alkyl, $C_2$-$C_{10}$ alkenyl, or $C_2$-$C_{10}$ alkynyl; and Y is either absent or is an optionally substituted $C_1$-$C_6$ alkyl, $C_2$-$C_6$ alkenyl, or $C_2$-$C_6$ alkynyl.

In some embodiments, $R^1$ and $R^2$ are each independently hydrogen (H) or an optionally substituted $C_1$-$C_2$ alkyl, $C_1$-$C_3$ alkyl, $C_1$-$C_4$ alkyl, $C_1$-$C_5$ alkyl, $C_2$-$C_3$ alkyl, $C_2$-$C_4$ alkyl, $C_2$-$C_5$ alkyl, $C_2$-$C_6$ alkyl, $C_3$-$C_4$ alkyl, $C_3$-$C_5$ alkyl, $C_3$-$C_6$ alkyl, $C_4$-$C_5$ alkyl, $C_4$-$C_6$ alkyl, $C_5$-$C_6$ alkyl, $C_2$-$C_3$ alkenyl, $C_2$-$C_4$ alkenyl, $C_2$-$C_5$ alkenyl, $C_2$-$C_6$ alkenyl, $C_3$-$C_4$ alkenyl, $C_3$-$C_5$ alkenyl, $C_3$-$C_6$ alkenyl, $C_4$-$C_5$ alkenyl, $C_4$-$C_6$ alkenyl, $C_5$-$C_6$ alkenyl, $C_2$-$C_3$ alkynyl, $C_2$-$C_4$ alkynyl, $C_2$-$C_5$ alkynyl, $C_2$-$C_6$ alkynyl, $C_3$-$C_4$ alkynyl, $C_3$-$C_5$ alkynyl, $C_3$-$C_6$ alkynyl, $C_4$-$C_5$ alkynyl, $C_4$-$C_6$ alkynyl, or $C_5$-$C_6$ alkynyl. In particular embodiments, $R^1$ and $R^2$ are both methyl groups, both ethyl groups, or a combination of one methyl group and one ethyl group. In certain instances, $R^3$ is absent when the pH is above the $pK_a$ of the cationic lipid and $R^3$ is hydrogen (H) when the pH is below the $pK_a$ of the cationic lipid such that the amino head group is protonated. In certain other instances, $R^3$ is an optionally substituted $C_1$-$C_2$ alkyl, $C_1$-$C_3$ alkyl, $C_1$-$C_4$ alkyl, $C_1$-$C_5$ alkyl, $C_2$-$C_3$ alkyl, $C_2$-$C_4$ alkyl, $C_2$-$C_5$ alkyl, $C_2$-$C_6$ alkyl, $C_3$-$C_4$ alkyl, $C_3$-$C_5$ alkyl, $C_3$-$C_6$ alkyl, $C_4$-$C_5$ alkyl, $C_4$-$C_6$ alkyl, or $C_5$-$C_6$ alkyl to provide a quaternary amine.

In certain embodiments, $R^1$ and $R^2$ are joined to form an optionally substituted heterocyclic ring comprising 1, 2, 3, 4, 5, 6, or more carbon atoms and 1, 2, 3, 4, or more heteroatoms such as nitrogen (N), oxygen (O), sulfur (S), and mixtures thereof. In some embodiments, the optionally substituted heterocyclic ring comprises from 2 to 5 carbon atoms and from 1 to 3 heteroatoms such as nitrogen (N), oxygen (O), and/or sulfur (S). In certain embodiments, the heterocyclic ring comprises an optionally substituted imidazole, triazole (e.g., 1,2,3-triazole, 1,2,4-triazole), pyrazole, thiazole, pyrrole, furan, oxazole, isoxazole, oxazoline, oxazolidine, oxadiazole, tetrazole, and the like. In some instances, the optionally substituted heterocyclic ring comprises 5 carbon atoms and 1 nitrogen atom, wherein the heterocyclic ring can be substituted with a substituent such as a hydroxyl (—OH) group at the ortho, meta, and/or para positions. In certain instances, the heterocyclic ring comprises an optionally substituted imidazole group.

In other embodiments, $R^6$ is hydrogen (H) or an optionally substituted $C_1$-$C_2$ alkyl, $C_1$-$C_3$ alkyl, $C_1$-$C_4$ alkyl, $C_1$-$C_5$ alkyl, $C_1$-$C_6$ alkyl, $C_1$-$C_7$ alkyl, $C_1$-$C_8$ alkyl, $C_1$-$C_9$ alkyl, $C_2$-$C_3$ alkyl, $C_2$-$C_4$ alkyl, $C_2$-$C_5$ alkyl, $C_2$-$C_6$ alkyl, $C_2$-$C_7$ alkyl, $C_2$-$C_8$ alkyl, $C_2$-$C_9$ alkyl, $C_2$-$C_{10}$ alkyl, $C_3$-$C_4$ alkyl, $C_3$-$C_5$ alkyl, $C_3$-$C_6$ alkyl, $C_3$-$C_7$ alkyl, $C_3$-$C_8$ alkyl, $C_3$-$C_9$ alkyl, $C_3$-$C_{10}$ alkyl, $C_4$-$C_5$ alkyl, $C_4$-$C_6$ alkyl, $C_4$-$C_7$ alkyl, $C_4$-$C_8$ alkyl, $C_4$-$C_9$ alkyl, $C_4$-$C_{10}$ alkyl, $C_5$-$C_6$ alkyl, $C_5$-$C_7$ alkyl, $C_5$-$C_8$ alkyl, $C_5$-$C_9$ alkyl, $C_5$-$C_{10}$ alkyl, $C_6$-$C_7$ alkyl, $C_6$-$C_8$ alkyl, $C_6$-$C_9$ alkyl, $C_6$-$C_{10}$ alkyl, $C_7$-$C_8$ alkyl, $C_7$-$C_9$ alkyl, $C_7$-$C_{10}$ alkyl, $C_8$-$C_9$ alkyl, $C_8$-$C_{10}$ alkyl, $C_9$-$C_{10}$ alkyl, $C_2$-$C_3$ alkenyl, $C_2$-$C_4$ alkenyl, $C_2$-$C_5$ alkenyl, $C_2$-$C_6$ alkenyl, $C_2$-$C_7$ alkenyl, $C_2$-$C_8$ alkenyl, $C_2$-$C_9$ alkenyl, $C_2$-$C_4$ alkenyl, $C_3$-$C_5$ alkenyl, $C_3$-$C_6$ alkenyl, $C_3$-$C_7$ alkenyl, $C_3$-$C_8$ alkenyl, $C_3$-$C_9$ alkenyl, $C_3$-$C_{10}$ alkenyl, $C_4$-$C_5$ alkenyl, $C_4$-$C_6$ alkenyl, $C_4$-$C_7$ alkenyl, $C_4$-$C_8$ alkenyl, $C_4$-$C_9$ alkenyl, $C_4$-$C_{10}$ alkenyl, $C_5$-$C_6$ alkenyl, $C_5$-$C_7$ alkenyl, $C_5$-$C_8$ alkenyl, $C_5$-$C_9$ alkenyl, $C_5$-$C_{10}$ alkenyl, $C_6$-$C_7$ alkenyl, $C_6$-$C_8$ alkenyl, $C_6$-$C_9$ alkenyl, $C_6$-$C_{10}$ alkenyl, $C_7$-$C_8$ alkenyl, $C_7$-$C_9$ alkenyl, $C_7$-$C_{10}$ alkenyl, $C_8$-$C_9$ alkenyl, $C_8$-$C_{10}$ alkenyl, $C_9$-$C_{10}$ alkenyl, $C_2$-$C_3$ alkynyl, $C_2$-$C_4$ alkynyl, $C_2$-$C_5$ alkynyl, $C_2$-$C_6$ alkynyl, $C_2$-$C_7$ alkynyl, $C_2$-$C_8$ alkynyl, $C_2$-$C_9$ alkynyl, $C_3$-$C_4$ alkynyl, $C_3$-$C_5$ alkynyl, $C_3$-$C_6$ alkynyl, $C_3$-$C_7$ alkynyl, $C_3$-$C_8$ alkynyl, $C_3$-$C_9$ alkynyl, $C_3$-$C_{10}$ alkynyl, $C_4$-$C_5$ alkynyl, $C_4$-$C_6$ alkynyl, $C_4$-$C_7$ alkynyl, $C_4$-$C_8$ alkynyl, $C_4$-$C_9$ alkynyl, $C_4$-$C_{10}$ alkynyl, $C_5$-$C_6$ alkynyl, $C_5$-$C_7$ alkynyl, $C_5$-$C_8$ alkynyl, $C_5$-$C_9$ alkynyl, $C_5$-$C_{10}$ alkynyl, $C_6$-$C_7$ alkynyl, $C_6$-$C_8$ alkynyl, $C_6$-$C_9$ alkynyl, $C_6$-$C_{10}$ alkynyl, $C_7$-$C_8$ alkynyl, $C_7$-$C_9$ alkynyl, $C_7$-$C_{10}$ alkynyl, $C_8$-$C_9$ alkynyl, $C_8$-$C_{10}$ alkynyl, or $C_9$-$C_{10}$ alkynyl. In one particular embodiment, $R^6$ is selected from the group consisting of hydrogen (H), a $C_1$ alkyl (methyl) group, and a $C_2$, $C_3$, $C_4$, $C_5$, $C_6$, $C_7$, $C_8$, $C_9$, and $C_{10}$ alkyl, alkenyl, and alkynyl group.

In one embodiment, X is O, C(O)O, C(O)N($R^6$), N($R^6$)C(O)O, or C(O)S. In one particular embodiment, X is C(O)O. In another particular embodiment, X is N($R^6$)C(O)O and $R^6$ is hydrogen (H), a methyl group, or a $C_2$, $C_3$, $C_4$, $C_5$, $C_6$, $C_7$, $C_8$, $C_9$, or $C_{10}$ alkyl, alkenyl, or alkynyl group. In certain other embodiments, X is an optionally substituted heterocyclic ring. In particular embodiments, the heterocyclic ring comprises 1, 2, 3, 4, 5, 6, or more carbon atoms and 1, 2, 3, 4, or more heteroatoms such as nitrogen (N), oxygen (O), sulfur (S), and mixtures thereof. In some embodiments, the optionally substituted heterocyclic ring comprises from 2 to 5 carbon atoms and from 1 to 3 heteroatoms such as nitrogen (N), oxygen (O), and/or sulfur (S). In certain embodiments, the heterocyclic ring comprises an optionally substituted imidazole, triazole (e.g., 1,2,3-triazole, 1,2,4-triazole), pyrazole, thiazole, pyrrole, furan, oxazole, isoxazole, oxazoline, oxazolidine, oxadiazole, tetrazole, and the like.

In certain embodiments, $R^4$ and $R^5$ are independently an optionally substituted $C_{12}$-$C_{24}$, $C_{12}$-$C_{22}$, $C_{12}$-$C_{20}$, $C_{14}$-$C_{24}$, $C_{14}$-$C_{22}$, $C_{14}$-$C_{20}$, $C_{16}$-$C_{24}$, $C_{16}$-$C_{22}$, or $C_{16}$-$C_{20}$ alkyl, alkenyl, alkynyl, or acyl group (i.e., a $C_{12}$, $C_{13}$, $C_{14}$, $C_{15}$, $C_{16}$, $C_{17}$, $C_{18}$, $C_{19}$, $C_{20}$, $C_{21}$, $C_{22}$, $C_{23}$, or $C_{24}$ alkyl, alkenyl, alkynyl, or acyl group), wherein at least one or more of (e.g., both) $R^4$ and $R^5$ independently comprises at least 1, 2, 3, 4, 5, or 6 optionally substituted cyclic alkyl groups (e.g., 1-2, 1-3, 1-4, 1-5, 1-6, 2-3, 2-4, 2-5, or 2-6 optionally substituted cyclic alkyl groups). In particular embodiments, the at least 1, 2, 3, 4, 5, or 6 optionally substituted cyclic alkyl groups present in $R^4$ and/or $R^5$ are independently selected from the group consisting of an optionally substituted saturated cyclic alkyl group, an optionally substituted unsaturated cyclic alkyl group, and combinations thereof. In certain instances, the optionally substituted saturated cyclic alkyl group comprises an optionally substituted $C_{3-8}$ cycloalkyl group (e.g., cyclopropyl, cyclobutyl, cyclopentyl, cyclohexyl, cycloheptyl, cyclooctyl, etc.). In preferred embodiments, the optionally substituted saturated cyclic alkyl group comprises a cyclopropyl group, optionally containing one or more substituents and/or heteroatoms. In other instances, the optionally substituted unsaturated cyclic alkyl group comprises an optionally substituted $C_{3-8}$ cycloalkenyl group (e.g., cyclopropenyl, cyclobutenyl, cyclopentenyl, cyclohexenyl, cycloheptenyl, cyclooctenyl, etc.). In particular embodiments, $R^4$ and $R^5$ are the same length (e.g., $C_{12}$-$C_{20}$ or $C_{18}$ alkyl chains) and contain the same number and type of cyclic alkyl group (e.g., one, two, or three $C_{3-8}$ cycloalkyl groups such as one, two, or three cyclopropyl groups on each of $R^4$ and $R^5$).

In certain other embodiments, one of $R^4$ or $R^5$ comprises at least 1, 2, 3, 4, 5, or 6 sites of unsaturation (e.g., 1-2, 1-3, 1-4, 1-5, 1-6, 2-3, 2-4, 2-5, or 2-6 sites of unsaturation) or a substituted alkyl or acyl group, and the other side-chain comprises at least 1, 2, 3, 4, 5, or 6 optionally substituted cyclic alkyl groups (e.g., 1-2, 1-3, 1-4, 1-5, 1-6, 2-3, 2-4, 2-5, or 2-6 optionally substituted cyclic alkyl groups). In embodiments where one of $R^4$ or $R^5$ comprises at least 1, 2, 3, 4, 5, or 6 sites of unsaturation, the unsaturated side-chain may comprise a dodecenyl moiety, a tetradecenyl (e.g., myristoleyl) moiety, a hexadecenyl (e.g., palmitoleyl) moiety, an octadecenyl (e.g., oleyl) moiety, an icosenyl moiety, a dodecadienyl moiety, a tetradecadienyl moiety, a hexadecadienyl moiety, an octadecadienyl moiety, an icosadienyl moiety, a dodecatrienyl moiety, a tetradectrienyl moiety, a hexadecatrienyl moiety, an octadecatrienyl moiety, an icosatrienyl moiety, or an acyl derivative thereof (e.g., oleoyl, linoleoyl, linolenoyl, γ-linolenoyl, etc.). In some instances, the octadecadienyl moiety is a linoleyl moiety. In other instances, the octadecatrienyl moiety is a linolenyl moiety or a γ-linolenyl moiety. In embodiments where one of $R^4$ or $R^5$ comprises a branched alkyl or acyl group (e.g., a substituted alkyl or acyl group), the branched alkyl or acyl group may comprise a $C_{12}$-$C_{24}$ alkyl or acyl having at least 1-6 (e.g., 1, 2, 3, 4, 5, 6, or more) $C_1$-$C_6$ alkyl substituents. In particular embodiments, the branched alkyl or acyl group comprises a $C_{12}$-$C_{20}$ or $C_{14}$-$C_{22}$ alkyl or acyl with 1-6 (e.g., 1, 2, 3, 4, 5, 6) $C_1$-$C_4$ alkyl (e.g., methyl, ethyl, propyl, or butyl) substituents. In some embodiments, the branched alkyl group comprises a phytanyl (3,7,11,15-tetramethyl-hexadecanyl) moiety and the branched acyl group comprises a phytanoyl (3,7,11,15-tetramethyl-hexadecanoyl) moiety.

In particular embodiments, $R^4$ and $R^5$ are both independently selected $C_{12}$-$C_{20}$ alkyl groups (i.e., $C_{12}$, $C_{13}$, $C_{14}$, $C_{15}$, $C_{16}$, $C_{17}$, $C_{18}$, $C_{19}$, or $C_{20}$ alkyl groups) having at least 1, 2, 3, 4, 5, or 6 optionally substituted cyclic alkyl groups (e.g., 1-2, 1-3, 1-4, 1-5, 1-6, 2-3, 2-4, 2-5, or 2-6 optionally substituted cyclic alkyl groups). In preferred embodiments, $R^4$ and $R^5$ are both $C_{18}$ alkyl groups having at least one, two, three, or more optionally substituted cyclic alkyl groups such as, for example, an optionally substituted $C_{3-8}$ cycloalkyl group (e.g., a cyclopropyl group, optionally containing one or more substituents and/or heteroatoms). In certain embodiments, each of the optionally substituted cyclic alkyl groups is independently selected and can be the same cyclic alkyl group (e.g., all cyclopropyl groups) or different cyclic alkyl groups (e.g., cyclopropyl and other cycloalkyl, heterocycloalkyl, cycloalkenyl, and/or heterocycloalkenyl groups).

In preferred embodiments, the optionally substituted cyclic alkyl groups present in $R^4$ and/or $R^5$ are located at the site(s) of unsaturation in the corresponding unsaturated side-chain. As a non-limiting example, one or both of $R^4$ and $R^5$ are $C_{18}$ alkyl groups having 1, 2, or 3 optionally substituted cyclic alkyl groups, wherein the optionally substituted cyclic alkyl groups (e.g., independently selected cyclopropyl groups) are located at one or more (e.g., all) of the sites of unsaturation present in a corresponding linoleyl moiety, linolenyl moiety, or γ-linolenyl moiety.

In alternative embodiments to the cationic lipid of Formula III, $R^4$ and $R^5$ are different and are independently an optionally substituted $C_1$-$C_{24}$ alkyl, $C_2$-$C_{24}$ alkenyl, $C_2$-$C_{24}$ alkynyl, or $C_1$-$C_{24}$ acyl, wherein at least one of $R^4$ and $R^5$ comprises at least one optionally substituted cyclic alkyl group. In certain embodiments, $R^4$ and $R^5$ are different and are independently an optionally substituted $C_4$-$C_{20}$ alkyl, $C_4$-$C_{20}$ alkenyl, $C_4$-$C_{20}$ alkynyl, or $C_4$-$C_{20}$ acyl. In some instances, $R^4$ is an optionally substituted $C_{12}$-$C_{24}$ alkyl, $C_{12}$-$C_{24}$ alkenyl, $C_{12}$-$C_{24}$ alkynyl, or $C_{12}$-$C_{24}$ acyl, and $R^5$ is an optionally substituted $C_4$-$C_{10}$ alkyl, $C_4$-$C_{10}$ alkenyl, $C_4$-$C_{10}$ alkynyl, or $C_4$-$C_{10}$ acyl. In other instances, $R^4$ is an optionally substituted $C_{12}$-$C_{20}$ or $C_{14}$-$C_{22}$ alkyl, $C_{12}$-$C_{20}$ or $C_{14}$-$C_{22}$ alkenyl, $C_{12}$-$C_{20}$ or $C_{14}$-$C_{22}$ alkynyl, or $C_{12}$-$C_{20}$ or $C_{14}$-$C_{22}$ acyl, and $R^5$ is an optionally substituted $C_4$-$C_8$ or $C_6$ alkyl, $C_4$-$C_8$ or $C_6$ alkenyl, $C_4$-$C_8$ or $C_6$ alkynyl, or $C_4$-$C_8$ or $C_6$ acyl. In certain instances, $R^4$ is an optionally substituted $C_4$-$C_{10}$ alkyl, $C_4$-$C_{10}$ alkenyl, $C_4$-$C_{10}$ alkynyl, or $C_4$-$C_{10}$ acyl, and $R^5$ is an optionally substituted $C_{12}$-$C_{24}$ alkyl, $C_{12}$-$C_{24}$ alkenyl, $C_{12}$-$C_{24}$ alkynyl, or $C_{12}$-$C_{24}$ acyl. In certain other instances, $R^4$ is an optionally substituted $C_4$-$C_8$ or $C_6$ alkyl, $C_4$-$C_8$ or $C_6$ alkenyl, $C_4$-$C_8$ or $C_6$ alkynyl, or $C_4$-$C_8$ or $C_6$ acyl, and $R^5$ is an optionally substituted $C_{12}$-$C_{20}$ or $C_{14}$-$C_{22}$ alkyl, $C_{12}$-$C_{20}$ or $C_{14}$-$C_{22}$ alkenyl, $C_{12}$-$C_{20}$ or $C_{14}$-$C_{22}$ alkynyl, or $C_{12}$-$C_{20}$ or $C_{14}$-$C_{22}$ acyl. In particular embodiments, one or more of the optionally substituted cyclic alkyl groups present in $R^4$ and/or $R^5$ are as described above.

In some groups of embodiments to the cationic lipid of Formula III, $R^4$ and $R^5$ are either the same or different and are independently selected from the group consisting of:

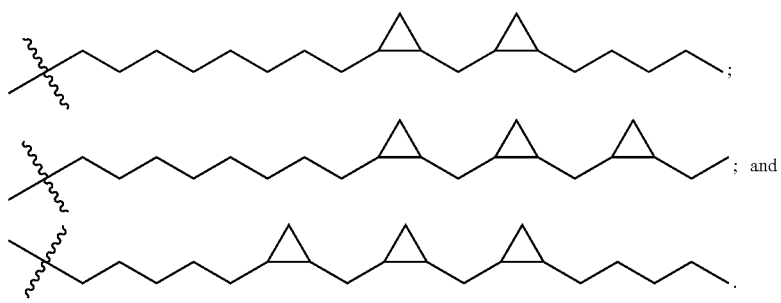

In other groups of embodiments to the cationic lipid of Formula III, one of $R^4$ or $R^5$ is selected from the group consisting of:

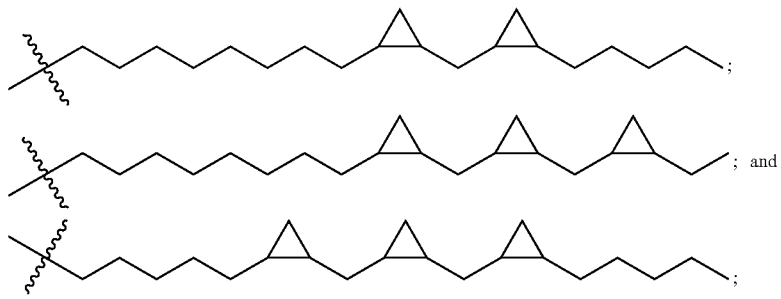

and the other of $R^4$ or $R^5$ is selected from the group consisting of:

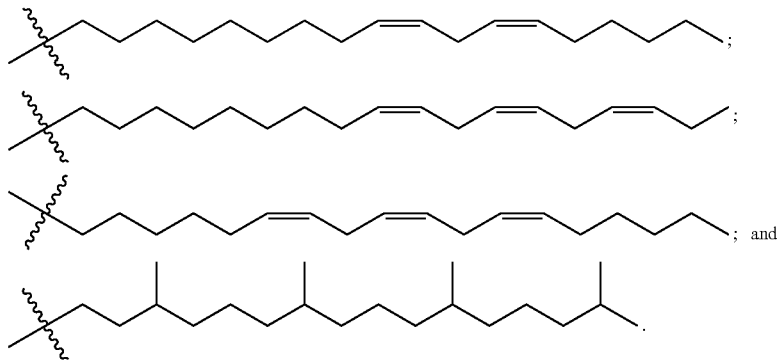

In certain embodiments, Y is an optionally substituted $C_1$-$C_2$ alkyl, $C_1$-$C_3$ alkyl, $C_1$-$C_4$ alkyl, $C_1$-$C_5$ alkyl, $C_2$-$C_3$ alkyl, $C_2$-$C_4$ alkyl, $C_2$-$C_5$ alkyl, $C_2$-$C_6$ alkyl, $C_3$-$C_4$ alkyl, $C_3$-$C_5$ alkyl, $C_3$-$C_6$ alkyl, $C_4$-$C_5$ alkyl, $C_4$-$C_6$ alkyl, $C_5$-$C_6$ alkyl, $C_2$-$C_3$ alkenyl, $C_2$-$C_4$ alkenyl, $C_2$-$C_5$ alkenyl, $C_2$-$C_6$ alkenyl, $C_3$-$C_4$ alkenyl, $C_3$-$C_5$ alkenyl, $C_3$-$C_6$ alkenyl, $C_4$-$C_5$ alkenyl, $C_4$-$C_6$ alkenyl, $C_5$-$C_6$ alkenyl, $C_2$-$C_3$ alkynyl, $C_2$-$C_4$ alkynyl, $C_2$-$C_5$ alkynyl, $C_2$-$C_6$ alkynyl, $C_3$-$C_4$ alkynyl, $C_3$-$C_5$ alkynyl, $C_3$-$C_6$ alkynyl, $C_4$-$C_5$ alkynyl, $C_4$-$C_6$ alkynyl, or $C_5$-$C_6$ alkynyl. In one particular embodiment, Y is $(CH_2)_n$ and n is 0, 1, 2, 3, 4, 5, or 6 (e.g., 1-2, 1-3, 1-4, 1-5, 1-6, 2-3, 2-4, 2-5, 2-6, 3-4, 3-5, or 3-6). In a preferred embodiment, n is 3. In certain other embodiments, n is 2 or 4.

In particular embodiments, the cationic lipid of Formula III has the following structure:

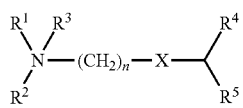

or salts thereof, wherein $R^1$, $R^2$, $R^3$, $R^4$, $R^5$, X, and n are the same as described above.

In some embodiments, the cationic lipid of Formula III forms a salt (preferably a crystalline salt) with one or more anions. In one particular embodiment, the cationic lipid of Formula III is the oxalate (e.g., hemioxalate) salt thereof, which is preferably a crystalline salt.

In particularly preferred embodiments, the cationic lipid of Formula III has one of the following structures:

removed to reveal the original functional group. In certain instances, an "alcohol protecting group" is used. An "alcohol protecting group" is any group which decreases or eliminates the unwanted reactivity of an alcohol functional group. Protecting groups can be added and removed using techniques well known in the art.

In certain embodiments, the cationic lipids of the present invention have at least one protonatable or deprotonatable group, such that the lipid is positively charged at a pH at or below physiological pH (e.g., pH 7.4), and neutral at a second pH, preferably at or above physiological pH. It will be understood by one of ordinary skill in the art that the addition or removal of protons as a function of pH is an equilibrium process, and that the reference to a charged or a neutral lipid refers to the nature of the predominant species and does not require that all of the lipid be present in the charged or neutral form. Lipids that have more than one protonatable or deprotonatable group, or which are zwiterionic, are not excluded from use in the invention.

In certain other embodiments, protonatable lipids according to the invention have a $pK_a$ of the protonatable group in the range of about 4 to about 11. Most preferred is a $pK_a$ of about 4 to about 7, because these lipids will be cationic at a lower pH formulation stage, while particles will be largely (though not completely) surface neutralized at physiological pH of around pH 7.4. One of the benefits of this $pK_a$ is that at least some nucleic acid associated with the outside surface of the particle will lose its electrostatic interaction at physiological pH and be removed by simple dialysis, thus greatly reducing the particle's susceptibility to clearance.

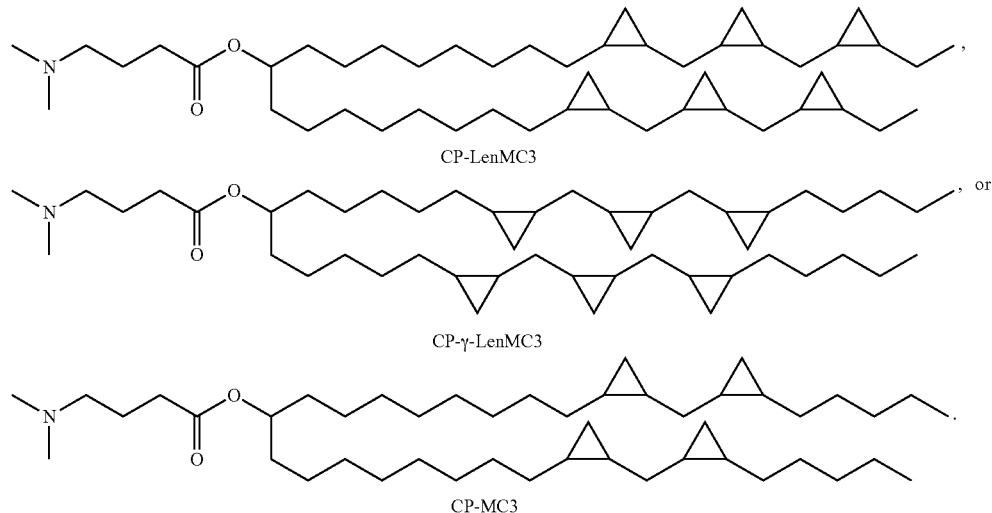

The compounds of the invention may be prepared by known organic synthesis techniques, including the methods described in the Examples. In some embodiments, the synthesis of the cationic lipids of the invention may require the use of protecting groups. Protecting group methodology is well known to those skilled in the art (see, e.g., PROTECTIVE GROUPS IN ORGANIC SYNTHESIS, Green, T. W. et. al., Wiley-Interscience, New York City, 1999). Briefly, protecting groups within the context of this invention are any group that reduces or eliminates the unwanted reactivity of a functional group. A protecting group can be added to a functional group to mask its reactivity during certain reactions and then IV. Active Agents Active agents (e.g., therapeutic agents) include any molecule or compound capable of exerting a desired effect on a cell, tissue, tumor, organ, or subject. Such effects may be, e.g., biological, physiological, and/or cosmetic. Active agents may be any type of molecule or compound including, but not limited to, nucleic acids, peptides, polypeptides, small molecules, and mixtures thereof. Non-limiting examples of nucleic acids include interfering RNA molecules (e.g., dsRNA such as siRNA, Dicer-substrate dsRNA, shRNA, aiRNA, and/or miRNA), antisense oligonucleotides, plasmids, ribozymes, immunostimulatory oligonucleotides, and mixtures thereof. Examples of peptides or polypeptides include, without limitation, antibodies (e.g., polyclonal antibodies, monoclonal antibodies, antibody fragments; humanized antibodies, recombinant antibodies, recombinant human antibodies, and/or Primatized™ antibodies), cytokines, growth factors, apoptotic factors, differentiation-inducing factors, cell-surface receptors and their ligands, hormones, and mixtures thereof. Examples of small molecules include, but are not limited to, small organic molecules or compounds such as any conventional agent or drug known to those of skill in the art.

In some embodiments, the active agent is a therapeutic agent, or a salt or derivative thereof. Therapeutic agent derivatives may be therapeutically active themselves or they may be prodrugs, which become active upon further modification. Thus, in one embodiment, a therapeutic agent derivative retains some or all of the therapeutic activity as compared to the unmodified agent, while in another embodiment, a therapeutic agent derivative is a prodrug that lacks therapeutic activity, but becomes active upon further modification.

In preferred embodiments, the lipid particles described herein are associated with a nucleic acid, resulting in a nucleic acid-lipid particle (e.g., SNALP). Non-limiting exemplary embodiments related to selecting, synthesizing, and modifying nucleic acids such as siRNA, Dicer-substrate dsRNA, shRNA, aiRNA, miRNA, antisense oligonucleotides, ribozymes, and immunostimulatory oligonucleotides are described, for example, in U.S. Patent Publication No. 20070135372; in U.S. Patent Publication No. 20110076335; and in PCT Publication No. WO 2010/105372, the disclosures of which are each herein incorporated by reference in their entirety for all purposes.

In certain embodiments, the nucleic acid (e.g., interfering RNA) component of the nucleic acid-lipid particle (e.g., SNALP) comprises at least one modified nucleotide (e.g., at least 1, 2, 3, 4, 5, 6, 7, 8, 9, 10, 11, 12, or more modified nucleotides). In certain instances, the nucleic acid (e.g., interfering RNA such as an siRNA) comprises modified nucleotides including, but not limited to, 2'-O-methyl (2'OMe) nucleotides, 2'-deoxy-2'-fluoro (2'F) nucleotides, 2'-deoxy nucleotides, 2'-O-(2-methoxyethyl) (MOE) nucleotides, locked nucleic acid (LNA) nucleotides, 5-C-methyl nucleotides, 4'-thio nucleotides, 2'-amino nucleotides, 2'-C-allyl nucleotides, and mixtures thereof. In particular embodiments, the modified interfering RNA (e.g., modified siRNA) is generally less immunostimulatory than a corresponding unmodified interfering RNA (e.g., unmodified siRNA) sequence and retains RNAi activity against the target gene of interest. In some embodiments, the modified interfering RNA (e.g., modified siRNA) contains at least one 2'OMe purine or pyrimidine nucleotide such as a 2'OMe-guanosine, 2'OMe-uridine, 2'OMe-adenosine, and/or 2'OMe-cytosine nucleotide. The modified nucleotides can be present in one strand (i.e., sense or antisense) or both strands of the interfering RNA (e.g., siRNA). In some preferred embodiments, one or more of the uridine and/or guanosine nucleotides are modified (e.g., 2'OMe-modified) in one strand (i.e., sense or antisense) or both strands of the interfering RNA (e.g., siRNA). In these embodiments, the modified interfering RNA (e.g., modified siRNA) can further comprise one or more modified (e.g., 2'OMe-modified) adenosine and/or modified (e.g., 2'OMe-modified) cytosine nucleotides. In other preferred embodiments, only uridine and/or guanosine nucleotides are modified (e.g., 2'OMe-modified) in one strand (i.e., sense or antisense) or both strands of the interfering RNA (e.g., siRNA). The interfering RNA (e.g., siRNA) sequences may have overhangs (e.g., 3' or 5' overhangs as described in Elbashir et al., Genes Dev., 15:188 (2001) or Nykanen et al., Cell, 107:309 (2001)), or may lack overhangs (i.e., have blunt ends). The interfering RNA (e.g., siRNA) sequences may comprise one or more modified nucleotides in the double-stranded (duplex) region and/or in one or both of the overhangs (e.g., 3' overhangs) when present.

The nucleic acid (e.g., interfering RNA) component of the nucleic acid-lipid particle (e.g., SNALP) can be used to downregulate or silence the translation (i.e., expression) of a gene of interest. Non-limiting examples of genes of interest include genes associated with metabolic diseases and disorders (e.g., liver diseases and disorders), genes associated with cell proliferation, tumorigenesis, and/or cell transformation (e.g., a cell proliferative disorder such as cancer), angiogenic genes, receptor ligand genes, immunomodulator genes (e.g., those associated with inflammatory and autoimmune responses), genes associated with viral infection and survival, and genes associated with neurodegenerative disorders. See, e.g., U.S. Patent Publication No. 20110076335 for a description of exemplary target genes (including their Genbank Accession Nos.) which may be downregulated or silenced by the nucleic acid (e.g., interfering RNA) of the nucleic acid-lipid particle (e.g., SNALP).

Non-limiting examples of gene sequences associated with tumorigenesis or cell transformation include polo-like kinase 1 (PLK-1), cyclin-dependent kinase 4 (CDK4), COP1, ring-box 1 (RBX1), WEE1, Eg5 (KSP, KIF11), forkhead box M1 (FOXM1), RAM2 (R1, CDCA7L), XIAP, CSN5 (JAB1), and HDAC2. Non-limiting examples of gene sequences associated with metabolic diseases and disorders include apolipoprotein B (APOB), apolipoprotein CIII (APOC3), apolipoprotein E (APOE), proprotein convertase subtilisin/kexin type 9 (PCSK9), diacylglycerol O-acyltransferase type 1 (DGAT1), and diacylglyerol O-acyltransferase type 2 (DGAT2). Non-limiting examples of gene sequences associated with viral infection and survival include host factors such as tissue factor (TF) or nucleic acid sequences from Filoviruses such as Ebola virus and Marburg virus (e.g., VP30, VP35, nucleoprotein (NP), polymerase protein (L-pol), VP40, glycoprotein (GP), and VP24); Arenaviruses such as Lassa virus (e.g., NP, GP, L, and/or Z genes), Junin virus, Machupo virus, Guanarito virus, and Sabia virus; Hepatitis viruses such as Hepatitis A, B, C, D, and E viruses; Influenza viruses such as Influenza A, B, and C viruses; Human Immunodeficiency Virus (HIV); Herpes viruses; and Human Papilloma Viruses (HPV).

In other embodiments, the active agent associated with the lipid particles of the invention may comprise one or more therapeutic proteins, polypeptides, or small organic molecules or compounds. Non-limiting examples of such therapeutically effective agents or drugs include oncology drugs (e.g., chemotherapy drugs, hormonal therapeutic agents, immunotherapeutic agents, radiotherapeutic agents, etc.), lipid-lowering agents, anti-viral drugs, anti-inflammatory compounds, antidepressants, stimulants, analgesics, antibiotics, birth control medication, antipyretics, vasodilators, anti-angiogenics, cytovascular agents, signal transduction inhibitors, cardiovascular drugs such as anti-arrhythmic agents, hormones, vasoconstrictors, and steroids. These active agents may be administered alone in the lipid particles of the invention, or in combination (e.g., co-administered) with lipid particles of the invention comprising nucleic acid such as interfering RNA. Non-limiting examples of these types of active agents are described, e.g., in U.S. Patent Publication No. 20110076335, the disclosure of which is herein incorporated by reference in its entirety for all purposes.

V. Lipid Particles

In certain aspects, the present invention provides lipid particles comprising one or more of the cationic (amino) lipids or salts thereof described herein. In some embodiments, the lipid particles of the invention further comprise one or more non-cationic lipids. In other embodiments, the lipid particles further comprise one or more conjugated lipids capable of reducing or inhibiting particle aggregation. In additional embodiments, the lipid particles further comprise one or more active agents or therapeutic agents such as therapeutic nucleic acids (e.g., interfering RNA such as siRNA).

Lipid particles include, but are not limited to, lipid vesicles such as liposomes. As used herein, a lipid vesicle includes a structure having lipid-containing membranes enclosing an aqueous interior. In particular embodiments, lipid vesicles comprising one or more of the cationic lipids described herein are used to encapsulate nucleic acids within the lipid vesicles. In other embodiments, lipid vesicles comprising one or more of the cationic lipids described herein are complexed with nucleic acids to form lipoplexes.

The lipid particles of the invention typically comprise an active agent or therapeutic agent, a cationic lipid, a non-cationic lipid, and a conjugated lipid that inhibits aggregation of particles. In some embodiments, the active agent or therapeutic agent is fully encapsulated within the lipid portion of the lipid particle such that the active agent or therapeutic agent in the lipid particle is resistant in aqueous solution to enzymatic degradation, e.g., by a nuclease or protease. In other embodiments, the lipid particles described herein are substantially non-toxic to mammals such as humans. The lipid particles of the invention typically have a mean diameter of from about 30 nm to about 150 nm, from about 40 nm to about 150 nm, from about 50 nm to about 150 nm, from about 60 nm to about 130 nm, from about 70 nm to about 110 nm, or from about 70 to about 90 nm. The lipid particles of the invention also typically have a lipid:therapeutic agent (e.g., lipid:nucleic acid) ratio (mass/mass ratio) of from about 1:1 to about 100:1, from about 1:1 to about 50:1, from about 2:1 to about 25:1, from about 3:1 to about 20:1, from about 5:1 to about 15:1, or from about 5:1 to about 10:1.

In preferred embodiments, the lipid particles of the invention are serum-stable nucleic acid-lipid particles (SNALP) which comprise an interfering RNA (e.g., dsRNA such as siRNA, Dicer-substrate dsRNA, shRNA, aiRNA, and/or miRNA), a cationic lipid (e.g., one or more cationic lipids of Formulas I-III or salts thereof as set forth herein), a non-cationic lipid (e.g., mixtures of one or more phospholipids and cholesterol), and a conjugated lipid that inhibits aggregation of the particles (e.g., one or more PEG-lipid conjugates). The SNALP may comprise at least 1, 2, 3, 4, 5, 6, 7, 8, 9, 10, or more unmodified and/or modified interfering RNA molecules (e.g., siRNA). Nucleic acid-lipid particles and their method of preparation are described in, e.g., U.S. Pat. Nos. 5,753,613; 5,785,992; 5,705,385; 5,976,567; 5,981,501; 6,110,745; and 6,320,017; and PCT Publication No. WO 96/40964, the disclosures of which are each herein incorporated by reference in their entirety for all purposes.

In the nucleic acid-lipid particles of the invention, the nucleic acid may be fully encapsulated within the lipid portion of the particle, thereby protecting the nucleic acid from nuclease degradation. In preferred embodiments, a SNALP comprising a nucleic acid such as an interfering RNA is fully encapsulated within the lipid portion of the particle, thereby protecting the nucleic acid from nuclease degradation. In certain instances, the nucleic acid in the SNALP is not substantially degraded after exposure of the particle to a nuclease at 37° C. for at least about 20, 30, 45, or 60 minutes. In certain other instances, the nucleic acid in the SNALP is not substantially degraded after incubation of the particle in serum at 37° C. for at least about 30, 45, or 60 minutes or at least about 2, 3, 4, 5, 6, 7, 8, 9, 10, 12, 14, 16, 18, 20, 22, 24, 26, 28, 30, 32, 34, or 36 hours. In other embodiments, the nucleic acid is complexed with the lipid portion of the particle. One of the benefits of the formulations of the present invention is that the nucleic acid-lipid particle compositions are substantially non-toxic to mammals such as humans.

The term "fully encapsulated" indicates that the nucleic acid in the nucleic acid-lipid particle is not significantly degraded after exposure to serum or a nuclease assay that would significantly degrade free DNA or RNA. In a fully encapsulated system, preferably less than about 25% of the nucleic acid in the particle is degraded in a treatment that would normally degrade 100% of free nucleic acid, more preferably less than about 10%, and most preferably less than about 5% of the nucleic acid in the particle is degraded. "Fully encapsulated" also indicates that the nucleic acid-lipid particles are serum-stable, that is, that they do not rapidly decompose into their component parts upon in vivo administration.

In the context of nucleic acids, full encapsulation may be determined by performing a membrane-impermeable fluorescent dye exclusion assay, which uses a dye that has enhanced fluorescence when associated with nucleic acid. Specific dyes such as OliGreen® and RiboGreen® (Invitrogen Corp.; Carlsbad, Calif.) are available for the quantitative determination of plasmid DNA, single-stranded deoxyribonucleotides, and/or single- or double-stranded ribonucleotides. Encapsulation is determined by adding the dye to a liposomal formulation, measuring the resulting fluorescence, and comparing it to the fluorescence observed upon addition of a small amount of nonionic detergent. Detergent-mediated disruption of the liposomal bilayer releases the encapsulated nucleic acid, allowing it to interact with the membrane-impermeable dye. Nucleic acid encapsulation may be calculated as $E=(I_o-I)/I_o$, where I and $I_o$ refer to the fluorescence intensities before and after the addition of detergent (see, Wheeler et al., *Gene Ther.*, 6:271-281 (1999)).

In other embodiments, the present invention provides a nucleic acid-lipid particle (e.g., SNALP) composition comprising a plurality of nucleic acid-lipid particles.

In some instances, the SNALP composition comprises nucleic acid that is fully encapsulated within the lipid portion of the particles, such that from about 30% to about 100%, from about 40% to about 100%, from about 50% to about 100%, from about 60% to about 100%, from about 70% to about 100%, from about 80% to about 100%, from about 90% to about 100%, from about 30% to about 95%, from about 40% to about 95%, from about 50% to about 95%, from about 60% to about 95%, from about 70% to about 95%, from about 80% to about 95%, from about 85% to about 95%, from about 90% to about 95%, from about 30% to about 90%, from about 40% to about 90%, from about 50% to about 90%, from about 60% to about 90%, from about 70% to about 90%, from about 80% to about 90%, or at least about 30%, 35%, 40%, 45%, 50%, 55%, 60%, 65%, 70%, 75%, 80%, 85%, 90%, 91%, 92%, 93%, 94%, 95%, 96%, 97%, 98%, or 99% (or any fraction thereof or range therein) of the particles have the nucleic acid encapsulated therein.

In other instances, the SNALP composition comprises nucleic acid that is fully encapsulated within the lipid portion of the particles, such that from about 30% to about 100%, from about 40% to about 100%, from about 50% to about 100%, from about 60% to about 100%, from about 70% to about 100%, from about 80% to about 100%, from about 90% to about 100%, from about 30% to about 95%, from about 40% to about 95%, from about 50% to about 95%, from about 60% to about 95%, from about 70% to about 95%, from about 80% to about 95%, from about 85% to about 95%, from about 90% to about 95%, from about 30% to about 90%, from about 40% to about 90%, from about 50% to about 90%, from about 60% to about 90%, from about 70% to about 90%, from about 80% to about 90%, or at least about 30%, 35%, 40%, 45%, 50%, 55%, 60%, 65%, 70%, 75%, 80%, 85%, 90%, 91%, 92%, 93%, 94%, 95%, 96%, 97%, 98%, or 99% (or any fraction thereof or range therein) of the input nucleic acid is encapsulated in the particles.

Depending on the intended use of the lipid particles of the invention, the proportions of the components can be varied and the delivery efficiency of a particular formulation can be measured using, e.g., an endosomal release parameter (ERP) assay.

In particular embodiments, the present invention provides a lipid particle (e.g., SNALP) composition comprising a plurality of lipid particles described herein and an antioxidant. In certain instances, the antioxidant in the lipid particle composition reduces, prevents, and/or inhibits the degradation of a cationic lipid (e.g., a polyunsaturated cationic lipid) present in the lipid particle. In instances wherein the active agent is a therapeutic nucleic acid such as an interfering RNA (e.g., siRNA), the antioxidant in the lipid particle composition reduces, prevents, and/or inhibits the degradation of the nucleic acid payload, e.g., by reducing, preventing, and/or inhibiting the oxidation of the cationic lipid, by reducing, preventing, and/or inhibiting the degradation of the nucleic acid payload, by reducing, preventing, and/or inhibiting the desulfurization of a phosphorothioate (PS)-modified nucleic acid payload, and/or by stabilizing both the lipid and nucleic acid components.

Examples of antioxidants include, but are not limited to, metal chelators (e.g., ethylenediaminetetraacetic acid (EDTA), citrate, and the like), primary antioxidants (e.g., vitamin E isomers such as α-tocopherol or a salt thereof, butylated hydroxyanisole (BHA), butylhydroxytoluene (BHT), tert-butylhydroquinone (TBHQ), and the like), secondary antioxidants (e.g., ascorbic acid, ascorbyl palmitate, cysteine, glutathione, α-lipoic acid, and the like), salts thereof, and mixtures thereof. If needed, the antioxidant is typically present in an amount sufficient to prevent, inhibit, and/or reduce the degradation of the cationic lipid and/or active agent present in the lipid particle. In particular embodiments, the antioxidant comprises EDTA or a salt thereof (e.g., from about 20 mM to about 100 mM), alone or in combination with a primary antioxidant such as α-tocopherol or a salt thereof (e.g., from about 0.02 mol % to about 0.5 mol %) and/or secondary antioxidant such as ascorbyl palmitate or a salt thereof (e.g., from about 0.02 mol % to about 5.0 mol %). An antioxidant such as EDTA may be included at any step or at multiple steps in the lipid particle formation process described in Section VI (e.g., prior to, during, and/or after lipid particle formation).

Additional embodiments related to methods of preventing the degradation of cationic lipids and/or active agents (e.g., therapeutic nucleic acids) present in lipid particles, compositions comprising lipid particles stabilized by these methods, methods of making these lipid particles, and methods of delivering and/or administering these lipid particles are described in PCT Application No. PCT/CA2010/001919, filed Dec. 1, 2010, the disclosure of which is herein incorporated by reference in its entirety for all purposes.

In one aspect, the lipid particles of the invention may include a targeting lipid. In some embodiments, the targeting lipid comprises a GalNAc moiety (i.e., an N-galactosamine moiety). As a non-limiting example, a targeting lipid comprising a GalNAc moiety can include those described in U.S. application Ser. No. 12/328,669, filed Dec. 4, 2008, the disclosure of which is herein incorporated by reference in its entirety for all purposes. A targeting lipid can also include any other lipid (e.g., targeting lipid) known in the art, for example, as described in U.S. application Ser. No. 12/328,669 or PCT Publication No. WO 2008/042973, the contents of each of which are incorporated herein by reference in their entirety for all purposes. In some embodiments, the targeting lipid includes a plurality of GalNAc moieties, e.g., two or three GalNAc moieties. In some embodiments, the targeting lipid contains a plurality, e.g., two or three N-acetylgalactosamine (GalNAc) moieties. In some embodiments, the lipid in the targeting lipid is 1,2-Di-O-hexadecyl-sn-glyceride (i.e., DSG). In some embodiments, the targeting lipid includes a PEG moiety (e.g., a PEG moiety having a molecular weight of at least about 500 Da, such as about 1000 Da, 1500 Da, 2000 Da or greater), for example, the targeting moiety is connected to the lipid via a PEG moiety. Examples of GalNAc targeting lipids include, but are not limited to, $(GalNAc)_3$-PEG-DSG, $(GalNAc)_3$-PEG-LCO, and mixtures thereof.

In some embodiments, the targeting lipid includes a folate moiety. For example, a targeting lipid comprising a folate moiety can include those described in U.S. application Ser. No. 12/328,669, the disclosure of which is herein incorporated by reference in its entirety for all purposes. Examples of folate targeting lipids include, but are not limited to, 1,2-distearoyl-sn-glycero-3-phosphoethanolamine-N-[folate(polyethylene glycol)-2000] (ammonium salt) (Folate-PEG-DSPE), Folate-PEG2000-DSG, Folate-PEG3400-DSG, and mixtures thereof.

In another aspect, the lipid particles of the invention may further comprise one or more apolipoproteins. As used herein, the term "apolipoprotein" or "lipoprotein" refers to apolipoproteins known to those of skill in the art and variants and fragments thereof and to apolipoprotein agonists, analogues, or fragments thereof described in, e.g., PCT Publication No. WO 2010/0088537, the disclosure of which is herein incorporated by reference in its entirety for all purposes. Suitable apolipoproteins include, but are not limited to, ApoA-I, ApoA-II, ApoA-IV, ApoA-V, and ApoE (e.g., ApoE2, ApoE3, etc.), and active polymorphic forms, isoforms, variants, and mutants as well as fragments or truncated forms thereof. Isolated ApoE and/or active fragments and polypeptide analogues thereof, including recombinantly produced forms thereof, are described in U.S. Pat. Nos. 5,672,685; 5,525,472; 5,473,039; 5,182,364; 5,177,189; 5,168,045; and 5,116,739, the disclosures of which are herein incorporated by reference in their entirety for all purposes.

A. Cationic Lipids

Any of the novel cationic lipids of Formulas I-III or salts thereof as set forth herein may be used in the lipid particles of the present invention (e.g., SNALP), either alone or in combination with one or more other cationic lipid species or non-cationic lipid species.

Other cationic lipids or salts thereof which may also be included in the lipid particles of the present invention include, but are not limited to, one or more of the cationic lipids of Formulas I-XXII or salts thereof as described in U.S. application Ser. No. 13/077,856, filed Mar. 31, 2011, one or more of the cationic lipids of Formulas I-XIX or salts thereof as described in PCT Application No. PCT/CA2010/001919, filed Dec. 1, 2010, and/or one or more of the cationic lipids of Formula I or salts thereof as described in PCT Application No. PCT/GB2011/000723, entitled "Novel Cationic Lipids and Methods of Use Thereof," filed May 12, 2011, the disclosures of which are herein incorporated by reference in their entirety for all purposes. Non-limiting examples of additional suitable cationic lipids include 1,2-dilinoleyloxy-N,N-dimethylaminopropane (DLinDMA), 1,2-dilinolenyloxy-N,N-dimethylaminopropane (DLenDMA), 2,2-dilinoleyl-4-(2-dimethylaminoethyl)-[1,3]-dioxolane (DLin-K-C2-DMA; "XTC2" or "C2K"), 2,2-dilinoleyl-4-dimethylaminomethyl-[1,3]-dioxolane (DLin-K-DMA), 2,2-dilinoleyl-4-(3-dimethylaminopropyl)[1,3]-dioxolane (DLin-C3-DMA; "C3K"), 2,2-dilinoleyl-4-(4-dimethylaminobutyl)-[1,3]-dioxolane (DLin-K-C4-DMA; "C4K"), 2,2-dilinoleyl-5-dimethylaminomethyl-[1,3]-dioxane (DLin-K6-DMA), 2,2-dilinoleyl-4-N-methylpepiazino-[1,3]-dioxolane (DLin-K-MPZ), 2,2-dioleoyl-4-dimethylaminomethyl-[1,3]-dioxolane (DO-DMA), 2,2-distearoyl-4-dimethylaminomethyl-[1,3]-dioxolane (DS-K-DMA), 2,2-dilinoleyl-4-N-morpholino-[1,3]-dioxolane (DLin-K-MA), 2,2-Dilinoleyl-4-trimethylamino-[1,3]-dioxolane chloride (DLin-K-TMA.Cl), 2,2-dilinoleyl-4,5-bis(dimethylaminomethyl)-[1,3]-dioxolane (DLin-K2-DMA), 2,2-dilinoleyl-4-methylpiperazine-[1,3]-dioxolane (D-Lin-K-N-methyl-piperazine), DLen-C2K-DMA, γ-DLen-C2K-DMA, DPan-C2K-DMA, DPan-C3K-DMA, DLen-C2K-DMA, γ-DLen-C2K-DMA, DPan-C2K-DMA, TLinDMA, C2-TLinDMA, C3-TLinDMA, 1,2-di-γ-linolenyloxy-N,N-dimethylaminopropane (γ-DLenDMA), 1,2-dilinoleyloxy-(N,N-dimethyl)-butyl-4-amine (C2-DLinDMA), 1,2-dilinoleoyloxy-(N,N-dimethyl)-butyl-4-amine (C2-DLinDAP), dilinoleylmethyl-3-dimethylaminopropionate (DLin-M-C2-DMA), (6Z,9Z,28Z,31Z)-heptatriaconta-6,9,28,31-tetraen-19-yl 4-(dimethylamino) butanoate (DLin-M-C3-DMA or "MC3"; also called dilinoleylmethyl 4-(dimethylamino)butanoate), MC3 Ether (3-((6Z,9Z,28Z,31 Z)-heptatriaconta-6,9,28,31-tetraen-19-yloxy)-N,N-dimethylpropan-1-amine; also called dilinoleylmethyl 4-(dimethylamino)propyl ether), MC4 Ether (4-((6Z,9Z,28Z,31 Z)-heptatriaconta-6,9,28,31-tetraen-19-yloxy)-N,N-dimethylbutan-1-amine; also called dilinoleylmethyl 4-(dimethylamino)butyl ether), LenMC3, γ-LenMC3, MC3MC, MC2C, MC2MC, MC3 Thioester, MC3 Alkyne, MC3 Amide, Pan-MC3, Pan-MC4, Pan-MC5, analogs thereof, salts thereof, and mixtures thereof.

Examples of yet additional cationic lipids include, but are not limited to, 1,2-dioeylcarbamoyloxy-3-dimethylaminopropane (DO-C-DAP), 1,2-dimyristoleoyl-3-dimethylaminopropane (DMDAP), 1,2-dioleoyl-3-trimethylaminopropane chloride (DOTAP.Cl), 1,2-dilinoleylcarbamoyloxy-3-dimethylaminopropane (DLin-C-DAP), 1,2-dilinoleyoxy-3-(dimethylamino)acetoxypropane (DLin-DAC), 1,2-dilinoleyoxy-3-morpholinopropane (DLin-MA), 1,2-dilinoleoyl-3-dimethylaminopropane (DLinDAP), 1,2-dilinoleylthio-3-dimethylaminopropane (DLin-S-DMA), 1-linoleoyl-2-linoleyloxy-3-dimethylaminopropane (DLin-2-DMAP), 1,2-dilinoleyloxy-3-trimethylaminopropane chloride salt (DLin-TMA.Cl), 1,2-dilinoleoyl-3-trimethylaminopropane chloride salt (DLin-TAP.Cl), 1,2-dilinoleyloxy-3-(N-methylpiperazino)propane (DLin-MPZ), 3-(N,N-dilinoleylamino)-1,2-propanediol (DLinAP), 3-(N,N-dioleylamino)-1,2-propanedio (DOAP), 1,2-dilinoleyloxo-3-(2-N,N-dimethylamino)ethoxypropane (DLin-EG-DMA), 3-dimethylamino-2-(cholest-5-en-3-beta-oxybutan-4-oxy)-1-(cis,cis-9,12-octadecadienoxy)propane (CLinDMA), 2-[5'-(cholest-5-en-3-beta-oxy)-3'-oxapentoxy)-3-dimethyl-1-(cis,cis-9',1-2'-octadecadienoxy)propane (CpLinDMA), N,N-dimethyl-3,4-dioleyloxybenzylamine (DMOBA), 1,2-N,N'-dioleylcarbamyl-3-dimethylaminopropane (DOcarbDAP), 1,2-N,N'-dilinoleylcarbamyl-3-dimethylaminopropane (DLincarbDAP), N,N-dioleyl-N,N-dimethylammonium chloride (DODAC), 1,2-dioleyloxy-N,N-dimethylaminopropane (DODMA), 1,2-distearyloxy-N,N-dimethylaminopropane (DSDMA), N-(1-(2,3-dioleyloxy)propyl)-N,N,N-trimethylammonium chloride (DOTMA), N,N-distearyl-N,N-dimethylammonium bromide (DDAB), N-(1-(2,3-dioleoyloxy)propyl)-N,N,N-trimethylammonium chloride (DOTAP), 3-(N—(N',N'-dimethylaminoethane)-carbamoyl)cholesterol (DC-Chol), N-(1,2-dimyristyloxyprop-3-yl)-N,N-dimethyl-N-hydroxyethyl ammonium bromide (DMRIE), 2,3-dioleyloxy-N-[2(spermine-carboxamido)ethyl]-N,N-dimethyl-1-propanaminiumtrifluoroacetate (DOSPA), dioctadecylamidoglycyl spermine (DOGS), analogs thereof, salts thereof, and mixtures thereof.

In some embodiments, the additional cationic lipid forms a salt (preferably a crystalline salt) with one or more anions. In one particular embodiment, the additional cationic lipid is the oxalate (e.g., hemioxalate) salt thereof, which is preferably a crystalline salt.

The synthesis of cationic lipids such as DLinDMA and DLenDMA, as well as additional cationic lipids, is described in U.S. Patent Publication No. 20060083780, the disclosure of which is herein incorporated by reference in its entirety for all purposes.

The synthesis of cationic lipids such as DLin-K-C2-DMA, DLin-K-C3-DMA, DLin-K-C4-DMA, DLin-K6-DMA, DLin-K-MPZ, DO-K-DMA, DS-K-DMA, DLin-K-MA, DLin-K-TMA.Cl, DLin-K$^2$-DMA, D-Lin-K-N-methylpiperzine, DLin-M-C2-DMA, DO-C-DAP, DMDAP, and DOTAP.Cl, as well as additional cationic lipids, is described in PCT Publication No. WO 2010/042877, the disclosure of which is incorporated herein by reference in its entirety for all purposes.

The synthesis of cationic lipids such as DLin-K-DMA, DLin-C-DAP, DLinDAC, DLinMA, DLinDAP, DLin-S-DMA, DLin-2-DMAP, DLinTMA.Cl, DLinTAP.Cl, DLinMPZ, DLinAP, DOAP, and DLin-EG-DMA, as well as additional cationic lipids, is described in PCT Publication No. WO 09/086,558, the disclosure of which is herein incorporated by reference in its entirety for all purposes.

The synthesis of cationic lipids such as γ-DLenDMA, DLen-C2K-DMA, γ-DLen-C2K-DMA, DPan-C2K-DMA, DPan-C3K-DMA, DLen-C2K-DMA, γ-DLen-C2K-DMA, DPan-C2K-DMA, TLinDMA, C2-TLinDMA, C3-TLinDMA, C2-DLinDMA, and C2-DLinDAP, as well as additional cationic lipids, is described in PCT Publication No. WO 2011/000106, the disclosure of which is herein incorporated by reference in its entirety for all purposes.

The synthesis of cationic lipids such as MC3 and MC3 analogs such as LenMC3, γ-LenMC3, MC3MC, MC2C, MC2MC, MC3 Thioester, MC3 Ether, MC4 Ether, MC3 Alkyne, MC3 Amide, Pan-MC3, Pan-MC4, and Pan-MC5 is described in PCT Application No. PCT/GB2011/000723, entitled "Novel Cationic Lipids and Methods of Use Thereof," filed May 12, 2011, the disclosure of which is herein incorporated by reference in its entirety for all purposes.

The synthesis of cationic lipids such as CLinDMA, as well as additional cationic lipids, is described in U.S. Patent Publication No. 20060240554, the disclosure of which is herein incorporated by reference in its entirety for all purposes.

The synthesis of a number of other cationic lipids and related analogs has been described in U.S. Pat. Nos. 5,208,036; 5,264,618; 5,279,833; 5,283,185; 5,753,613; and 5,785,992; and PCT Publication No. WO 96/10390, the disclosures of which are each herein incorporated by reference in their entirety for all purposes. Additionally, a number of commercial preparations of cationic lipids can be used, such as, e.g., LIPOFECTIN® (including DOTMA and DOPE, available from GIBCO/BRL); LIPOFECTAMINE® (including DOSPA and DOPE, available from GIBCO/BRL); and TRANSFECTAM® (including DOGS, available from Promega Corp.).

The synthesis of additional cationic lipids suitable for use in the lipid particles of the present invention is described in PCT Publication Nos. WO 2010/054401, WO 2010/054405, WO 2010/054406, WO 2010/054384, and WO 2010/144740; U.S. Patent Publication No. 20090023673; and U.S. Provisional Application No. 61/287,995, entitled "Methods and Compositions for Delivery of Nucleic Acids," filed Dec. 18, 2009, the disclosures of which are herein incorporated by reference in their entirety for all purposes.

In some embodiments, the cationic lipid comprises from about 45 mol % to about 90 mol %, from about 45 mol % to about 85 mol %, from about 45 mol % to about 80 mol %, from about 45 mol % to about 75 mol %, from about 45 mol % to about 70 mol %, from about 45 mol % to about 65 mol %, from about 45 mol % to about 60 mol %, from about 45 mol % to about 55 mol %, from about 50 mol % to about 90 mol %, from about 50 mol % to about 85 mol %, from about 50 mol % to about 80 mol %, from about 50 mol % to about 75 mol %, from about 50 mol % to about 70 mol %, from about 50 mol % to about 65 mol %, from about 50 mol % to about 60 mol %, from about 55 mol % to about 65 mol % or from about 55 mol % to about 70 mol % (or any fraction thereof or range therein) of the total lipid present in the particle.

In certain preferred embodiments, the cationic lipid comprises from about 50 mol % to about 58 mol %, from about 51 mol % to about 59 mol %, from about 51 mol % to about 58 mol %, from about 51 mol % to about 57 mol %, from about 52 mol % to about 58 mol %, from about 52 mol % to about 57 mol %, from about 52 mol % to about 56 mol %, or from about 53 mol % to about 55 mol % (or any fraction thereof or range therein) of the total lipid present in the particle. In particular embodiments, the cationic lipid comprises about 50 mol %, 51 mol %, 52 mol %, 53 mol %, 54 mol %, 55 mol %, 56 mol %, 57 mol %, 58 mol %, 59 mol %, 60 mol %, 61 mol %, 62 mol %, 63 mol %, 64 mol %, or 65 mol % (or any fraction thereof or range therein) of the total lipid present in the particle. In other embodiments, the cationic lipid comprises (at least) about 66, 67, 68, 69, 70, 71, 72, 73, 74, 75, 76, 77, 78, 79, 80, 81, 82, 83, 84, 85, 86, 87, 88, 89, or 90 mol % (or any fraction thereof or range therein) of the total lipid present in the particle.

In additional embodiments, the cationic lipid comprises from about 2 mol % to about 60 mol %, from about 5 mol % to about 50 mol %, from about 10 mol % to about 50 mol %, from about 20 mol % to about 50 mol %, from about 20 mol % to about 40 mol %, from about 30 mol % to about 40 mol %, or about 40 mol % (or any fraction thereof or range therein) of the total lipid present in the particle.

Additional percentages and ranges of cationic lipids suitable for use in the lipid particles of the present invention are described in PCT Publication No. WO 09/127,060, U.S. Publication No. 20110071208, and U.S. Publication No. 20110076335, the disclosures of which are herein incorporated by reference in their entirety for all purposes.

It should be understood that the percentage of cationic lipid present in the lipid particles of the invention is a target amount, and that the actual amount of cationic lipid present in the formulation may vary, for example, by ±5 mol %. For example, in the 1:57 lipid particle (e.g., SNALP) formulation, the target amount of cationic lipid is 57.1 mol %, but the actual amount of cationic lipid may be ±5 mol %, ±4 mol %, ±3 mol %, ±2 mol %, ±1 mol %, ±0.75 mol %, ±0.5 mol %, ±0.25 mol %, or ±0.1 mol % of that target amount, with the balance of the formulation being made up of other lipid components (adding up to 100 mol % of total lipids present in the particle). Similarly, in the 7:54 lipid particle (e.g., SNALP) formulation, the target amount of cationic lipid is 54.06 mol %, but the actual amount of cationic lipid may be ±5 mol %, ±4 mol %, ±3 mol %, ±2 mol %, ±1 mol %, ±0.75 mol %, ±0.5 mol %, ±0.25 mol %, or ±0.1 mol % of that target amount, with the balance of the formulation being made up of other lipid components (adding up to 100 mol % of total lipids present in the particle).

B. Non-Cationic Lipids

The non-cationic lipids used in the lipid particles of the invention (e.g., SNALP) can be any of a variety of neutral uncharged, zwitterionic, or anionic lipids capable of producing a stable complex.

Non-limiting examples of non-cationic lipids include phospholipids such as lecithin, phosphatidylethanolamine, lysolecithin, lysophosphatidylethanolamine, phosphatidylserine, phosphatidylinositol, sphingomyelin, egg sphingomyelin (ESM), cephalin, cardiolipin, phosphatidic acid, cerebrosides, dicetylphosphate, distearoylphosphatidylcholine (DSPC), dioleoylphosphatidylcholine (DOPC), dipalmitoylphosphatidylcholine (DPPC), dioleoylphosphatidylglycerol (DOPG), dipalmitoylphosphatidylglycerol (DPPG), dioleoylphosphatidylethanolamine (DOPE), palmitoyloleoyl-phosphatidylcholine (POPC), palmitoyloleoyl-phosphatidylethanolamine (POPE), palmitoyloleoyl-phosphatidylglycerol (POPG), dioleoylphosphatidylethanolamine 4-(N-maleimidomethyl)-cyclohexane-1-carboxylate (DOPE-mal), dipalmitoyl-phosphatidylethanolamine (DPPE), dimyristoyl-phosphatidylethanolamine (DMPE), distearoyl-phosphatidylethanolamine (DSPE), monomethyl-phosphatidylethanolamine, dimethyl-phosphatidylethanolamine, dielaidoyl-phosphatidylethanolamine (DEPE), stearoyloleoyl-phosphatidylethanolamine (SOPE), lysophosphatidylcholine, dilinoleoylphosphatidylcholine, and mixtures thereof. Other diacylphosphatidylcholine and diacylphosphatidylethanolamine phospholipids can also be used. The acyl groups in these lipids are preferably acyl groups derived from fatty acids having $C_{10}$-$C_{24}$ carbon chains, e.g., lauroyl, myristoyl, palmitoyl, stearoyl, or oleoyl.

Additional examples of non-cationic lipids include sterols such as cholesterol and derivatives thereof. Non-limiting examples of cholesterol derivatives include polar analogues such as 5α-cholestanol, 5β-coprostanol, cholesteryl-(2'-hydroxy)-ethyl ether, cholesteryl-(4'-hydroxy)-butyl ether, and 6-ketocholestanol; non-polar analogues such as 5α-cholestane, cholestenone, 5α-cholestanone, 5β-cholestanone, and cholesteryl decanoate; and mixtures thereof. In preferred embodiments, the cholesterol derivative is a polar analogue such as cholesteryl-(4'-hydroxy)-butyl ether. The synthesis of cholesteryl-(2'-hydroxy)-ethyl ether is described in PCT Publication No. WO 09/127,060, the disclosure of which is herein incorporated by reference in its entirety for all purposes.

In some embodiments, the non-cationic lipid present in the lipid particles (e.g., SNALP) comprises or consists of a mixture of one or more phospholipids and cholesterol or a derivative thereof. In other embodiments, the non-cationic lipid present in the lipid particles (e.g., SNALP) comprises or consists of one or more phospholipids, e.g., a cholesterol-free lipid particle formulation. In yet other embodiments, the non-cationic lipid present in the lipid particles (e.g., SNALP) comprises or consists of cholesterol or a derivative thereof, e.g., a phospholipid-free lipid particle formulation.

Other examples of non-cationic lipids suitable for use in the present invention include nonphosphorous containing lipids such as, e.g., stearylamine, dodecylamine, hexadecylamine, acetyl palmitate, glycerolricinoleate, hexadecyl stereate, isopropyl myristate, amphoteric acrylic polymers, triethanolamine-lauryl sulfate, alkyl-aryl sulfate polyethyloxylated fatty acid amides, dioctadecyldimethyl ammonium bromide, ceramide, sphingomyelin, and the like.

In some embodiments, the non-cationic lipid comprises from about 10 mol % to about 60 mol %, from about 20 mol % to about 55 mol %, from about 20 mol % to about 45 mol %, from about 20 mol % to about 40 mol %, from about 25 mol % to about 50 mol %, from about 25 mol % to about 45 mol %, from about 30 mol % to about 50 mol %, from about 30 mol % to about 45 mol %, from about 30 mol % to about 40 mol %, from about 35 mol % to about 45 mol %, from about 37 mol % to about 42 mol %, or about 35 mol %, 36 mol %, 37 mol %, 38 mol %, 39 mol %, 40 mol %, 41 mol %, 42 mol %, 43 mol %, 44 mol %, or 45 mol % (or any fraction thereof or range therein) of the total lipid present in the particle.

In embodiments where the lipid particles contain a mixture of phospholipid and cholesterol or a cholesterol derivative, the mixture may comprise up to about 40 mol %, 45 mol %, 50 mol %, 55 mol %, or 60 mol % of the total lipid present in the particle.

In some embodiments, the phospholipid component in the mixture may comprise from about 2 mol % to about 20 mol %, from about 2 mol % to about 15 mol %, from about 2 mol % to about 12 mol %, from about 4 mol % to about 15 mol %, or from about 4 mol % to about 10 mol % (or any fraction thereof or range therein) of the total lipid present in the particle. In certain preferred embodiments, the phospholipid component in the mixture comprises from about 5 mol % to about 10 mol %, from about 5 mol % to about 9 mol %, from about 5 mol % to about 8 mol %, from about 6 mol % to about 9 mol %, from about 6 mol % to about 8 mol %, or about 5 mol %, 6 mol %, 7 mol %, 8 mol %, 9 mol %, or 10 mol % (or any fraction thereof or range therein) of the total lipid present in the particle. As a non-limiting example, a 1:57 lipid particle formulation comprising a mixture of phospholipid and cholesterol may comprise a phospholipid such as DPPC or DSPC at about 7 mol % (or any fraction thereof), e.g., in a mixture with cholesterol or a cholesterol derivative at about 34 mol % (or any fraction thereof) of the total lipid present in the particle. As another non-limiting example, a 7:54 lipid particle formulation comprising a mixture of phospholipid and cholesterol may comprise a phospholipid such as DPPC or DSPC at about 7 mol % (or any fraction thereof), e.g., in a mixture with cholesterol or a cholesterol derivative at about 32 mol % (or any fraction thereof) of the total lipid present in the particle.

In other embodiments, the cholesterol component in the mixture may comprise from about 25 mol % to about 45 mol %, from about 25 mol % to about 40 mol %, from about 30 mol % to about 45 mol %, from about 30 mol % to about 40 mol %, from about 27 mol % to about 37 mol %, from about 25 mol % to about 30 mol %, or from about 35 mol % to about 40 mol % (or any fraction thereof or range therein) of the total lipid present in the particle. In certain preferred embodiments, the cholesterol component in the mixture comprises from about 25 mol % to about 35 mol %, from about 27 mol % to about 35 mol %, from about 29 mol % to about 35 mol %, from about 30 mol % to about 35 mol %, from about 30 mol % to about 34 mol %, from about 31 mol % to about 33 mol %, or about 30 mol %, 31 mol %, 32 mol %, 33 mol %, 34 mol %, or 35 mol % (or any fraction thereof or range therein) of the total lipid present in the particle. In other embodiments, the cholesterol component in the mixture comprises about 36, 37, 38, 39, 40, 41, 42, 43, 44, or 45 mol % (or any fraction thereof or range therein) of the total lipid present in the particle. Typically, a 1:57 lipid particle formulation comprising a mixture of phospholipid and cholesterol may comprise cholesterol or a cholesterol derivative at about 34 mol % (or any fraction thereof), e.g., in a mixture with a phospholipid such as DPPC or DSPC at about 7 mol % (or any fraction thereof) of the total lipid present in the particle. Typically, a 7:54 lipid particle formulation comprising a mixture of phospholipid and cholesterol may comprise cholesterol or a cholesterol derivative at about 32 mol % (or any fraction thereof), e.g., in a mixture with a phospholipid such as DPPC or DSPC at about 7 mol % (or any fraction thereof) of the total lipid present in the particle.

In embodiments where the lipid particles are phospholipid-free, the cholesterol or derivative thereof may comprise up to about 25 mol %, 30 mol %, 35 mol %, 40 mol %, 45 mol %, 50 mol %, 55 mol %, or 60 mol % of the total lipid present in the particle.

In some embodiments, the cholesterol or derivative thereof in the phospholipid-free lipid particle formulation may comprise from about 25 mol % to about 45 mol %, from about 25 mol % to about 40 mol %, from about 30 mol % to about 45 mol %, from about 30 mol % to about 40 mol %, from about 31 mol % to about 39 mol %, from about 32 mol % to about 38 mol %, from about 33 mol % to about 37 mol %, from about 35 mol % to about 45 mol %, from about 30 mol % to about 35 mol %, from about 35 mol % to about 40 mol %, or about 30 mol %, 31 mol %, 32 mol %, 33 mol %, 34 mol %, 35 mol %, 36 mol %, 37 mol %, 38 mol %, 39 mol %, 40 mol %, 41 mol %, 42 mol %, 43 mol %, 44 mol %, or 45 mol % (or any fraction thereof or range therein) of the total lipid present in the particle. As a non-limiting example, a 1:62 lipid particle formulation may comprise cholesterol at about 37 mol % (or any fraction thereof) of the total lipid present in the particle. As another non-limiting example, a 7:58 lipid particle formulation may comprise cholesterol at about 35 mol % (or any fraction thereof) of the total lipid present in the particle.

In other embodiments, the non-cationic lipid comprises from about 5 mol % to about 90 mol %, from about 10 mol % to about 85 mol %, from about 20 mol % to about 80 mol %, about 10 mol % (e.g., phospholipid only), or about 60 mol % (e.g., phospholipid and cholesterol or derivative thereof) (or any fraction thereof or range therein) of the total lipid present in the particle.

Additional percentages and ranges of non-cationic lipids suitable for use in the lipid particles of the present invention are described in PCT Publication No. WO 09/127,060, U.S. Publication No. 20110071208, and U.S. Publication No. 20110076335, the disclosures of which are herein incorporated by reference in their entirety for all purposes.

It should be understood that the percentage of non-cationic lipid present in the lipid particles of the invention is a target amount, and that the actual amount of non-cationic lipid present in the formulation may vary, for example, by t 5 mol %. For example, in the 1:57 lipid particle (e.g., SNALP) formulation, the target amount of phospholipid is 7.1 mol % and the target amount of cholesterol is 34.3 mol %, but the actual amount of phospholipid may be ±2 mol %, ±1.5 mol %, ±1 mol %, ±0.75 mol %, ±0.5 mol %, ±0.25 mol %, or ±0.1 mol % of that target amount, and the actual amount of cholesterol may be ±3 mol %, ±2 mol %, ±1 mol %, ±0.75 mol %, ±0.5 mol %, ±0.25 mol %, or ±0.1 mol % of that target amount, with the balance of the formulation being made up of other lipid components (adding up to 100 mol % of total lipids present in the particle). Similarly, in the 7:54 lipid particle (e.g., SNALP) formulation, the target amount of phospholipid is 6.75 mol % and the target amount of cholesterol is 32.43 mol %, but the actual amount of phospholipid may be ±2 mol %, ±1.5 mol %, ±1 mol %, ±0.75 mol %, ±0.5 mol %, ±0.25 mol %, or ±0.1 mol % of that target amount, and the actual amount of cholesterol may be ±3 mol %, ±2 mol %, ±1 mol %, ±0.75 mol %, ±0.5 mol %, ±0.25 mol %, or ±0.1 mol % of that target amount, with the balance of the formulation being made up of other lipid components (adding up to 100 mol % of total lipids present in the particle).

C. Lipid Conjugates

In addition to cationic and non-cationic lipids, the lipid particles of the invention (e.g., SNALP) may further comprise a lipid conjugate. The conjugated lipid is useful in that it prevents the aggregation of particles. Suitable conjugated lipids include, but are not limited to, PEG-lipid conjugates, POZ-lipid conjugates, ATTA-lipid conjugates, cationic-polymer-lipid conjugates (CPLs), and mixtures thereof. In certain embodiments, the lipid particles comprise either a PEG-lipid conjugate or an ATTA-lipid conjugate together with a CPL. The term "ATTA" or "polyamide" includes, without limitation, compounds described in U.S. Pat. Nos. 6,320,017 and 6,586,559, the disclosures of which are herein incorporated by reference in their entirety for all purposes.

In a preferred embodiment, the lipid conjugate is a PEG-lipid. Examples of PEG-lipids include, but are not limited to, PEG coupled to dialkyloxypropyls (PEG-DAA) as described in, e.g., PCT Publication No. WO 05/026372, PEG coupled to diacylglycerol (PEG-DAG) as described in, e.g., U.S. Patent Publication Nos. 20030077829 and 2005008689, PEG coupled to phospholipids such as phosphatidylethanolamine (PEG-PE), PEG conjugated to ceramides as described in, e.g., U.S. Pat. No. 5,885,613, PEG conjugated to cholesterol or a derivative thereof, and mixtures thereof. The disclosures of these patent documents are herein incorporated by reference in their entirety for all purposes.

Additional PEG-lipids suitable for use in the invention include, without limitation, mPEG2000-1,2-di-O-alkyl-sn3-carbomoylglyceride (PEG-C-DOMG). The synthesis of PEG-C-DOMG is described in PCT Publication No. WO 09/086,558, the disclosure of which is herein incorporated by reference in its entirety for all purposes. Yet additional suitable PEG-lipid conjugates include, without limitation, 1-[8'-(1,2-dimyristoyl-3-propanoxy)-carboxamido-3',6'-dioxaoctanyl]carbamoyl-ω-methyl-poly(ethylene glycol) (2 KPEG-DMG). The synthesis of 2 KPEG-DMG is described in U.S. Pat. No. 7,404,969, the disclosure of which is herein incorporated by reference in its entirety for all purposes.

PEG is a linear, water-soluble polymer of ethylene PEG repeating units with two terminal hydroxyl groups. PEGs are classified by their molecular weights; for example, PEG 2000 has an average molecular weight of about 2,000 daltons, and PEG 5000 has an average molecular weight of about 5,000 daltons. PEGs are commercially available from Sigma Chemical Co. and other companies and include, but are not limited to, the following: monomethoxypolyethylene glycol (MePEG-OH), monomethoxypolyethylene glycol-succinate (MePEG-S), monomethoxypolyethylene glycol-succinimidyl succinate (MePEG-S—NHS), monomethoxypolyethylene glycol-amine (MePEG-NH$_2$), monomethoxypolyethylene glycol-tresylate (MePEG-TRES), monomethoxypolyethylene glycol-imidazolyl-carbonyl (MePEG-IM), as well as such compounds containing a terminal hydroxyl group instead of a terminal methoxy group (e.g., HO-PEG-S, HO-PEG-S—NHS, HO-PEG-NH$_2$, etc.). Other PEGs such as those described in U.S. Pat. Nos. 6,774,180 and 7,053,150 (e.g., mPEG (20 KDa) amine) are also useful for preparing the PEG-lipid conjugates of the present invention. The disclosures of these patents are herein incorporated by reference in their entirety for all purposes. In addition, monomethoxypolyethyleneglycol-acetic acid (MePEG-CH$_2$COOH) is particularly useful for preparing PEG-lipid conjugates including, e.g., PEG-DAA conjugates.

The PEG moiety of the PEG-lipid conjugates described herein may comprise an average molecular weight ranging from about 550 daltons to about 10,000 daltons. In certain instances, the PEG moiety has an average molecular weight of from about 750 daltons to about 5,000 daltons (e.g., from about 1,000 daltons to about 5,000 daltons, from about 1,500 daltons to about 3,000 daltons, from about 750 daltons to about 3,000 daltons, from about 750 daltons to about 2,000 daltons, etc.). In other instances, the PEG moiety has an average molecular weight of from about 550 daltons to about 1000 daltons, from about 250 daltons to about 1000 daltons, from about 400 daltons to about 1000 daltons, from about 600 daltons to about 900 daltons, from about 700 daltons to about 800 daltons, or about 200, 250, 300, 350, 400, 450, 500, 550, 600, 650, 700, 750, 800, 850, 900, 950, or 1000 daltons. In preferred embodiments, the PEG moiety has an average molecular weight of about 2,000 daltons or about 750 daltons.

In certain instances, the PEG can be optionally substituted by an alkyl, alkoxy, acyl, or aryl group. The PEG can be conjugated directly to the lipid or may be linked to the lipid via a linker moiety. Any linker moiety suitable for coupling the PEG to a lipid can be used including, e.g., non-ester containing linker moieties and ester-containing linker moieties. In a preferred embodiment, the linker moiety is a non-ester containing linker moiety. As used herein, the term "non-ester containing linker moiety" refers to a linker moiety that does not contain a carboxylic ester bond (—OC(O)—). Suitable non-ester containing linker moieties include, but are not limited to, amido (—C(O)NH—), amino (—NR—), carbonyl (—C(O)—), carbamate (—NHC(O)O—), urea (—NHC(O)NH—), disulphide (—S—S—), ether (—O—), succinyl (—(O)CCH$_2$CH$_2$C(O)—), succinamidyl (—NHC(O)CH$_2$CH$_2$C(O)NH—), ether, disulphide, as well as combinations thereof (such as a linker containing both a carbamate linker moiety and an amido linker moiety). In a preferred embodiment, a carbamate linker is used to couple the PEG to the lipid.

In other embodiments, an ester containing linker moiety is used to couple the PEG to the lipid. Suitable ester containing linker moieties include, e.g., carbonate (—OC(O)O—), succinoyl, phosphate esters (—O—(O)POH—O—), sulfonate esters, and combinations thereof.

Phosphatidylethanolamines having a variety of acyl chain groups of varying chain lengths and degrees of saturation can be conjugated to PEG to form the lipid conjugate. Such phosphatidylethanolamines are commercially available, or can be isolated or synthesized using conventional techniques known to those of skilled in the art. Phosphatidylethanolamines containing saturated or unsaturated fatty acids with carbon chain lengths in the range of $C_{10}$ to $C_{20}$ are preferred. Phosphatidylethanolamines with mono- or diunsaturated fatty acids and mixtures of saturated and unsaturated fatty acids can also be used. Suitable phosphatidylethanolamines include, but are not limited to, dimyristoyl-phosphatidylethanolamine (DMPE), dipalmitoyl-phosphatidylethanolamine (DPPE), dioleoylphosphatidylethanolamine (DOPE), and distearoyl-phosphatidylethanolamine (DSPE).

The term "diacylglycerol" or "DAG" includes a compound having 2 fatty acyl chains, $R^1$ and $R^2$, both of which have independently between 2 and 30 carbons bonded to the 1- and 2-position of glycerol by ester linkages. The acyl groups can be saturated or have varying degrees of unsaturation. Suitable acyl groups include, but are not limited to, lauroyl ($C_{12}$), myristoyl ($C_{14}$), palmitoyl ($C_{16}$), stearoyl ($C_{18}$), and icosyl ($C_{20}$). In preferred embodiments, $R^1$ and $R^2$ are the same, i.e., $R^1$ and $R^2$ are both myristoyl (i.e., dimyristoyl), $R^1$ and $R^2$ are both stearoyl (i.e., distearoyl), etc. Diacylglycerols have the following general formula:

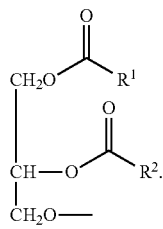

(IV)

The term "dialkyloxypropyl" or "DAA" includes a compound having 2 alkyl chains, $R^1$ and $R^2$, both of which have independently between 2 and 30 carbons. The alkyl groups can be saturated or have varying degrees of unsaturation. Dialkyloxypropyls have the following general formula:

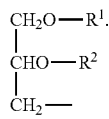

(V)

In a preferred embodiment, the PEG-lipid is a PEG-DAA conjugate having the following formula:

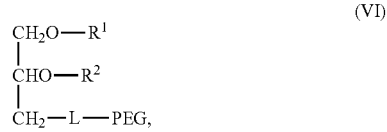

(VI)

wherein $R^1$ and $R^2$ are independently selected and are long-chain alkyl groups having from about 10 to about 22 carbon atoms; PEG is a polyethyleneglycol; and L is a non-ester containing linker moiety or an ester containing linker moiety as described above. The long-chain alkyl groups can be saturated or unsaturated. Suitable alkyl groups include, but are not limited to, decyl ($C_{10}$), lauryl ($C_{12}$), myristyl ($C_{14}$), palmityl ($C_{16}$), stearyl ($C_{18}$), and icosyl ($C_{20}$). In preferred embodiments, $R^1$ and $R^2$ are the same, i.e., $R^1$ and $R^2$ are both myristyl (i.e., dimyristyl), $R^1$ and $R^2$ are both stearyl (i.e., distearyl), etc.

In Formula VI above, the PEG has an average molecular weight ranging from about 550 daltons to about 10,000 daltons. In certain instances, the PEG has an average molecular weight of from about 750 daltons to about 5,000 daltons (e.g., from about 1,000 daltons to about 5,000 daltons, from about 1,500 daltons to about 3,000 daltons, from about 750 daltons to about 3,000 daltons, from about 750 daltons to about 2,000 daltons, etc.). In other instances, the PEG moiety has an average molecular weight of from about 550 daltons to about 1000 daltons, from about 250 daltons to about 1000 daltons, from about 400 daltons to about 1000 daltons, from about 600 daltons to about 900 daltons, from about 700 daltons to about 800 daltons, or about 200, 250, 300, 350, 400, 450, 500, 550, 600, 650, 700, 750, 800, 850, 900, 950, or 1000 daltons. In preferred embodiments, the PEG has an average molecular weight of about 2,000 daltons or about 750 daltons. The PEG can be optionally substituted with alkyl, alkoxy, acyl, or aryl groups. In certain embodiments, the terminal hydroxyl group is substituted with a methoxy or methyl group.

In a preferred embodiment, "L" is a non-ester containing linker moiety. Suitable non-ester containing linkers include, but are not limited to, an amido linker moiety, an amino linker moiety, a carbonyl linker moiety, a carbamate linker moiety, a urea linker moiety, an ether linker moiety, a disulphide linker moiety, a succinamidyl linker moiety, and combinations thereof. In a preferred embodiment, the non-ester containing linker moiety is a carbamate linker moiety (i.e., a PEG-C-DAA conjugate). In another preferred embodiment, the non-ester containing linker moiety is an amido linker moiety (i.e., a PEG-A-DAA conjugate). In yet another preferred embodiment, the non-ester containing linker moiety is a succinamidyl linker moiety (i.e., a PEG-S-DAA conjugate).

In particular embodiments, the PEG-lipid conjugate is selected from:

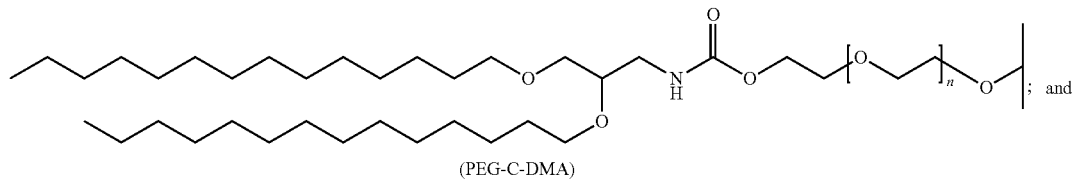

(PEG-C-DMA)

; and

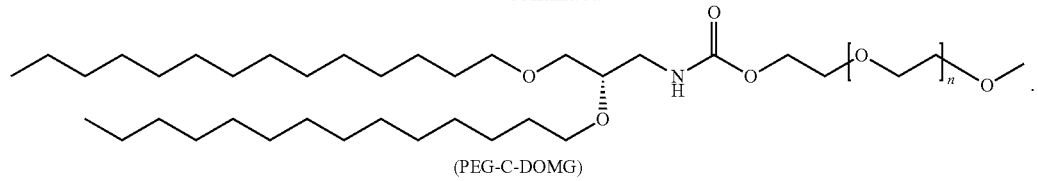

(PEG-C-DOMG)

The PEG-DAA conjugates are synthesized using standard techniques and reagents known to those of skill in the art. It will be recognized that the PEG-DAA conjugates will contain various amide, amine, ether, thio, carbamate, and urea linkages. Those of skill in the art will recognize that methods and reagents for forming these bonds are well known and readily available. See, e.g., March, ADVANCED ORGANIC CHEMISTRY (Wiley 1992); Larock, COMPREHENSIVE ORGANIC TRANSFORMATIONS (VCH 1989); and Furniss, VOGEL'S TEXTBOOK OF PRACTICAL ORGANIC CHEMISTRY, 5th ed. (Longman 1989). It will also be appreciated that any functional groups present may require protection and deprotection at different points in the synthesis of the PEG-DAA conjugates. Those of skill in the art will recognize that such techniques are well known. See, e.g., Green and Wuts, PROTECTIVE GROUPS IN ORGANIC SYNTHESIS (Wiley 1991).

Preferably, the PEG-DAA conjugate is a PEG-didecyloxypropyl ($C_{10}$) conjugate, a PEG-dilauryloxypropyl ($C_{12}$) conjugate, a PEG-dimyristyloxypropyl ($C_{14}$) conjugate, a PEG-dipalmityloxypropyl ($C_{16}$) conjugate, or a PEG-distearyloxypropyl ($C_{18}$) conjugate. In these embodiments, the PEG preferably has an average molecular weight of about 750 or about 2,000 daltons. In one particularly preferred embodiment, the PEG-lipid conjugate comprises PEG2000-C-DMA, wherein the "2000" denotes the average molecular weight of the PEG, the "C" denotes a carbamate linker moiety, and the "DMA" denotes dimyristyloxypropyl. In another particularly preferred embodiment, the PEG-lipid conjugate comprises PEG750-C-DMA, wherein the "750" denotes the average molecular weight of the PEG, the "C" denotes a carbamate linker moiety, and the "DMA" denotes dimyristyloxypropyl. In particular embodiments, the terminal hydroxyl group of the PEG is substituted with a methyl group. Those of skill in the art will readily appreciate that other dialkyloxypropyls can be used in the PEG-DAA conjugates of the present invention.

In addition to the foregoing, it will be readily apparent to those of skill in the art that other hydrophilic polymers can be used in place of PEG. Examples of suitable polymers that can be used in place of PEG include, but are not limited to, polyvinylpyrrolidone, polymethyloxazoline, polyethyloxazoline, polyhydroxypropyl methacrylamide, polymethacrylamide and polydimethylacrylamide, polylactic acid, polyglycolic acid, and derivatized celluloses such as hydroxymethylcellulose or hydroxyethylcellulose.

In addition to the foregoing components, the lipid particles (e.g., SNALP) of the present invention can further comprise cationic poly(ethylene glycol) (PEG) lipids or CPLs (see, e.g., Chen et al., Bioconj. Chem., 11:433-437 (2000); U.S. Pat. No. 6,852,334; PCT Publication No. WO 00/62813, the disclosures of which are herein incorporated by reference in their entirety for all purposes).

In some embodiments, the lipid conjugate (e.g., PEG-lipid) comprises from about 0.1 mol % to about 2 mol %, from about 0.5 mol % to about 2 mol %, from about 1 mol % to about 2 mol %, from about 0.6 mol % to about 1.9 mol %, from about 0.7 mol % to about 1.8 mol %, from about 0.8 mol % to about 1.7 mol %, from about 0.9 mol % to about 1.6 mol %, from about 0.9 mol % to about 1.8 mol %, from about 1 mol % to about 1.8 mol %, from about 1 mol % to about 1.7 mol %, from about 1.2 mol % to about 1.8 mol %, from about 1.2 mol % to about 1.7 mol %, from about 1.3 mol % to about 1.6 mol %, from about 1.4 mol % to about 1.5 mol %, or about 1, 1.1, 1.2, 1.3, 1.4, 1.5, 1.6, 1.7, 1.8, 1.9, or 2 mol % (or any fraction thereof or range therein) of the total lipid present in the particle.

In other embodiments, the lipid conjugate (e.g., PEG-lipid) comprises from about 0 mol % to about 20 mol %, from about 0.5 mol % to about 20 mol %, from about 2 mol % to about 20 mol %, from about 1.5 mol % to about 18 mol %, from about 2 mol % to about 15 mol %, from about 4 mol % to about 15 mol %, from about 2 mol % to about 12 mol %, from about 5 mol % to about 12 mol %, or about 2 mol % (or any fraction thereof or range therein) of the total lipid present in the particle.

In further embodiments, the lipid conjugate (e.g., PEG-lipid) comprises from about 4 mol % to about 10 mol %, from about 5 mol % to about 10 mol %, from about 5 mol % to about 9 mol %, from about 5 mol % to about 8 mol %, from about 6 mol % to about 9 mol %, from about 6 mol % to about 8 mol %, or about 5 mol %, 6 mol %, 7 mol %, 8 mol %, 9 mol %, or 10 mol % (or any fraction thereof or range therein) of the total lipid present in the particle.

Additional examples, percentages, and/or ranges of lipid conjugates suitable for use in the lipid particles of the invention are described in PCT Publication No. WO 09/127,060, U.S. Publication No. 20110071208, U.S. Publication No. 20110076335, U.S. application Ser. No. 13/006,277, filed Jan. 13, 2011, and PCT Publication No. WO 2010/006282, the disclosures of which are herein incorporated by reference in their entirety for all purposes.

It should be understood that the percentage of lipid conjugate (e.g., PEG-lipid) present in the lipid particles of the invention is a target amount, and that the actual amount of lipid conjugate present in the formulation may vary, for example, by ±2 mol %. For example, in the 1:57 lipid particle (e.g., SNALP) formulation, the target amount of lipid conjugate is 1.4 mol %, but the actual amount of lipid conjugate may be ±0.5 mol %, ±0.4 mol %, ±0.3 mol %, ±0.2 mol %, ±0.1 mol %, or ±0.05 mol % of that target amount, with the balance of the formulation being made up of other lipid components (adding up to 100 mol % of total lipids present in the particle). Similarly, in the 7:54 lipid particle (e.g., SNALP) formulation, the target amount of lipid conjugate is 6.76 mol %, but the actual amount of lipid conjugate may be ±2 mol %, ±1.5 mol %, ±1 mol %, ±0.75 mol %, ±0.5 mol %, ±0.25 mol %, or ±0.1 mol % of that target amount, with the balance of the formulation being made up of other lipid components (adding up to 100 mol % of total lipids present in the particle).

One of ordinary skill in the art will appreciate that the concentration of the lipid conjugate can be varied depending on the lipid conjugate employed and the rate at which the lipid particle is to become fusogenic.

By controlling the composition and concentration of the lipid conjugate, one can control the rate at which the lipid conjugate exchanges out of the lipid particle and, in turn, the rate at which the lipid particle becomes fusogenic. For instance, when a PEG-DAA conjugate is used as the lipid conjugate, the rate at which the lipid particle becomes fusogenic can be varied, for example, by varying the concentration of the lipid conjugate, by varying the molecular weight of the PEG, or by varying the chain length and degree of saturation of the alkyl groups on the PEG-DAA conjugate. In addition, other variables including, for example, pH, temperature, ionic strength, etc. can be used to vary and/or control the rate at which the lipid particle becomes fusogenic. Other methods which can be used to control the rate at which the lipid particle becomes fusogenic will become apparent to those of skill in the art upon reading this disclosure. Also, by controlling the composition and concentration of the lipid conjugate, one can control the lipid particle (e.g., SNALP) size.

VI. Preparation of Lipid Particles

The lipid particles of the present invention, e.g., SNALP, in which an active agent such as a nucleic acid (e.g., an interfering RNA such as an siRNA) is entrapped within the lipid portion of the particle and is protected from degradation, can be formed by any method known in the art including, but not limited to, a continuous mixing method, a direct dilution process, and an in-line dilution process. In certain embodiments, one or more antioxidants such as metal chelators (e.g., EDTA), primary antioxidants, and/or secondary antioxidants may be included at any step or at multiple steps in the process (e.g., prior to, during, and/or after lipid particle formation) as described in PCT Application No. PCT/CA2010/001919, the disclosure of which is herein incorporated by reference in its entirety for all purposes.

In particular embodiments, the cationic lipids may comprise at least one, two, three, four, five, or more cationic lipids such as those set forth in Formulas I-III or salts thereof, alone or in combination with other cationic lipid species. In other embodiments, the non-cationic lipids may comprise one, two, or more lipids including egg sphingomyelin (ESM), distearoylphosphatidylcholine (DSPC), dioleoylphosphatidylcholine (DOPC), 1-palmitoyl-2-oleoyl-phosphatidylcholine (POPC), dipalmitoyl-phosphatidylcholine (DPPC), monomethyl-phosphatidylethanolamine, dimethyl-phosphatidylethanolamine, 14:0 PE (1,2-dimyristoyl-phosphatidylethanolamine (DMPE)), 16:0 PE (1,2-dipalmitoyl-phosphatidylethanolamine (DPPE)), 18:0 PE (1,2-distearoyl-phosphatidylethanolamine (DSPE)), 18:1 PE (1,2-dioleoylphosphatidylethanolamine (DOPE)), 18:1 trans PE (1,2-dielaidoyl-phosphatidylethanolamine (DEPE)), 18:0-18:1 PE (1-stearoyl-2-oleoyl-phosphatidylethanolamine (SOPE)), 16:0-18:1 PE (1-palmitoyl-2-oleoyl-phosphatidylethanolamine (POPE)), polyethylene glycol-based polymers (e.g., PEG 2000, PEG 5000, PEG-modified diacylglycerols, or PEG-modified dialkyloxypropyls), cholesterol, derivatives thereof, or combinations thereof.

In certain embodiments, the present invention provides nucleic acid-lipid particles (e.g., SNALP) produced via a continuous mixing method, e.g., a process that includes providing an aqueous solution comprising a nucleic acid (e.g., interfering RNA) in a first reservoir, providing an organic lipid solution in a second reservoir (wherein the lipids present in the organic lipid solution are solubilized in an organic solvent, e.g., a lower alkanol such as ethanol), and mixing the aqueous solution with the organic lipid solution such that the organic lipid solution mixes with the aqueous solution so as to substantially instantaneously produce a lipid vesicle (e.g., liposome) encapsulating the nucleic acid within the lipid vesicle. This process and the apparatus for carrying out this process are described in detail in U.S. Patent Publication No. 20040142025, the disclosure of which is herein incorporated by reference in its entirety for all purposes.

The action of continuously introducing lipid and buffer solutions into a mixing environment, such as in a mixing chamber, causes a continuous dilution of the lipid solution with the buffer solution, thereby producing a lipid vesicle substantially instantaneously upon mixing. As used herein, the phrase "continuously diluting a lipid solution with a buffer solution" (and variations) generally means that the lipid solution is diluted sufficiently rapidly in a hydration process with sufficient force to effectuate vesicle generation. By mixing the aqueous solution comprising a nucleic acid with the organic lipid solution, the organic lipid solution undergoes a continuous stepwise dilution in the presence of the buffer solution (i.e., aqueous solution) to produce a nucleic acid-lipid particle.

The nucleic acid-lipid particles formed using the continuous mixing method typically have a size of from about 30 nm to about 150 nm, from about 40 nm to about 150 nm, from about 50 nm to about 150 nm, from about 60 nm to about 130 nm, from about 70 nm to about 110 nm, from about 70 nm to about 100 nm, from about 80 nm to about 100 nm, from about 90 nm to about 100 nm, from about 70 to about 90 nm, from about 80 nm to about 90 nm, from about 70 nm to about 80 nm, less than about 120 nm, 110 nm, 100 nm, 90 nm, or 80 nm, or about 30 nm, 35 nm, 40 nm, 45 nm, 50 nm, 55 nm, 60 nm, 65 nm, 70 nm, 75 nm, 80 nm, 85 nm, 90 nm, 95 nm, 100 nm, 105 nm, 110 nm, 115 nm, 120 nm, 125 nm, 130 nm, 135 nm, 140 nm, 145 nm, or 150 nm (or any fraction thereof or range therein). The particles thus formed do not aggregate and are optionally sized to achieve a uniform particle size.

In another embodiment, the present invention provides nucleic acid-lipid particles (e.g., SNALP) produced via a direct dilution process that includes forming a lipid vesicle (e.g., liposome) solution and immediately and directly introducing the lipid vesicle solution into a collection vessel containing a controlled amount of dilution buffer. In preferred aspects, the collection vessel includes one or more elements configured to stir the contents of the collection vessel to facilitate dilution. In one aspect, the amount of dilution buffer present in the collection vessel is substantially equal to the volume of lipid vesicle solution introduced thereto. As a non-limiting example, a lipid vesicle solution in 45% ethanol when introduced into the collection vessel containing an equal volume of dilution buffer will advantageously yield smaller particles.

In yet another embodiment, the present invention provides nucleic acid-lipid particles (e.g., SNALP) produced via an in-line dilution process in which a third reservoir containing dilution buffer is fluidly coupled to a second mixing region. In this embodiment, the lipid vesicle (e.g., liposome) solution formed in a first mixing region is immediately and directly mixed with dilution buffer in the second mixing region. In preferred aspects, the second mixing region includes a T-connector arranged so that the lipid vesicle solution and the dilution buffer flows meet as opposing 180° flows; however, connectors providing shallower angles can be used, e.g., from about 27° to about 180° (e.g., about 90°). A pump mechanism delivers a controllable flow of buffer to the second mixing region. In one aspect, the flow rate of dilution buffer provided to the second mixing region is controlled to be substantially equal to the flow rate of lipid vesicle solution introduced thereto from the first mixing region. This embodiment advantageously allows for more control of the flow of dilution buffer mixing with the lipid vesicle solution in the second mixing region, and therefore also the concentration of lipid vesicle solution in buffer throughout the second mixing process. Such control of the dilution buffer flow rate advantageously allows for small particle size formation at reduced concentrations.

These processes and the apparatuses for carrying out these direct dilution and in-line dilution processes are described in detail in U.S. Patent Publication No. 20070042031, the disclosure of which is herein incorporated by reference in its entirety for all purposes.

The nucleic acid-lipid particles formed using the direct dilution and in-line dilution processes typically have a size of from about 30 nm to about 150 nm, from about 40 nm to about 150 nm, from about 50 nm to about 150 nm, from about 60 nm to about 130 nm, from about 70 nm to about 110 nm, from about 70 nm to about 100 nm, from about 80 nm to about 100 nm, from about 90 nm to about 100 nm, from about 70 to about 90 nm, from about 80 nm to about 90 nm, from about 70 nm to about 80 nm, less than about 120 nm, 110 nm, 100 nm, 90 nm, or 80 nm, or about 30 nm, 35 nm, 40 nm, 45 nm, 50 nm, 55 nm, 60 nm, 65 nm, 70 nm, 75 nm, 80 nm, 85 nm, 90 nm, 95 nm, 100 nm, 105 nm, 110 nm, 115 nm, 120 nm, 125 nm, 130 nm, 135 nm, 140 nm, 145 nm, or 150 nm (or any fraction thereof or range therein). The particles thus formed do not aggregate and are optionally sized to achieve a uniform particle size.

If needed, the lipid particles of the invention (e.g., SNALP) can be sized by any of the methods available for sizing liposomes. The sizing may be conducted in order to achieve a desired size range and relatively narrow distribution of particle sizes.

Several techniques are available for sizing the particles to a desired size. One sizing method, used for liposomes and equally applicable to the present particles, is described in U.S. Pat. No. 4,737,323, the disclosure of which is herein incorporated by reference in its entirety for all purposes. Sonicating a particle suspension either by bath or probe sonication produces a progressive size reduction down to particles of less than about 50 nm in size. Homogenization is another method which relies on shearing energy to fragment larger particles into smaller ones. In a typical homogenization procedure, particles are recirculated through a standard emulsion homogenizer until selected particle sizes, typically between about 60 and about 80 nm, are observed. In both methods, the particle size distribution can be monitored by conventional laser-beam particle size discrimination, or QELS.

Extrusion of the particles through a small-pore polycarbonate membrane or an asymmetric ceramic membrane is also an effective method for reducing particle sizes to a relatively well-defined size distribution. Typically, the suspension is cycled through the membrane one or more times until the desired particle size distribution is achieved. The particles may be extruded through successively smaller-pore membranes, to achieve a gradual reduction in size.

In some embodiments, the nucleic acids present in the particles are precondensed as described in, e.g., U.S. patent application Ser. No. 09/744,103, the disclosure of which is herein incorporated by reference in its entirety for all purposes.

In other embodiments, the methods may further comprise adding non-lipid polycations which are useful to effect the lipofection of cells using the present compositions. Examples of suitable non-lipid polycations include, hexadimethrine bromide (sold under the brand name POLY-BRENE®, from Aldrich Chemical Co., Milwaukee, Wis., USA) or other salts of hexadimethrine. Other suitable polycations include, for example, salts of poly-L-ornithine, poly-L-arginine, poly-L-lysine, poly-D-lysine, polyallylamine, and polyethyleneimine. Addition of these salts is preferably after the particles have been formed.

In some embodiments, the nucleic acid to lipid ratios (mass/mass ratios) in a formed nucleic acid-lipid particle (e.g., SNALP) will range from about 0.01 to about 0.2, from about 0.05 to about 0.2, from about 0.02 to about 0.1, from about 0.03 to about 0.1, or from about 0.01 to about 0.08. The ratio of the starting materials (input) also falls within this range. In other embodiments, the particle preparation uses about 400 μg nucleic acid per 10 mg total lipid or a nucleic acid to lipid mass ratio of about 0.01 to about 0.08 and, more preferably, about 0.04, which corresponds to 1.25 mg of total lipid per 50 μg of nucleic acid. In other preferred embodiments, the particle has a nucleic acid:lipid mass ratio of about 0.08.

In other embodiments, the lipid to nucleic acid ratios (mass/mass ratios) in a formed nucleic acid-lipid particle (e.g., SNALP) will range from about 1 (1:1) to about 100 (100:1), from about 5 (5:1) to about 100 (100:1), from about 1 (1:1) to about 50 (50:1), from about 2 (2:1) to about 50 (50:1), from about 3 (3:1) to about 50 (50:1), from about 4 (4:1) to about 50 (50:1), from about 5 (5:1) to about 50 (50:1), from about 1 (1:1) to about 25 (25:1), from about 2 (2:1) to about 25 (25:1), from about 3 (3:1) to about 25 (25:1), from about 4 (4:1) to about 25 (25:1), from about 5 (5:1) to about 25 (25:1), from about 5 (5:1) to about 20 (20:1), from about 5 (5:1) to about 15 (15:1), from about 5 (5:1) to about 10 (10:1), or about 5 (5:1), 6 (6:1), 7 (7:1), 8 (8:1), 9 (9:1), 10 (10:1), 11 (11:1), 12 (12:1), 13 (13:1), 14 (14:1), 15 (15:1), 16 (16:1), 17 (17:1), 18 (18:1), 19 (19:1), 20 (20:1), 21 (21:1), 22 (22:1), 23 (23:1), 24 (24:1), or 25 (25:1), or any fraction thereof or range therein. The ratio of the starting materials (input) also falls within this range.

As previously discussed, the conjugated lipid may further include a CPL. A variety of general methods for making SNALP-CPLs (CPL-containing SNALP) are discussed herein. Two general techniques include the "post-insertion" technique, that is, insertion of a CPL into, for example, a pre-formed SNALP, and the "standard" technique, wherein the CPL is included in the lipid mixture during, for example, the SNALP formation steps. The post-insertion technique results in SNALP having CPLs mainly in the external face of the SNALP bilayer membrane, whereas standard techniques provide SNALP having CPLs on both internal and external faces. The method is especially useful for vesicles made from phospholipids (which can contain cholesterol) and also for vesicles containing PEG-lipids (such as PEG-DAAs and PEG-DAGs). Methods of making SNALP-CPLs are taught, for example, in U.S. Pat. Nos. 5,705,385; 6,586,410; 5,981,501; 6,534,484; and 6,852,334; U.S. Patent Publication No. 20020072121; and PCT Publication No. WO 00/62813, the disclosures of which are herein incorporated by reference in their entirety for all purposes.

VII. Kits

The present invention also provides lipid particles (e.g., SNALP) in kit form. In some embodiments, the kit comprises a container which is compartmentalized for holding the various elements of the lipid particles (e.g., the active agents or therapeutic agents such as nucleic acids and the individual lipid components of the particles). Preferably, the kit comprises a container (e.g., a vial or ampoule) which holds the lipid particles of the invention (e.g., SNALP), wherein the particles are produced by one of the processes set forth herein. In some embodiments, the kit may further comprise one or more antioxidants such as metal chelators (e.g., EDTA), primary antioxidants, and/or secondary antioxidants. In other embodiments, the kit may further comprise an endosomal membrane destabilizer (e.g., calcium ions). The kit typically contains the particle compositions of the present invention, either as a suspension in a pharmaceutically acceptable carrier or in dehydrated form, with instructions for their rehydration (if lyophilized) and administration.

The lipid particles of the present invention can be tailored to preferentially target particular tissues, organs, or tumors of interest. In certain instances, preferential targeting of lipid particles such as SNALP may be carried out by controlling the composition of the particle itself. In some instances, the 1:57 lipid particle (e.g., SNALP) formulation can be used to preferentially target the liver (e.g., normal liver tissue). In other instances, the 7:54 lipid particle (e.g., SNALP) formulation can be used to preferentially target solid tumors such as liver tumors and tumors outside of the liver. In preferred embodiments, the kits of the invention comprise these liver-directed and/or tumor-directed lipid particles, wherein the particles are present in a container as a suspension or in dehydrated form.

In certain instances, it may be desirable to have a targeting moiety attached to the surface of the lipid particle to further enhance the targeting of the particle. Methods of attaching targeting moieties (e.g., antibodies, proteins, etc.) to lipids (such as those used in the present particles) are known to those of skill in the art.

VIII. Administration of Lipid Particles

Once formed, the lipid particles of the invention (e.g., SNALP) are useful for the introduction of active agents or therapeutic agents (e.g., nucleic acids such as interfering RNA) into cells. Accordingly, the present invention also provides methods for introducing an active agent or therapeutic agent such as a nucleic acid (e.g., interfering RNA) into a cell. In some instances, the cell is a liver cell such as, e.g., a hepatocyte present in liver tissue. In other instances, the cell is a tumor cell such as, e.g., a tumor cell present in a solid tumor. The methods are carried out in vitro or in vivo by first forming the particles as described above and then contacting the particles with the cells for a period of time sufficient for delivery of the active agent or therapeutic agent to the cells to occur.

The lipid particles of the invention (e.g., SNALP) can be adsorbed to almost any cell type with which they are mixed or contacted. Once adsorbed, the particles can either be endocytosed by a portion of the cells, exchange lipids with cell membranes, or fuse with the cells. Transfer or incorporation of the active agent or therapeutic agent (e.g., nucleic acid) portion of the particle can take place via any one of these pathways. In particular, when fusion takes place, the particle membrane is integrated into the cell membrane and the contents of the particle combine with the intracellular fluid.

The lipid particles of the invention (e.g., SNALP) can be administered either alone or in a mixture with a pharmaceutically acceptable carrier (e.g., physiological saline or phosphate buffer) selected in accordance with the route of administration and standard pharmaceutical practice. Generally, normal buffered saline (e.g., 135-150 mM NaCl) will be employed as the pharmaceutically acceptable carrier. Other suitable carriers include, e.g., water, buffered water, 0.4% saline, 0.3% glycine, and the like, including glycoproteins for enhanced stability, such as albumin, lipoprotein, globulin, etc. Additional suitable carriers are described in, e.g., REMINGTON'S PHARMACEUTICAL SCIENCES, Mack Publishing Company, Philadelphia, Pa., 17th ed. (1985). As used herein, "carrier" includes any and all solvents, dispersion media, vehicles, coatings, diluents, antibacterial and antifungal agents, isotonic and absorption delaying agents, buffers, carrier solutions, suspensions, colloids, and the like. The phrase "pharmaceutically acceptable" refers to molecular entities and compositions that do not produce an allergic or similar untoward reaction when administered to a human.

The pharmaceutically acceptable carrier is generally added following lipid particle formation. Thus, after the lipid particle (e.g., SNALP) is formed, the particle can be diluted into pharmaceutically acceptable carriers such as normal buffered saline.

The concentration of particles in the pharmaceutical formulations can vary widely, i.e., from less than about 0.05%, usually at or at least about 2 to 5%, to as much as about 10 to 90% by weight, and will be selected primarily by fluid volumes, viscosities, etc., in accordance with the particular mode of administration selected. For example, the concentration may be increased to lower the fluid load associated with treatment. This may be particularly desirable in patients having atherosclerosis-associated congestive heart failure or severe hypertension. Alternatively, particles composed of irritating lipids may be diluted to low concentrations to lessen inflammation at the site of administration.

The pharmaceutical compositions of the present invention may be sterilized by conventional, well-known sterilization techniques. Aqueous solutions can be packaged for use or filtered under aseptic conditions and lyophilized, the lyophilized preparation being combined with a sterile aqueous solution prior to administration. The compositions can contain pharmaceutically acceptable auxiliary substances as required to approximate physiological conditions, such as pH adjusting and buffering agents, tonicity adjusting agents and the like, for example, sodium acetate, sodium lactate, sodium chloride, potassium chloride, and calcium chloride. Additionally, the particle suspension may include lipid-protective agents which protect lipids against free-radical and lipid-peroxidative damages on storage. Lipophilic free-radical quenchers, such as alphatocopherol, and water-soluble iron-specific chelators, such as ferrioxamine, are suitable.

In some embodiments, the lipid particles of the invention (e.g., SNALP) are particularly useful in methods for the therapeutic delivery of one or more nucleic acids comprising an interfering RNA sequence (e.g., siRNA). In particular, it is an object of this invention to provide in vitro and in vivo methods for treatment of a disease or disorder in a mammal (e.g., a rodent such as a mouse or a primate such as a human, chimpanzee, or monkey) by downregulating or silencing the transcription and/or translation of one or more target nucleic acid sequences or genes of interest. As a non-limiting example, the methods of the invention are useful for in vivo delivery of interfering RNA (e.g., siRNA) to the liver and/or tumor of a mammalian subject. In certain embodiments, the disease or disorder is associated with expression and/or overexpression of a gene and expression or overexpression of the gene is reduced by the interfering RNA (e.g., siRNA). In certain other embodiments, a therapeutically effective amount of the lipid particle may be administered to the mammal. In some instances, an interfering RNA (e.g., siRNA) is formulated into a SNALP, and the particles are administered to patients requiring such treatment. In other instances, cells are removed from a patient, the interfering RNA is delivered in vitro (e.g., using a SNALP described herein), and the cells are reinjected into the patient.

A. In Vivo Administration

Systemic delivery for in vivo therapy, e.g., delivery of a therapeutic nucleic acid to a distal target cell via body systems such as the circulation, has been achieved using nucleic acid-lipid particles such as those described in PCT Publication Nos. WO 05/007196, WO 05/121348, WO 05/120152, and WO 04/002453, the disclosures of which are herein incorporated by reference in their entirety for all purposes. The present invention also provides fully encapsulated lipid particles that protect the nucleic acid from nuclease degradation in serum, are non-immunogenic, are small in size, and are suitable for repeat dosing.

For in vivo administration, administration can be in any manner known in the art, e.g., by injection, oral administration, inhalation (e.g., intranasal or intratracheal), transdermal application, or rectal administration. Administration can be accomplished via single or divided doses. The pharmaceutical compositions can be administered parenterally, i.e., intraarticularly, intravenously, intraperitoneally, subcutaneously, or intramuscularly. In some embodiments, the pharmaceutical compositions are administered intravenously or intraperitoneally by a bolus injection (see, e.g., U.S. Pat. No. 5,286,634). Intracellular nucleic acid delivery has also been discussed in Straubringer et al., *Methods Enzymol.*, 101:512 (1983); Mannino et al., *Biotechniques*, 6:682 (1988); Nicolau et al., *Crit. Rev. Ther. Drug Carrier Syst.*, 6:239 (1989); and Behr, *Acc. Chem. Res.*, 26:274 (1993). Still other methods of administering lipid-based therapeutics are described in, for example, U.S. Pat. Nos. 3,993,754; 4,145,410; 4,235,871; 4,224,179; 4,522,803; and 4,588,578. The lipid particles can be administered by direct injection at the site of disease or by injection at a site distal from the site of disease (see, e.g., Culver, HUMAN GENE THERAPY, MaryAnn Liebert, Inc., Publishers, New York. pp. 70-71 (1994)). The disclosures of the above-described references are herein incorporated by reference in their entirety for all purposes.

In embodiments where the lipid particles of the present invention (e.g., SNALP) are administered intravenously, at least about 5%, 10%, 15%, 20%, or 25% of the total injected dose of the particles is present in plasma about 8, 12, 24, 36, or 48 hours after injection. In other embodiments, more than about 20%, 30%, 40% and as much as about 60%, 70% or 80% of the total injected dose of the lipid particles is present in plasma about 8, 12, 24, 36, or 48 hours after injection. In certain instances, more than about 10% of a plurality of the particles is present in the plasma of a mammal about 1 hour after administration. In certain other instances, the presence of the lipid particles is detectable at least about 1 hour after administration of the particle. In certain embodiments, the presence of a therapeutic agent such as a nucleic acid is detectable in cells of the lung, liver, tumor, or at a site of inflammation at about 8, 12, 24, 36, 48, 60, 72 or 96 hours after administration. In other embodiments, downregulation of expression of a target sequence by an interfering RNA (e.g., siRNA) is detectable at about 8, 12, 24, 36, 48, 60, 72 or 96 hours after administration. In yet other embodiments, downregulation of expression of a target sequence by an interfering RNA (e.g., siRNA) occurs preferentially in liver cells (e.g., hepatocytes), tumor cells, or in cells at a site of inflammation. In further embodiments, the presence or effect of an interfering RNA (e.g., siRNA) in cells at a site proximal or distal to the site of administration or in cells of the lung, liver, or a tumor is detectable at about 12, 24, 48, 72, or 96 hours, or at about 6, 8, 10, 12, 14, 16, 18, 19, 20, 22, 24, 26, or 28 days after administration. In additional embodiments, the lipid particles (e.g., SNALP) of the invention are administered parenterally or intraperitoneally.

The compositions of the present invention, either alone or in combination with other suitable components, can be made into aerosol formulations (i.e., they can be "nebulized") to be administered via inhalation (e.g., intranasally or intratracheally) (see, Brigham et al., *Am. J. Sci.*, 298:278 (1989)). Aerosol formulations can be placed into pressurized acceptable propellants, such as dichlorodifluoromethane, propane, nitrogen, and the like.

In certain embodiments, the pharmaceutical compositions may be delivered by intranasal sprays, inhalation, and/or other aerosol delivery vehicles. Methods for delivering nucleic acid compositions directly to the lungs via nasal aerosol sprays have been described, e.g., in U.S. Pat. Nos. 5,756,353 and 5,804,212. Likewise, the delivery of drugs using intranasal microparticle resins and lysophosphatidyl-glycerol compounds (U.S. Pat. No. 5,725,871) are also well-known in the pharmaceutical arts. Similarly, transmucosal drug delivery in the form of a polytetrafluoroetheylene support matrix is described in U.S. Pat. No. 5,780,045. The disclosures of the above-described patents are herein incorporated by reference in their entirety for all purposes.

Formulations suitable for parenteral administration, such as, for example, by intraarticular (in the joints), intravenous, intramuscular, intradermal, intraperitoneal, and subcutaneous routes, include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. In the practice of this invention, compositions are preferably administered, for example, by intravenous infusion, orally, topically, intraperitoneally, intravesically, or intrathecally.

Generally, when administered intravenously, the lipid particle formulations are formulated with a suitable pharmaceutical carrier. Many pharmaceutically acceptable carriers may be employed in the compositions and methods of the present invention. Suitable formulations for use in the present invention are found, for example, in REMINGTON'S PHARMACEUTICAL SCIENCES, Mack Publishing Company, Philadelphia, Pa., 17th ed. (1985). A variety of aqueous carriers may be used, for example, water, buffered water, 0.4% saline, 0.3% glycine, and the like, and may include glycoproteins for enhanced stability, such as albumin, lipoprotein, globulin, etc. Generally, normal buffered saline (135-150 mM NaCl) will be employed as the pharmaceutically acceptable carrier, but other suitable carriers will suffice. These compositions can be sterilized by conventional liposomal sterilization techniques, such as filtration. The compositions may contain pharmaceutically acceptable auxiliary substances as required to approximate physiological conditions, such as pH adjusting and buffering agents, tonicity adjusting agents, wetting agents and the like, for example, sodium acetate, sodium lactate, sodium chloride, potassium chloride, calcium chloride, sorbitan monolaurate, triethanolamine oleate, etc. These compositions can be sterilized using the techniques referred to above or, alternatively, they can be produced under sterile conditions. The resulting aqueous solutions may be packaged for use or filtered under aseptic conditions and lyophilized, the lyophilized preparation being combined with a sterile aqueous solution prior to administration.

In certain applications, the lipid particles disclosed herein may be delivered via oral administration to the individual. The particles may be incorporated with excipients and used in the form of ingestible tablets, buccal tablets, troches, capsules, pills, lozenges, elixirs, mouthwash, suspensions, oral sprays, syrups, wafers, and the like (see, e.g., U.S. Pat. Nos. 5,641,515, 5,580,579, and 5,792,451, the disclosures of which are herein incorporated by reference in their entirety for all purposes). These oral dosage forms may also contain the following: binders, gelatin; excipients, lubricants, and/or flavoring agents. When the unit dosage form is a capsule, it may contain, in addition to the materials described above, a liquid carrier. Various other materials may be present as coatings or to otherwise modify the physical form of the dosage unit. Of course, any material used in preparing any unit dosage form should be pharmaceutically pure and substantially non-toxic in the amounts employed.

Typically, these oral formulations may contain at least about 0.1% of the lipid particles or more, although the percentage of the particles may, of course, be varied and may conveniently be between about 1% or 2% and about 60% or 70% or more of the weight or volume of the total formulation. Naturally, the amount of particles in each therapeutically useful composition may be prepared is such a way that a suitable dosage will be obtained in any given unit dose of the compound. Factors such as solubility, bioavailability, biological half-life, route of administration, product shelf life, as well as other pharmacological considerations will be contemplated by one skilled in the art of preparing such pharmaceutical formulations, and as such, a variety of dosages and treatment regimens may be desirable.

Formulations suitable for oral administration can consist of: (a) liquid solutions, such as an effective amount of a packaged therapeutic agent such as nucleic acid (e.g., interfering RNA) suspended in diluents such as water, saline, or PEG 400; (b) capsules, sachets, or tablets, each containing a predetermined amount of a therapeutic agent such as nucleic acid (e.g., interfering RNA), as liquids, solids, granules, or gelatin; (c) suspensions in an appropriate liquid; and (d) suitable emulsions. Tablet forms can include one or more of lactose, sucrose, mannitol, sorbitol, calcium phosphates, corn starch, potato starch, microcrystalline cellulose, gelatin, colloidal silicon dioxide, talc, magnesium stearate, stearic acid, and other excipients, colorants, fillers, binders, diluents, buffering agents, moistening agents, preservatives, flavoring agents, dyes, disintegrating agents, and pharmaceutically compatible carriers. Lozenge forms can comprise a therapeutic agent such as nucleic acid (e.g., interfering RNA) in a flavor, e.g., sucrose, as well as pastilles comprising the therapeutic agent in an inert base, such as gelatin and glycerin or sucrose and acacia emulsions, gels, and the like containing, in addition to the therapeutic agent, carriers known in the art.

In another example of their use, lipid particles can be incorporated into a broad range of topical dosage forms. For instance, a suspension containing nucleic acid-lipid particles such as SNALP can be formulated and administered as gels, oils, emulsions, topical creams, pastes, ointments, lotions, foams, mousses, and the like.

When preparing pharmaceutical preparations of the lipid particles of the invention, it is preferable to use quantities of the particles which have been purified to reduce or eliminate empty particles or particles with therapeutic agents such as nucleic acid associated with the external surface.

The methods of the present invention may be practiced in a variety of hosts. Preferred hosts include mammalian species, such as primates (e.g., humans and chimpanzees as well as other nonhuman primates), canines, felines, equines, bovines, ovines, caprines, rodents (e.g., rats and mice), lagomorphs, and swine.

The amount of particles administered will depend upon the ratio of therapeutic agent (e.g., nucleic acid) to lipid, the particular therapeutic agent (e.g., nucleic acid) used, the disease or disorder being treated, the age, weight, and condition of the patient, and the judgment of the clinician, but will generally be between about 0.01 and about 50 mg per kilogram of body weight, preferably between about 0.1 and about 5 mg/kg of body weight, or about $10^8$-$10^{10}$ particles per administration (e.g., injection).

B. In Vitro Administration

For in vitro applications, the delivery of therapeutic agents such as nucleic acids (e.g., interfering RNA) can be to any cell grown in culture, whether of plant or animal origin, vertebrate or invertebrate, and of any tissue or type. In preferred embodiments, the cells are animal cells, more preferably mammalian cells, and most preferably human cells (e.g., tumor cells or hepatocytes).

Contact between the cells and the lipid particles, when carried out in vitro, takes place in a biologically compatible medium. The concentration of particles varies widely depending on the particular application, but is generally between about 1 µmol and about 10 mmol. Treatment of the cells with the lipid particles is generally carried out at physiological temperatures (about 37° C.) for periods of time of from about 1 to 48 hours, preferably of from about 2 to 4 hours.

In one group of preferred embodiments, a lipid particle suspension is added to 60-80% confluent plated cells having a cell density of from about $10^3$ to about $10^5$ cells/ml, more preferably about $2 \times 10^4$ cells/ml. The concentration of the suspension added to the cells is preferably of from about 0.01 to 0.2 µg/ml, more preferably about 0.1 µg/ml.

To the extent that tissue culture of cells may be required, it is well-known in the art. For example, Freshney, Culture of Animal Cells, a Manual of Basic Technique, 3rd Ed., Wiley-Liss, New York (1994), Kuchler et al., Biochemical Methods in Cell Culture and Virology, Dowden, Hutchinson and Ross, Inc. (1977), and the references cited therein provide a general guide to the culture of cells. Cultured cell systems often will be in the form of monolayers of cells, although cell suspensions are also used.

Using an Endosomal Release Parameter (ERP) assay, the delivery efficiency of the SNALP or other lipid particle of the invention can be optimized. An ERP assay is described in detail in U.S. Patent Publication No. 20030077829, the disclosure of which is herein incorporated by reference in its entirety for all purposes. More particularly, the purpose of an ERP assay is to distinguish the effect of various cationic lipids and helper lipid components of SNALP or other lipid particle based on their relative effect on binding/uptake or fusion with/destabilization of the endosomal membrane. This assay allows one to determine quantitatively how each component of the SNALP or other lipid particle affects delivery efficiency, thereby optimizing the SNALP or other lipid particle. Usually, an ERP assay measures expression of a reporter protein (e.g., luciferase, β-galactosidase, green fluorescent protein (GFP), etc.), and in some instances, a SNALP formulation optimized for an expression plasmid will also be appropriate for encapsulating an interfering RNA. In other instances, an ERP assay can be adapted to measure downregulation of transcription or translation of a target sequence in the presence or absence of an interfering RNA (e.g., siRNA). By comparing the ERPs for each of the various SNALP or other lipid particles, one can readily determine the optimized system, e.g., the SNALP or other lipid particle that has the greatest uptake in the cell.

C. Cells for Delivery of Lipid Particles

The compositions and methods of the present invention are used to treat a wide variety of cell types, in vivo and in vitro. Suitable cells include, but are not limited to, hepatocytes, reticuloendothelial cells (e.g., monocytes, macrophages, etc.), fibroblast cells, endothelial cells, platelet cells, other cell types infected and/or susceptible of being infected with viruses, hematopoietic precursor (stem) cells, keratinocytes, skeletal and smooth muscle cells, osteoblasts, neurons, quiescent lymphocytes, terminally differentiated cells, slow or noncycling primary cells, parenchymal cells, lymphoid cells, epithelial cells, bone cells, and the like.

In particular embodiments, an active agent or therapeutic agent such as a nucleic acid (e.g., an interfering RNA) is delivered to cancer cells (e.g., cells of a solid tumor) including, but not limited to, liver cancer cells, lung cancer cells, colon cancer cells, rectal cancer cells, anal cancer cells, bile duct cancer cells, small intestine cancer cells, stomach (gastric) cancer cells, esophageal cancer cells, gallbladder cancer cells, pancreatic cancer cells, appendix cancer cells, breast cancer cells, ovarian cancer cells, cervical cancer cells, prostate cancer cells, renal cancer cells, cancer cells of the central nervous system, glioblastoma tumor cells, skin cancer cells, lymphoma cells, choriocarcinoma tumor cells, head and neck cancer cells, osteogenic sarcoma tumor cells, and blood cancer cells.

In vivo delivery of lipid particles such as SNALP encapsulating a nucleic acid (e.g., an interfering RNA) is suited for targeting cells of any cell type. The methods and compositions can be employed with cells of a wide variety of vertebrates, including mammals, such as, e.g, canines, felines, equines, bovines, ovines, caprines, rodents (e.g., mice, rats, and guinea pigs), lagomorphs, swine, and primates (e.g. monkeys, chimpanzees, and humans).

D. Detection of Lipid Particles

In some embodiments, the lipid particles of the present invention (e.g., SNALP) are detectable in the subject at about 1, 2, 3, 4, 5, 6, 7, 8 or more hours. In other embodiments, the lipid particles of the present invention (e.g., SNALP) are detectable in the subject at about 8, 12, 24, 48, 60, 72, or 96 hours, or about 6, 8, 10, 12, 14, 16, 18, 19, 22, 24, 25, or 28 days after administration of the particles. The presence of the particles can be detected in the cells, tissues, or other biological samples from the subject. The particles may be detected, e.g., by direct detection of the particles, detection of a therapeutic nucleic acid such as an interfering RNA (e.g., siRNA) sequence, detection of the target sequence of interest (i.e., by detecting expression or reduced expression of the sequence of interest), or a combination thereof.

1. Detection of Particles

Lipid particles of the invention such as SNALP can be detected using any method known in the art. For example, a label can be coupled directly or indirectly to a component of the lipid particle using methods well-known in the art. A wide variety of labels can be used, with the choice of label depending on sensitivity required, ease of conjugation with the lipid particle component, stability requirements, and available instrumentation and disposal provisions. Suitable labels include, but are not limited to, spectral labels such as fluorescent dyes (e.g., fluorescein and derivatives, such as fluorescein isothiocyanate (FITC) and Oregon Green™; rhodamine and derivatives such Texas red, tetrarhodimine isothiocynate (TRITC), etc., digoxigenin, biotin, phycoerythrin, AMCA, CyDyes™, and the like; radiolabels such as $^3$H, $^{125}$I, $^{35}$S, $^{14}$C, $^{32}$P, $^{33}$P, etc.; enzymes such as horse radish peroxidase, alkaline phosphatase, etc.; spectral colorimetric labels such as colloidal gold or colored glass or plastic beads such as polystyrene, polypropylene, latex, etc. The label can be detected using any means known in the art.

2. Detection of Nucleic Acids

Nucleic acids (e.g., interfering RNA) are detected and quantified herein by any of a number of means well-known to those of skill in the art. The detection of nucleic acids may proceed by well-known methods such as Southern analysis, Northern analysis, gel electrophoresis, PCR, radiolabeling, scintillation counting, and affinity chromatography. Additional analytic biochemical methods such as spectrophotometry, radiography, electrophoresis, capillary electrophoresis, high performance liquid chromatography (HPLC), thin layer chromatography (TLC), and hyperdiffusion chromatography may also be employed.

The selection of a nucleic acid hybridization format is not critical. A variety of nucleic acid hybridization formats are known to those skilled in the art. For example, common formats include sandwich assays and competition or displacement assays. Hybridization techniques are generally described in, e.g., "Nucleic Acid Hybridization, A Practical Approach," Eds. Hames and Higgins, IRL Press (1985).

The sensitivity of the hybridization assays may be enhanced through the use of a nucleic acid amplification system which multiplies the target nucleic acid being detected. In vitro amplification techniques suitable for amplifying sequences for use as molecular probes or for generating nucleic acid fragments for subsequent subcloning are known. Examples of techniques sufficient to direct persons of skill through such in vitro amplification methods, including the polymerase chain reaction (PCR), the ligase chain reaction (LCR), Qβ-replicase amplification, and other RNA polymerase mediated techniques (e.g., NASBA™) are found in Sambrook et al., In *Molecular Cloning: A Laboratory Manual*, Cold Spring Harbor Laboratory Press (2000); and Ausubel et al., SHORT PROTOCOLS IN MOLECULAR BIOLOGY, eds., Current Protocols, Greene Publishing Associates, Inc. and John Wiley & Sons, Inc. (2002); as well as U.S. Pat. No. 4,683,202; PCR Protocols, A Guide to Methods and Applications (Innis et al. eds.) Academic Press Inc. San Diego, Calif., (1990); Arnheim & Levinson (Oct. 1, 1990), *C&EN* 36; The *Journal Of NIH Research*, 3:81 (1991); Kwoh et al., *Proc. Natl. Acad. Sci. USA*, 86:1173 (1989); Guatelli et al., *Proc. Natl. Acad. Sci. USA*, 87:1874 (1990); Lomell et al., *J. Clin. Chem.*, 35:1826 (1989); Landegren et al., *Science*, 241:1077 (1988); Van Brunt, *Biotechnology*, 8:291 (1990); Wu and Wallace, *Gene*, 4:560 (1989); Barringer et al., *Gene*, 89:117 (1990); and Sooknanan and Malek, *Biotechnology*, 13:563 (1995). Improved methods of cloning in vitro amplified nucleic acids are described in U.S. Pat. No. 5,426,039. Other methods described in the art are the nucleic acid sequence based amplification (NASBA™, Cangene, Mississauga, Ontario) and Qβ-replicase systems. These systems can be used to directly identify mutants where the PCR or LCR primers are designed to be extended or ligated only when a select sequence is present. Alternatively, the select sequences can be generally amplified using, for example, nonspecific PCR primers and the amplified target region later probed for a specific sequence indicative of a mutation. The disclosures of the above-described references are herein incorporated by reference in their entirety for all purposes.

Nucleic acids for use as probes, e.g., in in vitro amplification methods, for use as gene probes, or as inhibitor components are typically synthesized chemically according to the solid phase phosphoramidite triester method described by Beaucage et al., *Tetrahedron Letts.*, 22:1859 1862 (1981), e.g., using an automated synthesizer, as described in Needham VanDevanter et al., *Nucleic Acids Res.*, 12:6159 (1984). Purification of polynucleotides, where necessary, is typically performed by either native acrylamide gel electrophoresis or by anion exchange HPLC as described in Pearson et al., *J. Chrom.*, 255:137 149 (1983). The sequence of the synthetic polynucleotides can be verified using the chemical degradation method of Maxam and Gilbert (1980) in Grossman and Moldave (eds.) Academic Press, New York, *Methods in Enzymology*, 65:499.

An alternative means for determining the level of transcription is in situ hybridization. In situ hybridization assays are well-known and are generally described in Angerer et al., *Methods Enzymol.*, 152:649 (1987). In an in situ hybridization assay, cells are fixed to a solid support, typically a glass slide. If DNA is to be probed, the cells are denatured with heat or alkali. The cells are then contacted with a hybridization solution at a moderate temperature to permit annealing of specific probes that are labeled. The probes are preferably labeled with radioisotopes or fluorescent reporters.

IX. Examples

The present invention will be described in greater detail by way of specific examples. The following examples are offered for illustrative purposes, and are not intended to limit the invention in any manner. Those of skill in the art will readily recognize a variety of noncritical parameters which can be changed or modified to yield essentially the same results.

Example 1. Synthesis of CP-DODMA

CP-DODMA (Compound 1) having the structure shown below was synthesized as described below.

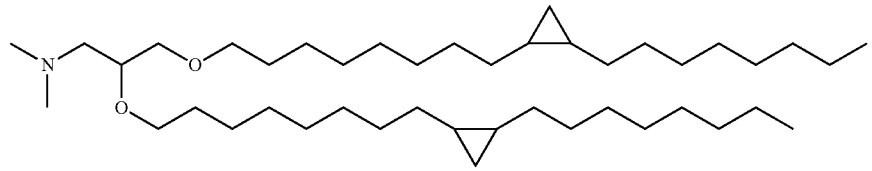

Chemical Formula: $C_{43}H_{85}NO_2$
Exact Mass: 647.66
Molecular Weight: 648.14
Elemental Analysis: C, 79.68; H, 13.22; N, 2.16; O, 4.94

A solution of DODMA (310 mg, 0.5 mmol) in anhydrous dichloromethane (10 mL) under nitrogen was cooled to 0° C. and a 1M solution of diethylzinc in hexanes (5 mL, 5 mmol, 5 eqv) added. The solution was stirred for 1 hour at 0° C. then diiodomethane (1.34 g, 404 µL, 5 mmol) was added and the solution was stirred for 16 hours at room temperature under nitrogen. TLC (8% MeOH in $CHCl_3$) showed that the starting material was consumed and a very slightly more polar product had formed. The reaction mixture was concentrated and purified by column chromatography. A polar (lower running) impurity coeluted with the product. After concentrating appropriate column fractions they were dissolved in EtOAc and washed with 5% HCl (2×10 mL), water (10 mL), sat. $NaHCO_3$ (10 mL), water (10 mL) and brine (10 mL). The solution was dried over $MgSO_4$ and concentrated to afford a clear pale yellow oil (200 mg, 62%). $^1$H NMR analysis showed complete conversion of the cis-alkenes to cyclopropyl groups.

Example 2. Synthesis of CP-DPetroDMA

CP-DPetroDMA (Compound 2) having the structure shown below was synthesized as described below.

Chemical Formula: $C_{43}H_{85}NO_2$
Exact Mass: 647.66
Molecular Weight: 648.14
Elemental Analysis: C, 79.68; H, 13.22; N, 2.16; O, 4.94

A solution of DPetroDMA (300 mg, 0.48 mmol) in anhydrous dichloromethane (10 mL) under nitrogen was cooled to 0° C. and a 1M solution of diethylzinc in hexanes (5 mL, 5 mmol, 5 eqv) added. The solution was stirred for 1 hour at 0° C. then diiodomethane (1.34 g, 404 µl, 5 mmol) was added and the solution was stirred overnight at room temperature under nitrogen. TLC (8% MeOH in CHCl$_3$) showed that the starting material was consumed and a very slightly more polar product had formed. The reaction mixture was concentrated and purified by column chromatography. A polar (lower running) impurity coeluted with the product. After concentrating appropriate column fractions they were dissolved in EtOAc and washed with 5% HCl (2×10 mL), water (10 mL), sat. NaHCO$_3$ (10 mL), water (10 mL) and brine (10 mL). The solution was dried over MgSO$_4$ and concentrated to afford a clear pale yellow oil (250 mg, 0.39 mmol, 80%). $^1$H NMR analysis showed complete conversion of the cis-alkenes to cyclopropyl groups.

Example 3. Synthesis of CP-DLinDMA

CP-DLinDMA (Compound 3) having the structure shown below was synthesized as described in Scheme 1 below.

| Reagent | MW | Amount | mmol | Equivalents |
|---|---|---|---|---|
| 1 DLinDMA | 615.06 | 300 mg | 0.49 | 1 |
| 2 Dichloromethane | — | 20 mL | — | — |
| 3 Diethylzinc 1M in hexanes | — | 4.9 mL | 4.9 | 10 |
| 4 Diiodomethane | 267.84 | 2.62 g (790 µL) | 9.8 | 20 |

To a solution of DLinDMA (300 mg, 0.49 mmol) in anhydrous dichloromethane (20 mL) cooled to 0° C. under nitrogen was added a 1M solution of diethylzinc in hexanes (4.9 mL). The solution was stirred for 1 hour at 0° C. then diiodomethane (2.62 g, 9.8 mmol) was added and the solution was stirred for 16 hours at room temperature under nitrogen. The solution was diluted with dichloromethane (20 mL), filtered and concentrated in vacuo to dryness. The residue was purified by column chromatography (10" L×0.5" D; eluted with 2.5% MeOH in CHCl$_3$) to afford the product as a light yellow oil (288 mg, 87%). See also, Tanaka et al., *Bioorg. Med. Chem. Lett.*, 13:1037-1040 (2003).

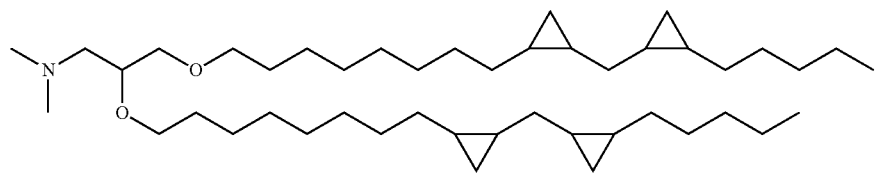

Chemical Formula: C$_{45}$H$_{85}$NO$_2$
Exact Mass: 671.66
Molecular Weight: 672.16
Elemental Analysis: C, 80.41; H, 12.75; N, 2.08 O, 4.76

Scheme 1

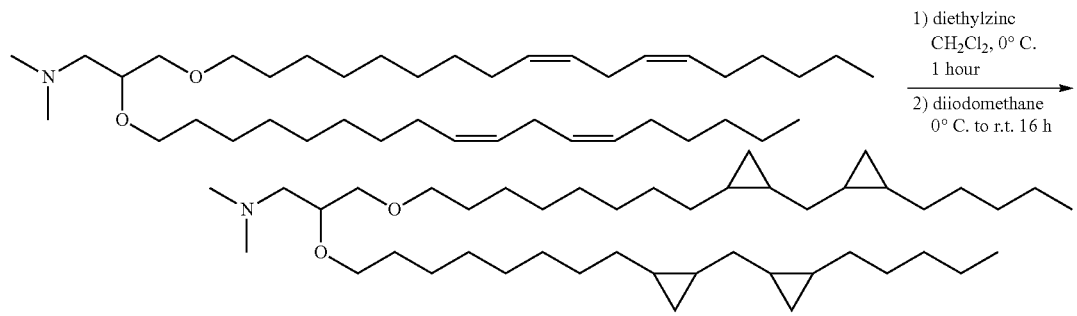

1) diethylzinc
CH$_2$Cl$_2$, 0° C.
1 hour 2) diiodomethane
0° C. to r.t. 16 h

Example 4. Synthesis of CP-DLenDMA

CP-DLenDMA (Compound 4) having the structure shown below was synthesized as described in Scheme 2 below.

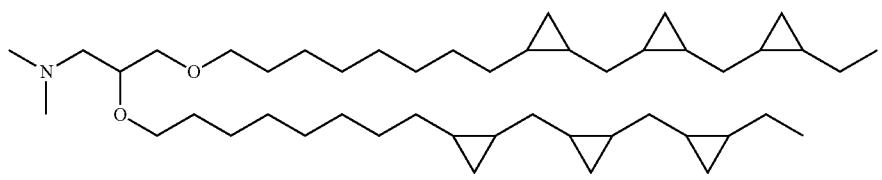

Chemical Formula: C₄₇H₈₅NO₂
Exact Mass: 695.66
Molecular Weight: 696.18
Elemental Analysis: C, 81.09; H, 12.31; N, 2.01; O, 4.60

Scheme 2

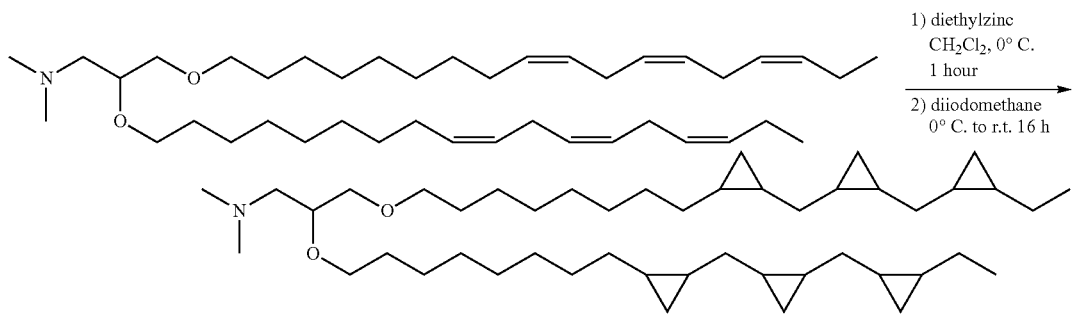

| | Reagent | MW | Amount | mmol | Equivalents |
|---|---|---|---|---|---|
| 1 | DLenDMA | 611.02 | 67 mg | 0.11 | 1 |
| 2 | Dichloromethane | — | 5 mL | — | — |
| 3 | Diethylzinc 1M in hexanes | — | 1.48 mL | 1.48 | 14 |
| 4 | Diiodomethane | 267.84 | 790 mg (237 µL) | 2.95 | 27 |

To a solution of DLenDMA (67 mg, 0.11 mmol) in anhydrous dichloromethane (5 mL) cooled to 0° C. under nitrogen was added a 1M solution of diethylzinc in hexanes (1.48 mL). The solution was stirred for 1 hour at 0° C. then diiodomethane (790 mg, 2.95 mmol) was added and the solution was stirred for 16 hours at room temperature under nitrogen. TLC (8% MeOH in CHCl₃) showed that the starting material was consumed and a very slightly more polar product had formed. The solution was purified by column chromatography without a workup (0.5" D×8" L; eluted with 4% MeOH in CHCl₃) to afford a clear pale yellow oil (73 mg, 96%). ¹H NMR analysis showed complete conversion of the cis-alkenes to cyclopropyl. See also, Tanaka et al., *Bioorg. Med. Chem. Lett.*, 13:1037-1040 (2003).

Example 5. Synthesis of γ-DLenDMA

γ-DLenDMA (Compound 5) having the structure shown below was synthesized as described below.

A 250 mL round bottom flask was charged with 3-(dimethylamino)-1,2-propanediol (0.8 g, 6.7 mmol), tetrabutylammonium hydrogen sulphate (1 g), gamma linolenyl mesylate (cis-6,9,12-octadecatriene sulphonic acid) (5 g, 14.6 mmol), and 30 mL toluene. After stirring for 15 minutes, the reaction was cooled to 0-5° C. A solution of 40% sodium hydroxide (15 mL) was added slowly. The reaction was left to stir for approximately 48 hours. An additional 15 mL of toluene was then added to the reaction vessel, along with 40% sodium hydroxide (15 mL). After the reaction was stirred for an additional 12 hours, water (50 mL) and isopropyl acetate (50 mL) were added and stirred for 15 minutes. The mixture was then transferred to a 500 mL separatory funnel and allowed to separate. The lower aqueous phase was run off and the organic phase was washed with saturated sodium chloride (2×50 mL). Since the aqueous and organic phases resulting from the saturated sodium chloride washes could not be completely separated after 20 minutes, the lower aqueous phase (slightly yellow) was run off and back extracted with chloroform (~45 mL). The organic phase was dried with MgSO₄, filtered, and the solvent evaporated.

The crude product, an orange liquid, was purified on column chromatography using silica gel (60 g) with 0-3% methanol gradient in dichloromethane to yield 3.19 g. The product was further purified via column chromatography on silica gel (50 g) with 10-30% ethyl acetate gradient in hexanes to yield 1.26 g pure product.

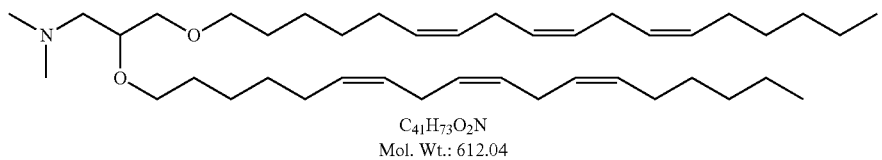 [SMILES: CCCCC/C=C\C/C=C\C/C=C\CCCCCOCC(CN(C)C)OCCCCC/C=C\C/C=C\C/C=C\CCCCC]

C₄₁H₇₃O₂N
Mol. Wt.: 612.04

Example 6. Synthesis of CP-γ-DLenDMA

CP-γ-DLenDMA (Compound 6) having the structure shown below was synthesized as described in Scheme 3 below.

Chemical Formula: $C_{47}H_{85}NO_2$
Exact Mass: 695.66
Molecular Weight: 696.18
Elemental Analysis: C, 81.09; H, 12.31; N, 2.01; O, 4.60

Scheme 3

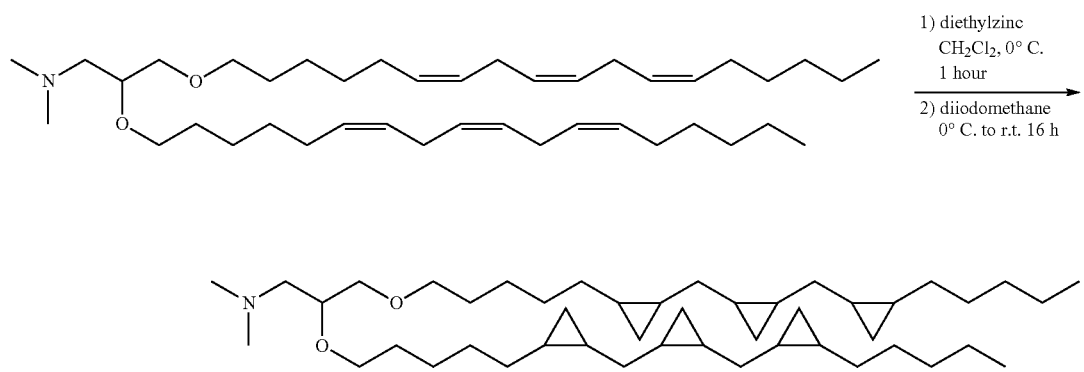

1) diethylzinc
   $CH_2Cl_2$, 0° C.
   1 hour
2) diiodomethane
   0° C. to r.t. 16 h

|   | Reagent | MW | Amount | mmol | Equivalents |
|---|---------|------|-----------|------|-------------|
| 1 | γ-DLenDMA | 612.02 | 100 mg | 0.16 | 1 |
| 2 | Dichloromethane | — | 10 mL | — | — |
| 3 | Diethylzinc 1M in hexanes | — | 2.5 mL | 2.45 | 15 |
| 4 | Diiodomethane | 267.84 | 1.29 g (400 μL) | 4.8 | 30 |

To a solution of γ-DLenDMA (Compound 5) (100 mg, 0.16 mmol) in anhydrous dichloromethane (10 mL) cooled to 0° C. under nitrogen was added a 1M solution of diethylzinc in hexanes (2.5 mL, 2.45 mmol). The solution was stirred for 1 hour at 0° C. then diiodomethane (1.29 g, 4.8 mmol) was added and the solution was stirred for 16 hours at room temperature under nitrogen. Upon completion by TLC (8% MeOH in $CHCl_3$), the solution was concentrated in vacuo to dryness. The residue was purified by column chromatography (10" L×0.5" D; eluted with 100% $CHCl_3$) to afford the product as a yellow oil (111 mg, 98%). See also, Tanaka et al., *Bioorg. Med. Chem. Lett.*, 13:1037-1040 (2003).

Example 7. Synthesis of CP-DLen-C2K-DMA

CP-DLen-C2K-DMA (Compound 11) having the structure shown below was synthesized as described in Scheme 4 below. CP-DLen-C2K-DMA is also known as CP-linolenyl-C2K, CP-Len-C2K, and CP-DLen-C2K.

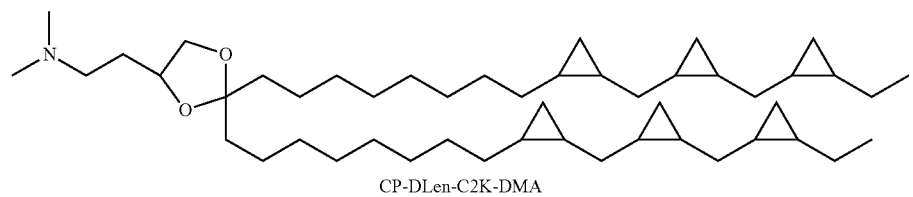 [SMILES: CCC1CC1CC1CC1CC1CC1CCCCCCCCC1(CCCCCCCCC2CC2CC2CC2CC2CC2CC)OCC(CCN(C)C)O1]

CP-DLen-C2K-DMA

Scheme 4

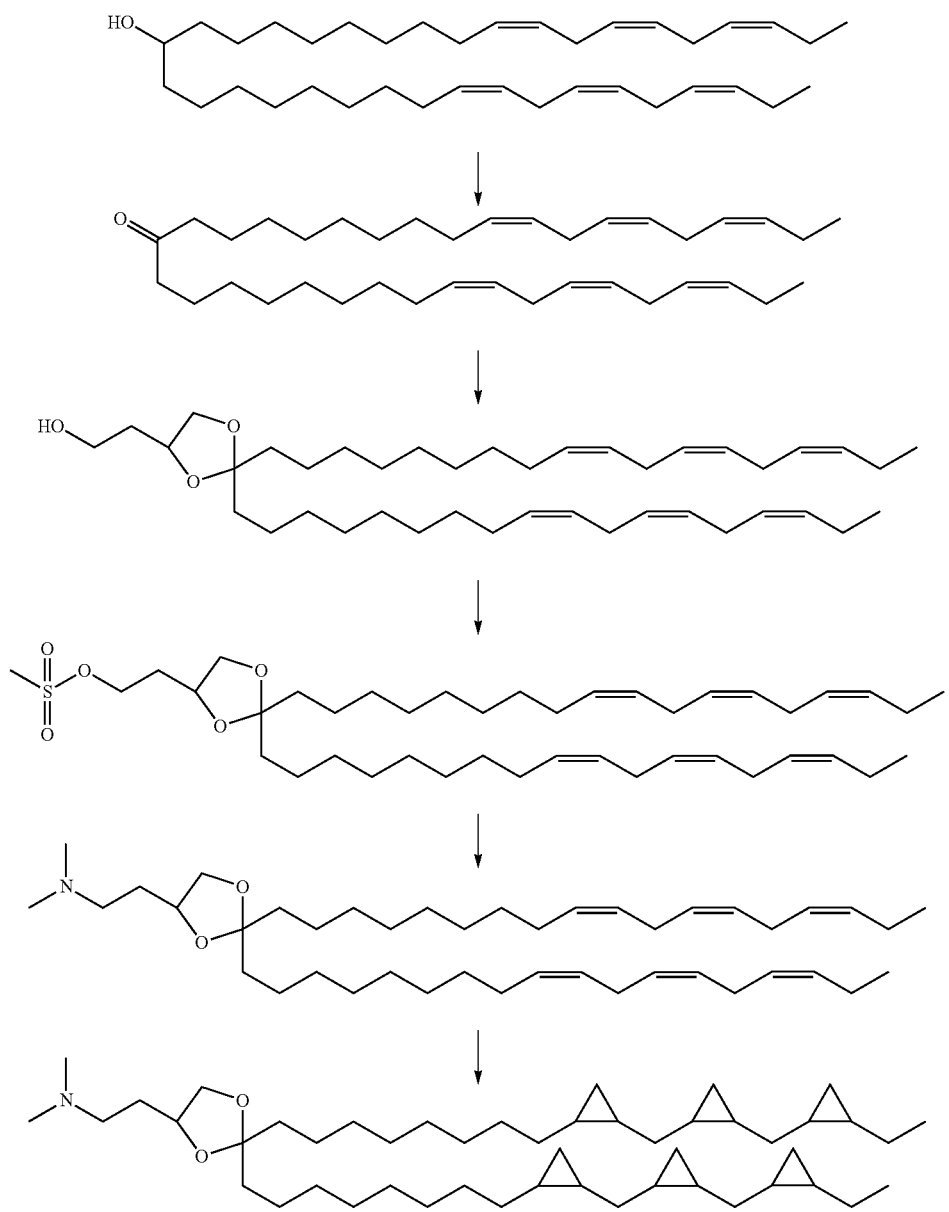

Synthesis of Dilinolenyl Ketone (Compound 7):

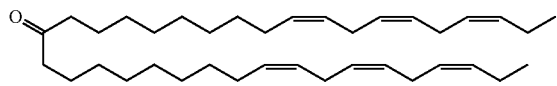 [SMILES: CC/C=C\C/C=C\C/C=C\CCCCCCCCC(=O)CCCCCCCC/C=C\C/C=C\C/C=C\CC]

To a 1000 mL RBF containing a solution of dilinolenyl methanol (6.0 g, 11.4 mmol) in anh. DCM (200 mL) was added pyridinium chlorochromate (7.39 g, 34.2 mmol), anh. sodium carbonate (1.0 g, 5.66 mmol) and a stirbar. The resulting suspension was stirred under nitrogen at RT for 3 h, after which time TLC indicated all SM to have been consumed. Ether (300 mL) was then added to the mixture and the resulting brown suspension filtered through a pad of silica (300 mL), washing the pad with ether (3×100 mL). The ether phases were combined, concentrated and purified to yield 4.2 g (8.0 mmol, 70%) of the ketone.

Synthesis of Linolenyl Ketal (Compound 8):

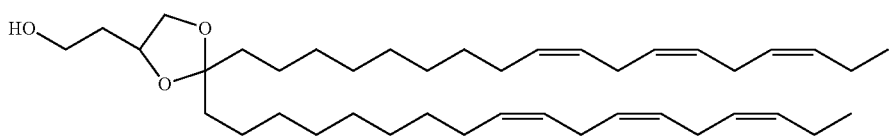 [SMILES: CC/C=C\C/C=C\C/C=C\CCCCCCCCC1(CCCCCCCC/C=C\C/C=C\C/C=C\CC)OCC(CCO)O1]

A 100 mL RBF was charged with dilinolenyl ketone (Compound 7) (4.2 g, 8.2 mmol), 1,2,4-butanetriol (3.4 g, 32 mmol), PPTS (200 mg, 0.8 mmol) and a stir bar. The flask was flushed with nitrogen and anhydrous toluene (60 mL) added. The reaction vessel was fitted with a Dean Stark tube and condenser and brought to reflux and the reaction was left overnight. After cooling to room temperature, the reaction mixture diluted with toluene (50 mL), and washed with 5% aq. Na₂CO₃ (2×50 mL), water (50 mL), dried (MgSO₄) and purified by chromatography to yield 3.0 g (4.9 mmol, 59%) of the ketal.

Mesylate Formation (Compound 9):

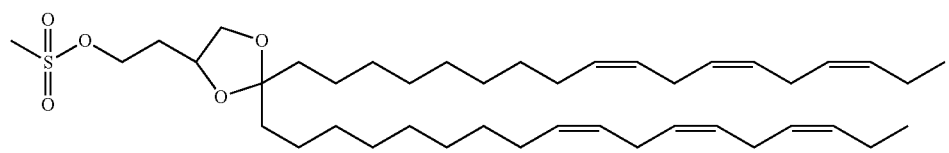 [SMILES: CC/C=C\C/C=C\C/C=C\CCCCCCCCC1(CCCCCCCC/C=C\C/C=C\C/C=C\CC)OCC(CCOS(C)(=O)=O)O1]

A 250 mL RBF was charged with the ketal (Compound 8) (3.0 g, 4.9 mmol), TEA (2.2 mL, 15.6 mmol) and a stir bar. The flask was flushed with nitrogen, anh. DCM (20 mL) added, and the solution cooled to −15° C. In a separate 50 mL flask, a solution of MsCl (9.7 mmol, 2 eqv.) in anhydrous DCM (30 mL) was prepared, then transferred to the reaction vessel by syringe over 20 minutes. The reaction was stirred for 90 minutes at −15° C., at which point starting material had been consumed. The reaction mixture was diluted with a further 50 mL of DCM, washed with NaHCO₃ (2×50 mL), dried (MgSO₄) and purified by chromatography. Final yield 3.1 g, 4.5 mmol, 92%.

Synthesis of D-Len-C2K-DMA (Compound 10):

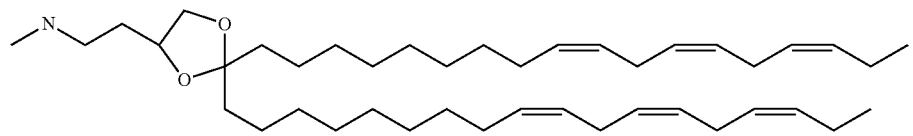 [SMILES: CC/C=C\C/C=C\C/C=C\CCCCCCCCC1(CCCCCCCC/C=C\C/C=C\C/C=C\CC)OCC(CCNC)O1]

A 250 mL RBF was charged with the mesylate (Compound 9) (3.0 g, 4.35 mmol), isopropanol (25 mL) and a stir bar. The flask was flushed with nitrogen, sealed, and a 2.0 M solution of dimethylamine in methanol (120 mL) added via canulla. The reaction was stirred at room temperature for 3 days. The solution was concentrated and purified by chromatography. Final yield 2.49 g, 3.9 mmol, 90%.

Synthesis of CP-DLen-C2K-DMA (Compound 11):

To a 250 mL RBF was added DLen-C2K-DMA (Compound 10) (1.28 g, 2 mmol), a stirbar and anh. DCM (40 mL). The flask was flushed with N₂ and cooled to 0° C., then a 1M solution of diethylzinc in hexanes added (60 mL, 60 mmol, 5 equivalents per olefin). The solution was stirred for 1 hour at 0° C., then diiodomethane (4.84 mL 60 mmol). The reaction mixture was concentrated and then redissolved in EtOAc (50 mL). The EtOAc was washed successively with 5% HCl (2×50 mL), water (50 mL), NaHCO₃ (50 mL), water (50 mL), and brine (50 mL). The aqueous washes were combined and extracted with DCM (2×50 mL). All organics were combined, dried and concentrated to yield crude CP-Len-C2K. ¹H-NMR and HPLC indicated some olefins still to be present, so the compound was treated again, using the same procedures and amounts outlined above. This time ¹H-NMR indicated total conversion of the olefins. Final yield after chromatography was 1.2 g, 1.66 mmol, 83%.

Example 8. Synthesis of CP-γDLen-C2K-DMA

CP-γDLen-C2K-DMA (Compound 16) having the structure shown below was synthesized as described in Scheme 5 below. CP-γDLen-C2K-DMA is also known as CP-γlinolenyl-C2K, CP-γLen-C2K, and CP-D-γ-Len-C2K.

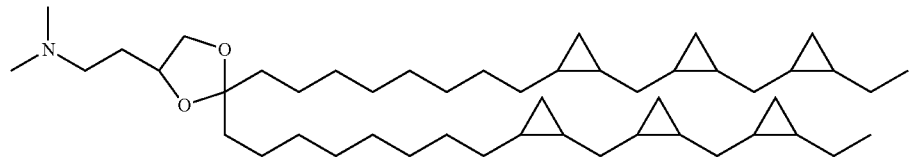 [SMILES: CCC1CC1CC1CC1CC1CC1CCCCCCCCC1(CCCCCCCCC2CC2CC2CC2CC2CC2CC)OCC(CCN(C)C)O1]

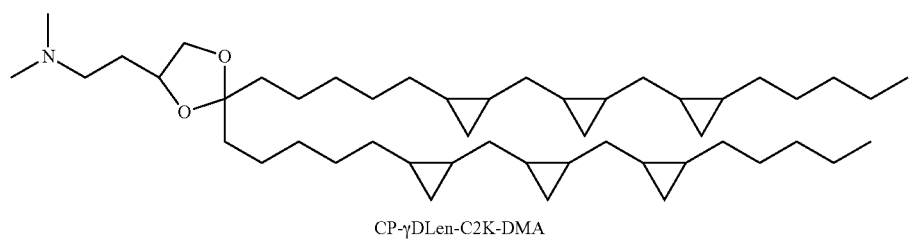 [SMILES: CCCCCC1CC1CC1CC1CC1CC1CCCCCC1(CCCCCC2CC2CC2CC2CC2CC2CCCCC)OCC(CCN(C)C)O1]
CP-γDLen-C2K-DMA
Scheme 5
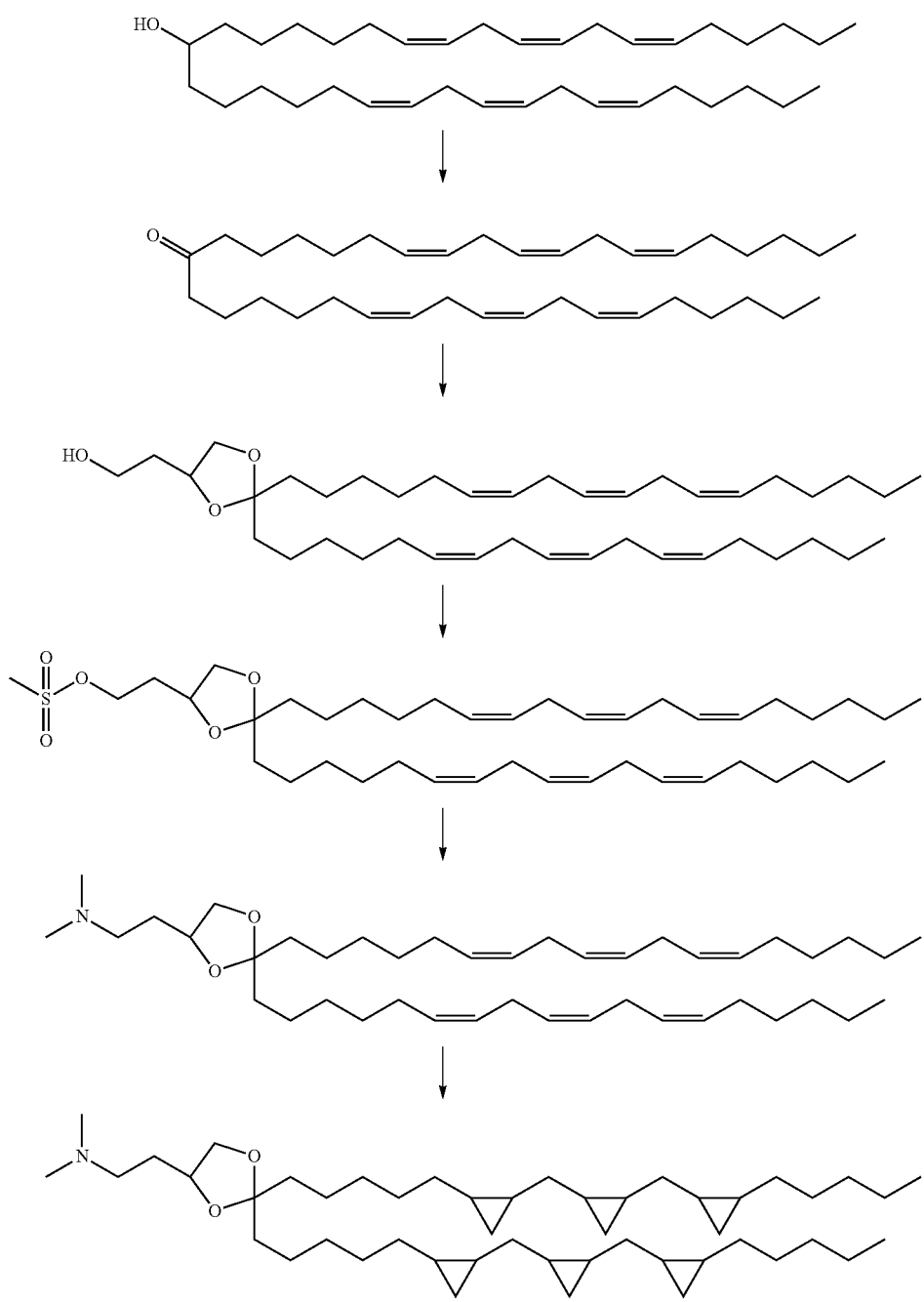

Synthesis of Di-γ-Linolenyl Ketone (Compound 12):

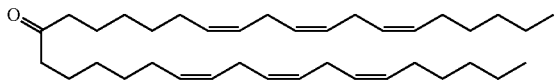 [SMILES: CCCCC/C=C\C/C=C\C/C=C\CCCCCC(=O)CCCCC/C=C\C/C=C\C/C=C\CCCCC]

To a 1000 mL RBF containing a solution of di-γ-linolenyl methanol (6.0 g, 11.4 mmol) in anh. DCM (200 mL) was added pyridinium chlorochromate (7.39 g, 34.2 mmol), anh. sodium carbonate (1.0 g, 5.66 mmol) and a stirbar. The resulting suspension was stirred under nitrogen at RT for 3 h, after which time TLC indicated all SM to have been consumed. Ether (300 mL) was then added to the mixture and the resulting brown suspension filtered through a pad of silica (300 mL), washing the pad with ether (3×100 mL). The ether phases were combined, concentrated and purified to yield 5.5 g (10.5 mmol, 92%) of ketone.

Synthesis of γ-Linolenyl Ketal (Compound 13):

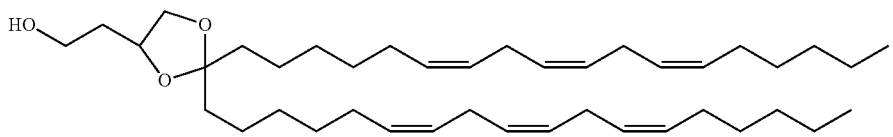 [SMILES: CCCCC/C=C\C/C=C\C/C=C\CCCCCC1(CCCCC/C=C\C/C=C\C/C=C\CCCCC)OCC(CCO)O1]

A 100 mL RBF was charged with di-γ-linolenyl ketone (Compound 12) (2.14 g, 4.1 mmol), 1,2,4-butanetriol (1.7 g, 16.0 mmol), PPTS (100 mg, 0.4 mmol) and a stir bar. The flask was flushed with nitrogen and anhydrous toluene (30 mL) added. The reaction vessel was fitted with a Dean Stark tube and condenser and brought to reflux and the reaction was left overnight. After cooling to room temperature, the reaction mixture was washed with 5% aq. $Na_2CO_3$ (2×50 mL), water (50 mL), dried ($MgSO_4$) and purified by chromatography to yield 1.34 g (2.2 mmol, 53%) of the ketal.

Mesylate Formation (Compound 14):

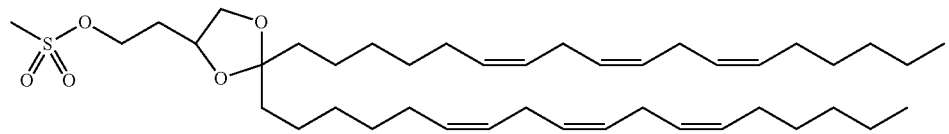 [SMILES: CCCCC/C=C\C/C=C\C/C=C\CCCCCC1(CCCCC/C=C\C/C=C\C/C=C\CCCCC)OCC(CCOS(C)(=O)=O)O1]

A 250 mL RBF was charged with the ketal (Compound 13) (1.34 g, 2.19 mmol), TEA (1 mL, 7.1 mmol) and a stir bar. The flask was flushed with nitrogen, anh. DCM (10 mL) added, and the solution cooled to −15° C. In a separate 50 mL flask, a solution of MsCl (342 μL, 4.4 mmol, 2 eqv.) in anhydrous DCM (15 mL) was prepared, then transferred to the reaction vessel by syringe over 20 minutes. The reaction was stirred for 90 minutes at −15° C., at which point starting material had been consumed. The reaction mixture was diluted with a further 50 mL of DCM, washed with $NaHCO_3$ (2×50 mL), dried ($MgSO_4$) and purified by chromatography. Final yield 1.31 g, 1.90 mmol, 87%.

Synthesis of D-γ-Len-C2K-DMA (Compound 15):

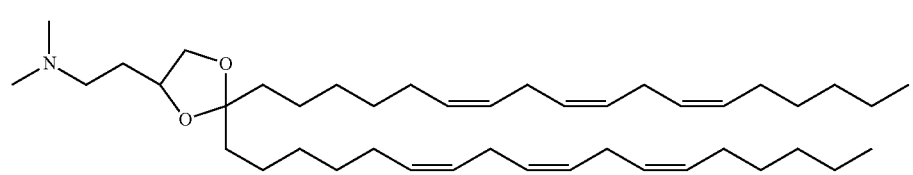 [SMILES: CCCCC/C=C\C/C=C\C/C=C\CCCCCC1(CCCCC/C=C\C/C=C\C/C=C\CCCCC)OCC(CCN(C)C)O1]

A 250 mL RBF was charged with the mesylate (Compound 14) (1.31 g, 1.9 mmol), isopropanol (10 mL) and a stir bar. The flask was flushed with nitrogen, sealed, and a 2.0 M solution of dimethylamine in methanol (60 mL) added via canulla. The reaction was stirred at room temperature for 3 days. The solution was concentrated and purified by chromatography. Final yield 1.1 g, 1.72 mmol, 91%.

Synthesis of CP-γDLen-C2K-DMA (Compound 16):

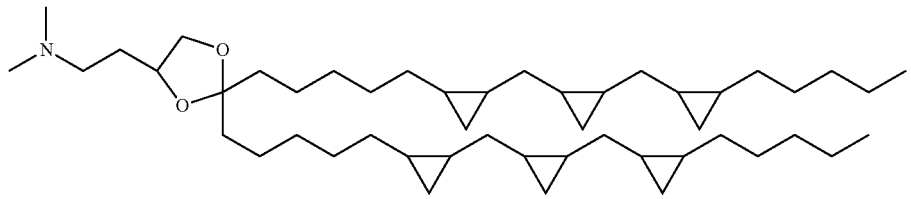 [SMILES: CCCCCC1CC1CC1CC1CC1CC1CCCCCC1(CCCCCC2CC2CC2CC2CC2CC2CCCCC)OCC(CCN(C)C)O1]

To a 250 mL RBF was added γ-Len-C2K (Compound 15) (638 mg, 1 mmol), a stirbar and anh. DCM (40 mL). The flask was flushed with $N_2$ and cooled to 0° C., then a 1M solution of diethylzinc in hexanes added (30 mL, 30 mmol, 5 equivalents per olefin). The solution was stirred for 1 hour at 0° C., then diiodomethane (2.42 mL 30 mmol). The reaction mixture was concentrated and then redissolved in EtOAc (50 mL). The EtOAc was washed successively with 5% HCl (2×50 mL), water (50 mL), NaHCO$_3$ (50 mL), water (50 mL), and brine (50 mL). The aqueous washes were combined and extracted with DCM (2×50 mL). All organics were combined, dried and concentrated to yield crude CP-γ-Len-C2K. As previously, $^1$H-NMR and HPLC indicated some olefins still to be present, so the compound was treated again, using the same procedures and amounts outlined above. This time $^1$H-NMR indicated total conversion of the olefins. Final yield after chromatography was 614 mg, 0.85 mmol, 85%.

Example 9. Synthesis of CP-C2K-DMA

CP-C2K-DMA (Compound 17) having the structure shown below was synthesized as described in Scheme 6 below. CP-C2K-DMA is also known as CP-C2K.

To a solution of DLin-C2K-DMA (1.2 g, 1.87 mmol) in anhydrous $CH_2Cl_2$ (36 mL) at 0° C. under nitrogen was added 2.5 equivalents diethyl zinc (1M solution in hexanes) (18.7 mL) per olefin. The solution was stirred for 75 minutes and then 2.5 equivalents diiodomethane (1.5 mL, 18.7 mmol) per olefin was added. The reaction was stirred overnight at room temp. The white suspension was poured into ice (100 mL) and diluted to 150 mL using ethyl acetate (white solid dissolved upon the addition of ethyl acetate). 5% HCl (50 mL) was added and the aqueous layer backextracted with ethyl acetate (2×100 mL). The combined organics were washed with 5% HCl again, then saturated NaHCO$_3$, water, and brine (150 mL each), dried over MgSO$_4$, filtered, and concentrated to yield a brown yellow oil.

The above procedure was repeated once in order to ensure 100% cyclopropylation of the double bonds. The brown yellow oil was analyzed by HPLC and determined to be >99% pure. The oil was decolorized using a second column (column 2"L×2"W; eluted with 10% ethyl acetate in hexanes) to afford the product as a pale yellow oil. Final yield 740 mg.

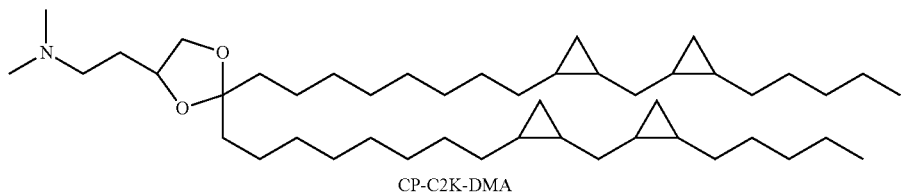 [SMILES: CCCCCC1CC1CC1CC1CCCCCCCCC1(CCCCCCCCC2CC2CC2CC2CCCCC)OCC(CCN(C)C)O1]

CP-C2K-DMA

Scheme 6

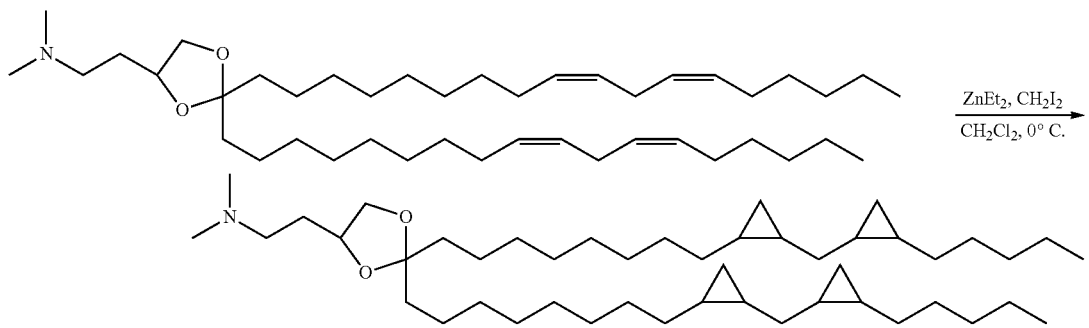

Example 10. Synthesis of LenMC3 and CP-LenMC3

LenMC3 (Compound 20) and CP-LenMC3 (Compound 21) having the structures shown below were synthesized as described in Scheme 7 below. LenMC3 is also known as linolenyl-MC3 and DLen-MC3. CP-LenMC3 is also known as CP-linolenyl-MC3 and CP-DLen-MC3.

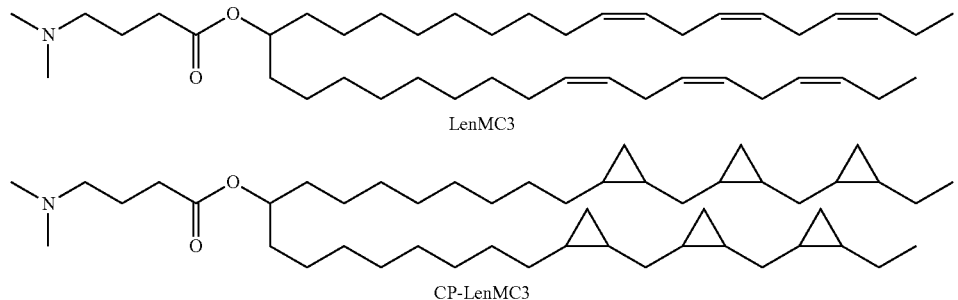

Scheme 7

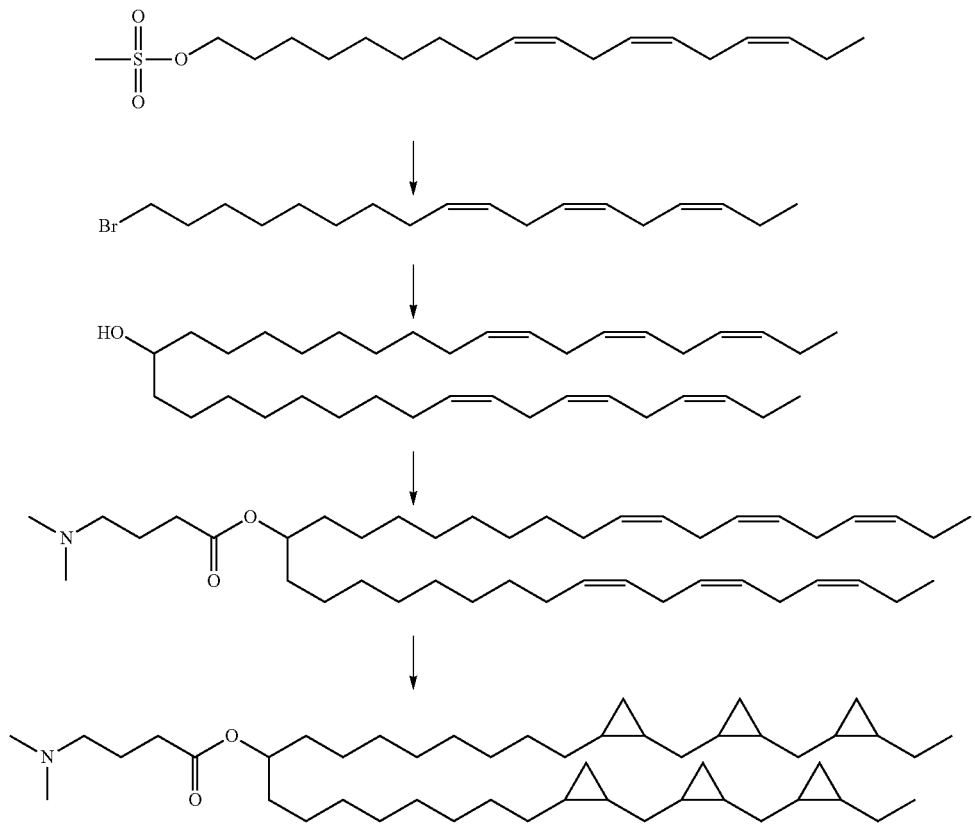

Synthesis of Linolenyl Bromide (Compound 18)

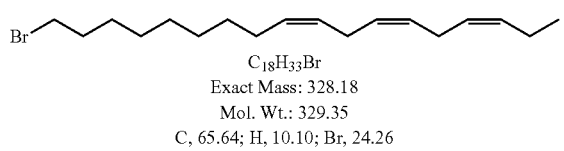

C₁₈H₃₃Br
Exact Mass: 328.18
Mol. Wt.: 329.35
C, 65.64; H, 10.10; Br, 24.26

Magnesium bromide etherate (34 g, 110 mmol) and a stir bar were added to a 2000 mL round bottom flask. The flask was sealed and flushed with nitrogen. Anhydrous diethyl ether (400 mL) was added via canulla. A solution of linolenyl mesylate (20 g, 58 mmol) in anhydrous ether (300 mL) was then added, and the suspension stirred overnight. The suspension was poured into 500 mL of chilled water and transferred to a 2000-mL separating funnel. After shaking, the organic phase was separated. The aqueous phase was then extracted with ether (2×250 mL) and all ether phases combined. The ether phase was washed with water (2×250 mL), brine (250 mL) and dried over anhydrous Mg$_2$SO$_4$. The solution was filtered, concentrated and purified by flash chromatography. Final yield 19.1 g, 100%.

Synthesis of Dilinolenyl Methanol (Compound 19)

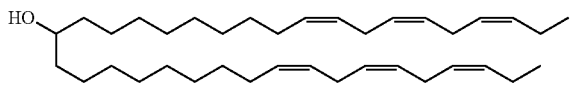

was flushed with nitrogen and anhydrous DCM (40 mL) added, followed by EDCI (FW 191.7, 1.2 g, 6.26 mmol), DIPEA (2.1 mL, 12.1 mmol) and DMAP (150 mg, 1.23 mmol). The reaction was stirred overnight, whereupon TLC indicated >80% conversion. Reaction was diluted with DCM (100 mL) and washed with sat. NaHCO$_3$ (100 mL), water (200 mL) and sat. NaCL (100 mL). Aqueous washes were combined and extracted with DCM (2×50 mL). Organics were then combined, dried (MgSO$_4$) and concentrated to yield a yellow oil with some crystalline matter. This was purified by chromatography to yield Len-MC3 as a pale yellow oil (2.3 g, 3.6 mmol, 76%).

Synthesis of CP-LenMC3 (Compound 21)

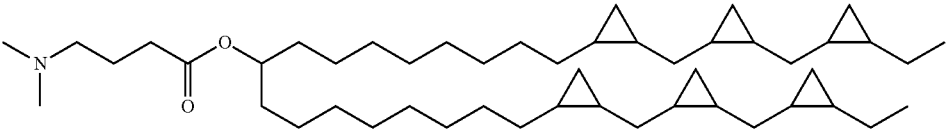

Chemical Formula: C$_{49}$H$_{87}$NO$_2$
Exact Mass: 721.7
Molecular Weight: 722.2
Elemental Analysis: C, 81.49; H, 12.14; N, 1.94; O, 4.43

Magnesium turnings (2.1 g, 87 mmol), 5 crystals of iodine and a stirbar were added to a 1000 mL round-bottom flask. The flask was flushed with nitrogen and a solution of linolenyl bromide (Compound 18) (19.1 g, 58 mmol) in anhydrous diethyl ether (500 mL) added via cannula. The mixture turned cloudy and was refluxed overnight. The mixture was cooled to RT and ethyl formate (4.66 mL, 58 mmol) added via syringe. The addition was made dropwise, directly into the reaction mixture, and the cloudy suspension again stirred overnight. During this time the reaction turned bright yellow. The R.M. was transferred to a 2000-mL sep. funnel with ether (50 mL), and washed with 10% H$_2$SO$_4$ (200 mL), water (2×200 mL) and brine (200 mL). The organic was dried over anhydrous MgSO$_4$, filtered and concentrated. Crude yield was 14.5 g. TLC indicated that majority of product was the methyl formate, which was purified by column chromatography. The purified formate (9.3 g, 16.7 mmol) was transferred to a 1000 mL round bottom flask and EtOH (600 mL) and a stirbar added. With stirring, water (25 mL—forming ~5% aqueous solution) was slowly added, followed by KOH (2.0 g, 35.7 mmol). After 1 hour, the solution had turned pale yellow. TLC indicated reaction had gone to completion. The solution was concentrated by rotovap to 50% of its volume and then poured into 200 mL of 5% HCl. The aqueous phase was extracted with ether (3×200 mL). The ether fractions were combined and washed with water (3×200 mL), dried (MgSO$_4$) and concentrated to yield 8.9 g of dilinolenyl methanol (16.8 mmol, 58%).

Synthesis of Len-MC3 (Compound 20)

To a 250 mL RBF was added Len-MC3 (Compound 20) (1.1 g, 1.72 mmol), a stirbar and anhydrous DCM (40 mL). The flask was flushed with N$_2$ and cooled to 0° C., then a 1M solution of diethylzinc in hexanes added (30 mL, 30 mmol). The solution was stirred for 1 hour at 0° C., then diiodomethane (2.4 mL 30 mmol) added and the reaction stirred overnight at RT. The reaction mixture was concentrated and then redissolved in EtOAc (50 mL). The EtOAc was washed successively with 5% HCl (2×50 mL), water (50 mL), NaHCO$_3$ (50 mL), water (50 mL), and brine (50 mL). The aqueous washes were combined and extracted with DCM (2×50 mL). All organics were combined, dried and concentrated to yield crude CP-Len-MC3. $^1$H-NMR indicated some olefins still to be present, so the compound was treated again, using the same procedures and amounts outlined above. This time, after chromatography, $^1$H-NMR indicated total conversion of the olefins. Final yield 1.0 g, 1.39 mmol, 81%.

Example 11. Synthesis of γ-LenMC3 and CP-γ-LenMC3

γ-LenMC3 (Compound 24) and CP-γ-LenMC3 (Compound 25) having the structures shown below were synthesized as described in Scheme 8 below. γ-LenMC3 is also

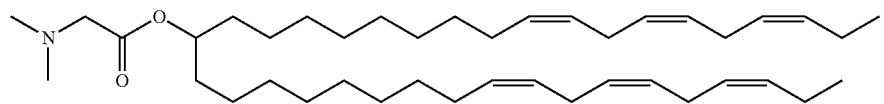

Dilinolenyl methanol (Compound 19) (2.5 g, 4.76 mmol), dimethylaminobutyric acid hydrochloride (970 mg, 5.77 mmol) and a stir bar were added to 100 mL RBF. The flask known as γlinolenyl-MC3, γDLen-MC3, and D-γ-Len-MC3. CP-γ-LenMC3 is also known as CP-γlinolenyl-MC3, CP-γDLen-MC3, and CP-D-γ-Len-MC3.

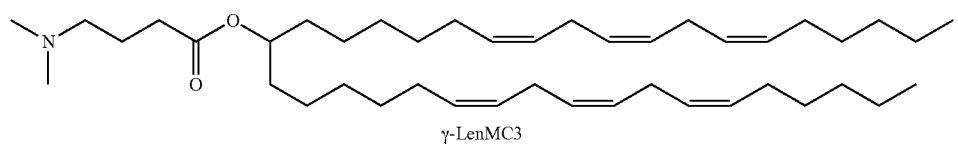
γ-LenMC3
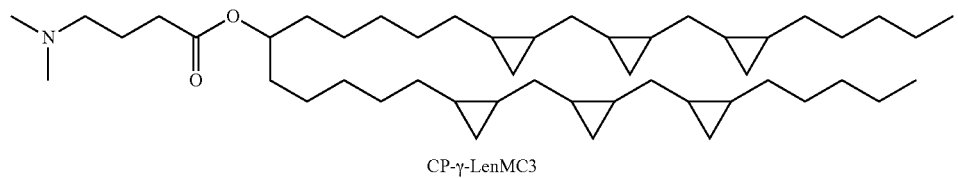
CP-γ-LenMC3
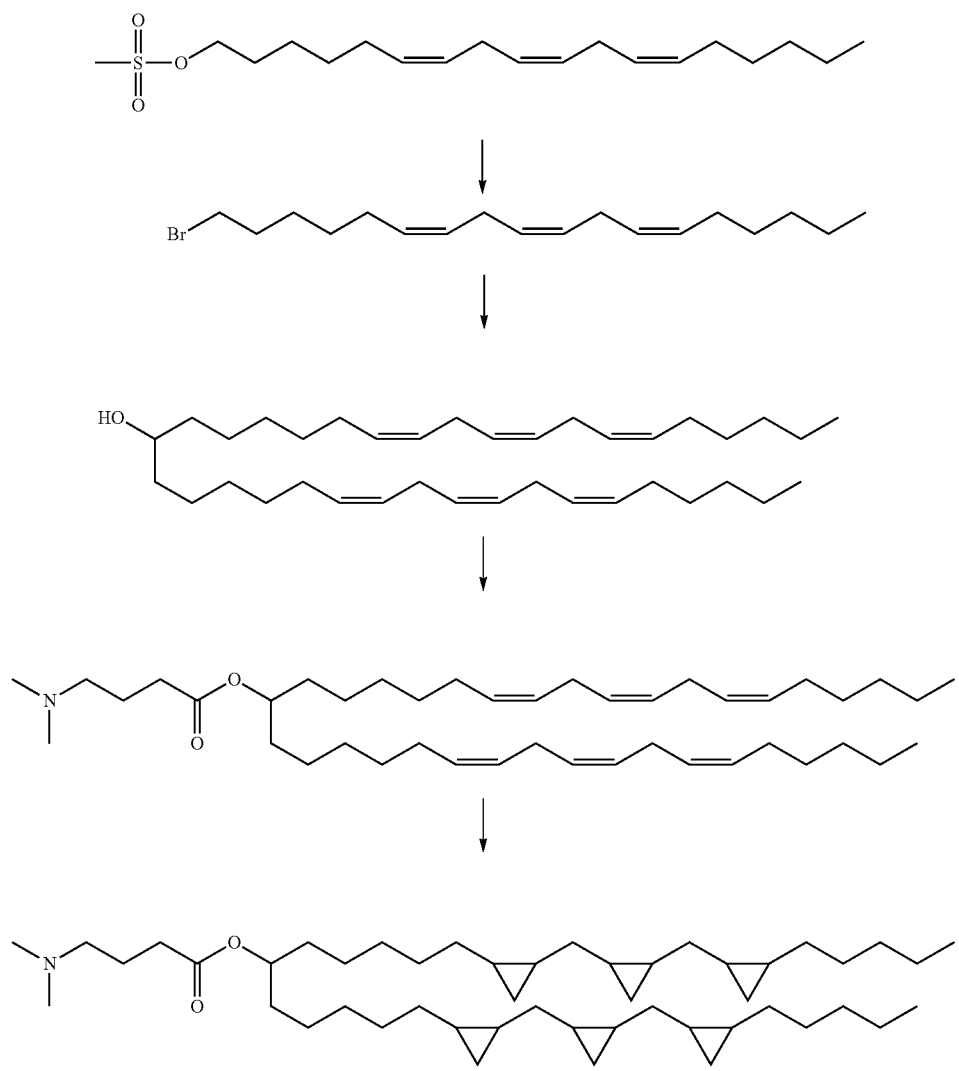
Scheme 8

Synthesis of γ-Linolenyl Bromide (Compound 22)

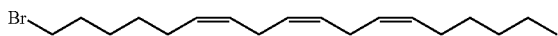

Magnesium bromide etherate (34 g, 110 mmol) and a stir bar were added to a 2000 mL round bottom flask. The flask was sealed and flushed with nitrogen. Anhydrous diethyl ether (400 mL) was added via canulla. A solution of γ-linolenyl mesylate (20 g, 58 mmol) in anhydrous ether (300 mL) was then added, and the suspension stirred overnight. The suspension was poured into 500 mL of chilled water and transferred to a 2000-mL separating funnel. After shaking, the organic phase was separated. The aqueous phase was then extracted with ether (2×250 mL) and all ether phases combined. The ether phase was washed with water (2×250 mL), brine (250 mL) and dried over anhydrous $Mg_2SO_4$. The solution was filtered, concentrated and purified by flash chromatography. Final yield 18.9 g, 99%.

Synthesis of Di-γ-Linolenyl Methanol (Compound 23)

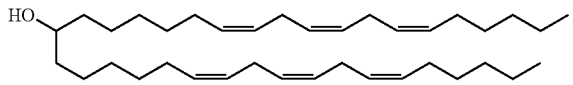 [SMILES: CCCCC/C=C\C/C=C\C/C=C\CCCCCC(O)CCCCC/C=C\C/C=C\C/C=C\CCCCC]

Magnesium turnings (2.1 g, 87 mmol), 5 crystals of iodine and a stirbar were added to a 1000 mL round-bottom flask. The flask was flushed with nitrogen and a solution of γ-linolenyl bromide (Compound 22) (18.9 g, 57 mmol) in anhydrous diethyl ether (500 mL) added via cannula. The mixture turned cloudy and was refluxed overnight. The mixture was cooled to RT and ethyl formate (4.66 mL, 58 mmol) added dropwise. The suspension was stirred overnight, turning bright yellow. The R.M. was transferred to a 2000-mL sep. funnel with ether (50 mL), and washed with 10% sulphuric acid (200 mL), water (2×200 mL) and brine (200 mL). The organic was dried over anhydrous $MgSO_4$, filtered and concentrated. Crude yield was 14.5 g. TLC indicated that majority of product was the methyl formate, which was purified by column chromatography. The purified formate was transferred to a 1000 mL round bottom flask and EtOH (600 mL) and a stirbar added. With stirring, water (25 mL—forming ~5% aqueous solution) was slowly added, followed by KOH (2.0 g, 35.7 mmol). After 1 hour, solution had turned pale yellow. TLC indicated reaction had gone to completion. The solution was concentrated by rotovap to 50% of its volume and then poured into 200 mL of 5% HCl. The aqueous phase was extracted with ether (3×200 mL). The ether fractions were combined and washed with water (3×200 mL), dried ($MgSO_4$) and concentrated to yield 8.8 g of di-γ-linolenyl methanol (16.8 mmol, 58%).

Synthesis of γ-LenMC3 (Compound 24)

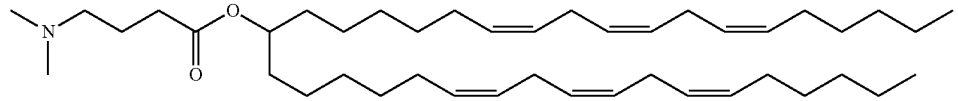 [SMILES: CCCCC/C=C\C/C=C\C/C=C\CCCCCC(CCCCC/C=C\C/C=C\C/C=C\CCCCC)OC(=O)CCCN(C)C]

Di-γ-linolenyl methanol (Compound 23) (2.5 g, 4.76 mmol), dimethylaminobutyric acid hydrochloride (970 mg, 5.77 mmol) and a stir bar were added to 100 mL RBF. The flask was flushed with nitrogen and anhydrous DCM (40 mL) added, followed by EDCI (1.2 g, 6.26 mmol), DIPEA (2.1 mL, 12.1 mmol) and DMAP (150 mg, 1.23 mmol). The reaction was stirred overnight. The reaction was diluted with DCM (100 mL) and washed with sat. $NaHCO_3$ (100 mL), water (200 mL) and sat. NaCL (100 mL). Aqueous washes were combined and extracted with DCM (2×50 mL). Organics were then combined, dried ($MgSO_4$) and concentrated to yield a yellow oil. This was purified by chromatography to yield γ-Len-MC3 as a pale yellow oil (2.6 g, 4.1 mmol, 86%).

Synthesis of CP-γ-LenMC3 (Compound 25)

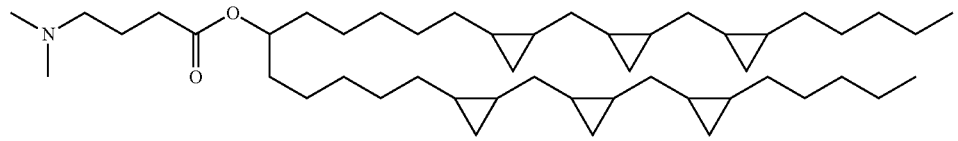 [SMILES: CCCCCC1CC1CC1CC1CC1CC1CCCCCC(CCCCCC1CC1CC1CC1CC1CC1CCCCC)OC(=O)CCCN(C)C]

To a 250 mL RBF was added γ-LenMC3 (Compound 24) (1.28 g, 2.0 mmol), a stirbar and anhydrous DCM (40 mL). The flask was flushed with $N_2$ and cooled to 0° C., then a 1M solution of diethylzinc in hexanes added (30 mL, 30 mmol, ~5 equivalents per olefin).

The solution was stirred for 1 hour at 0° C., then diiodomethane (2.4 mL 50 mmol) added and the reaction stirred overnight at RT. The reaction mixture was concentrated and then redissolved in EtOAc (50 mL). The EtOAc was washed successively with 5% HCl (2×50 mL), water (50 mL), NaHCO$_3$ (50 mL), water (50 mL), and brine (50 mL). The aqueous washes were combined and extracted with DCM (2×50 mL). All organics were combined, dried and concentrated to yield crude CP-γ-LenMC3. $^1$H-NMR indicated some olefins still to be present, so the compound was treated again, using the same procedures and amounts outlined above. This time $^1$H-NMR indicated total conversion of the olefins. Final yield after chromatography was 1.3 g, 1.8 mmol, 90%.

Example 12. Synthesis of MC3

MC3 (Compound 26) having the structure shown below was synthesized as described in Scheme 9 below.

combined. The ether phase was washed with water (2×250 mL), brine (250 mL) and dried over anhydrous Mg$_2$SO$_4$. The solution was filtered, concentrated and purified by flash chromatography. Final yield 18.9 g, 99%.

STEP 2: A 1 liter RBF was charged with magnesium turnings (11.1 g, 463 mmol), anhydrous THF (65 mL) and stir-bar and flushed with nitrogen. In a separate flask, a solution of linoleyl bromide (140 g, 425 mL) in anhydrous THF (150 mL) was prepared, and 20 mL of this solution added to the magnesium. When most of the heat had dissipated, the remainder of the bromide was added over a period of 15 minutes. Temperature was then maintained at 45° C. for 4 h. The reaction was then cooled (0° C.). Using a dropping funnel, a solution of ethyl formate (32.4 g, 438 mmol) in anhydrous THF (150 mL) was added over a 40

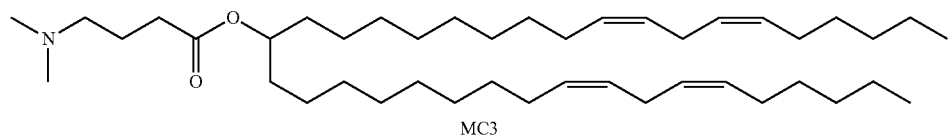 [SMILES: CCCCC/C=C\C/C=C\CCCCCCCCC(CCCCCCCC/C=C\C/C=C\CCCCC)OC(=O)CCCN(C)C]

MC3

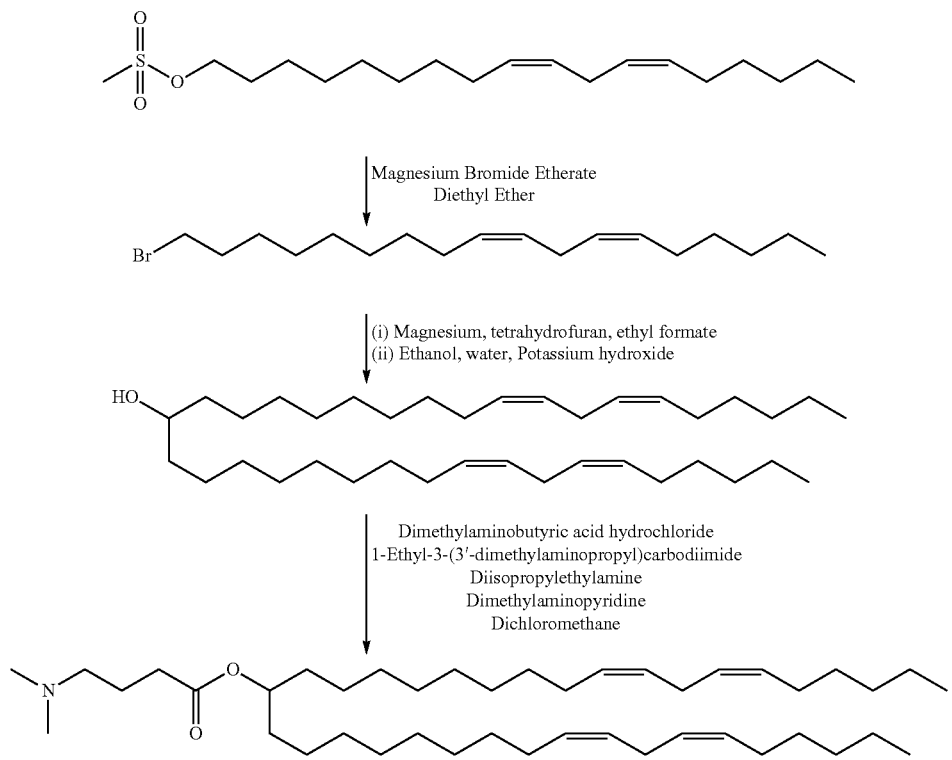

Scheme 9

STEP 1: Magnesium bromide etherate (34 g, 110 mmol) and a stir bar were added to a 2000 mL round bottom flask. The flask was sealed and flushed with nitrogen. Anhydrous diethyl ether (400 mL) was added via canulla. A solution of linolenyl mesylate (20 g, 58 mmol) in anhydrous ether (300 mL) was then added, and the suspension stirred overnight. The suspension was poured into 500 mL of chilled water and transferred to a 2000-mL separating funnel. After shaking, the organic phase was separated. The aqueous phase was then extracted with ether (2×250 mL) and all ether phases minute period. The reaction was stirred overnight at room temperature. The reaction was cooled to −15° C. and 5N HCl (185 mL) added slowly. The mixture was transferred to a 2 L separating funnel separated. Water (150 mL) and hexane (150 mL) were added, the mixture washed, and again the aqueous removed. The organic was washed a final time with water (150 mL) and then concentrated to a yellow oil. The yellow oil was stirred with a mixture of EtOH (210 mL), water (30 mL) and KOH (15.8 g) for 1.5 h at room temp. The EtOH was evaporated and the residue treated with hexane (50 mL). 5N HCl (200 mL) was added via dropping funnel. The organic was washed with water (2×50 mL) evaporated, dried and purified by chromatography (0-5% EtOAc in hexane, 91 g, 81%).

STEP 3: Dilinoleylmethanol (7.8 g, 14.9 mmol), dimethylaminobutyric acid hydrochloride (2.99 g, 17.8 mmol) and a stir bar were added to 500 mL RBF. The flask was flushed with nitrogen and anh. DCM (120 mL) added, followed by EDCI (3.6 g, 18.8 mmol), DIPEA (6.3 mL, 36.3 mmol) and DMAP (450 mg, 3.69 mmol). The reaction was stirred overnight. The reaction was diluted with DCM (300 mL) and washed with sat. NaHCO$_3$ (200 mL), water (300 mL) and sat. NaCL (200 mL). Each aq. wash was extracted once with DCM (50 mL). Organics were combined, dried (MgSO$_4$) and concentrated to yield a yellow oil with some crystalline matter. This was purified by chromatography (0-2% MeOH in CHCl$_3$) to yield Lin-MC3 as a pale yellow oil (9.0 g, 14.1 mmol, 95%).

Example 13. Synthesis of CP-MC3

CP-MC3 (Compound 27) having the structure shown below was synthesized as described in Scheme 10 below.

In some embodiments, siRNA molecules were encapsulated into serum-stable nucleic acid-lipid particles (SNALP) composed of the following lipids: (1) the lipid conjugate PEG2000-C-DMA (3-N-[(-methoxypoly(ethylene glycol) 2000)carbamoyl]-1,2-dimyristyloxypropylamine); (2) one or more cationic lipids or salts thereof (e.g., cationic lipids of Formula I-III of the invention and/or other cationic lipids described herein); (3) the phospholipid DPPC (1,2-dipalmitoyl-sn-glycero-3-phosphocholine) (Avanti Polar Lipids; Alabaster, Ala.); and (4) synthetic cholesterol (Sigma-Aldrich Corp.; St. Louis, Mo.) in the molar ratio 1.4:57.1:7.1: 34.3, respectively. In other words, siRNA molecules were encapsulated into SNALP of the following "1:57" formulation: 1.4% PEG2000-C-DMA; 57.1% cationic lipid; 7.1% DPPC; and 34.3% cholesterol. It should be understood that the 1:57 formulation is a target formulation, and that the amount of lipid (both cationic and non-cationic) present and the amount of lipid conjugate present in the formulation may vary. Typically, in the 1:57 formulation, the amount of cationic lipid will be 57.1 mol %±5 mol %, and the amount of lipid conjugate will be 1.4 mol %±0.5 mol %, with the

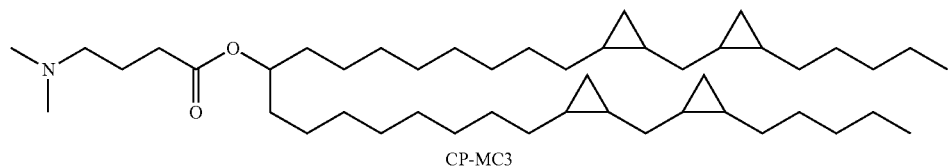 [SMILES: CCCCCC1CC1CC1CC1CCCCCCCCC(CCCCCCCCC1CC1CC1CC1CCCCC)OC(=O)CCCN(C)C]

CP-MC3

Scheme 10

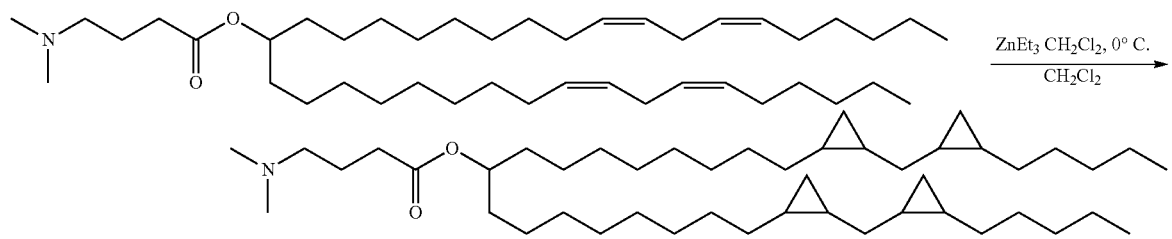

To a solution of MC3 (2.1 g, 3.27 mmol) in anhydrous CH$_2$Cl$_2$ (60 mL) at 0° C. under nitrogen was added 2.5 equivalents diethyl zinc (1M solution in hexanes) (31 mL, 31 mmol). The solution was stirred for 1 hour and then 2.5 equivalents diiodomethane (2.5 mL, 31 mmol) added. The reaction was stirred overnight at room temp. The white suspension was poured into ice (50 mL) and diluted to 200 mL using ethyl acetate (white solid dissolved). 5% HCl (100 mL) was added to wash. The aqueous (acidic) layer was removed and extracted with ethyl acetate (2×125 mL). The organic (top) layer was washed again with 5% HCl, then saturated NaHCO$_3$, water, and brine (150 mL each), dried on MgSO$_4$, filtered, and concentrated to yield a cloudy pale yellow oil. The procedure above was repeated once to ensure 100% cyclopropylation. Product was a pale yellow oil. The oil was purified by column chromatography eluting with CHCl$_3$ to afford a pale yellow oil. Final yield 1.11 g, 51%.

Example 14. Lipid Encapsulation of siRNA

All siRNA molecules used in these studies were chemically synthesized and annealed using standard procedures.

balance of the 1:57 formulation being made up of non-cationic lipid (e.g., phospholipid, cholesterol, or a mixture of the two).

In other embodiments, siRNA were encapsulated into SNALP composed of the following lipids: (1) the lipid conjugate PEG750-C-DMA (3-N-[(-Methoxypoly(ethylene glycol)750)carbamoyl]-1,2-dimyristyloxypropylamine); (2) one or more cationic lipids or salts thereof (e.g., cationic lipids of Formula I-III of the invention and/or other cationic lipids described herein); (3) the phospholipid DPPC; and (4) synthetic cholesterol in the molar ratio 6.76:54.06:6.75: 32.43, respectively. In other words, siRNA were encapsulated into SNALP of the following "7:54" formulation: 6.76 mol % PEG750-C-DMA; 54.06 mol % cationic lipid; 6.75 mol % DPPC; and 32.43 mol % cholesterol. Typically, in the 7:54 formulation, the amount of cationic lipid will be 54.06 mol %±5 mol %, and the amount of lipid conjugate will be 6.76 mol %±1 mol %, with the balance of the 7:54 formulation being made up of non-cationic lipid (e.g., phospholipid, cholesterol, or a mixture of the two).

For vehicle controls, empty particles with identical lipid composition may be formed in the absence of siRNA.

Example 15. pK$_a$ Measurements of SNALP Formulations Containing Novel Cyclic Cationic Lipids This example demonstrates the determination of pK$_a$ values of various 1:57 SNALP formulations containing novel cyclic cationic lipids described herein with an siRNA targeting apolipoprotein B (ApoB).

1:57 SNALP formulations containing encapsulated ApoB siRNA were prepared as described in Section VI above with the following cationic lipids: (1) DLinDMA; (2) CP-DLinDMA; (3) CP-DLenDMA; (4) CP-γ-DLenDMA ("CP-g-DLenDMA"); (5) CP-DODMA; (6) CP-DPetroDMA; (7) C2-TLinDMA; (8) γ-LenMC3 ("g-Len-MC3"); (9) CP-γ-LenMC3 ("CP-g-Len-MC3"); (10) LenMC3; and (11) CP-LenMC3.

The apparent pK$_a$ of the cationic lipids present in these SNALP formulations was determined using a 2-(p-toluidinyl)-naphthalene-6-sodium sulfonate (TNS) assay. TNS is a negatively-charged indicator of membrane potential that is electrostatically attracted to positively charged membranes (see, Bailey and Cullis, *Biochemistry,* 33 12573-80 (1994)). Subsequent adsorption to the lipid membrane results in the immediate environment of the TNS becoming more lipophilic, removing the water molecules that otherwise quench TNS fluorescence. As a result, TNS measures the surface potential of the particle, wherein the more positive the surface potential, the greater the level of fluorescence. The surface pK$_a$ values of each SNALP formulation were determined by varying the local pH in the presence of TNS. By plotting fluorescence versus pH, the pK$_a$ of the cationic lipid can be estimated in the particle as the pH where fluorescence equals 50% of total fluorescence.

Figure 2:
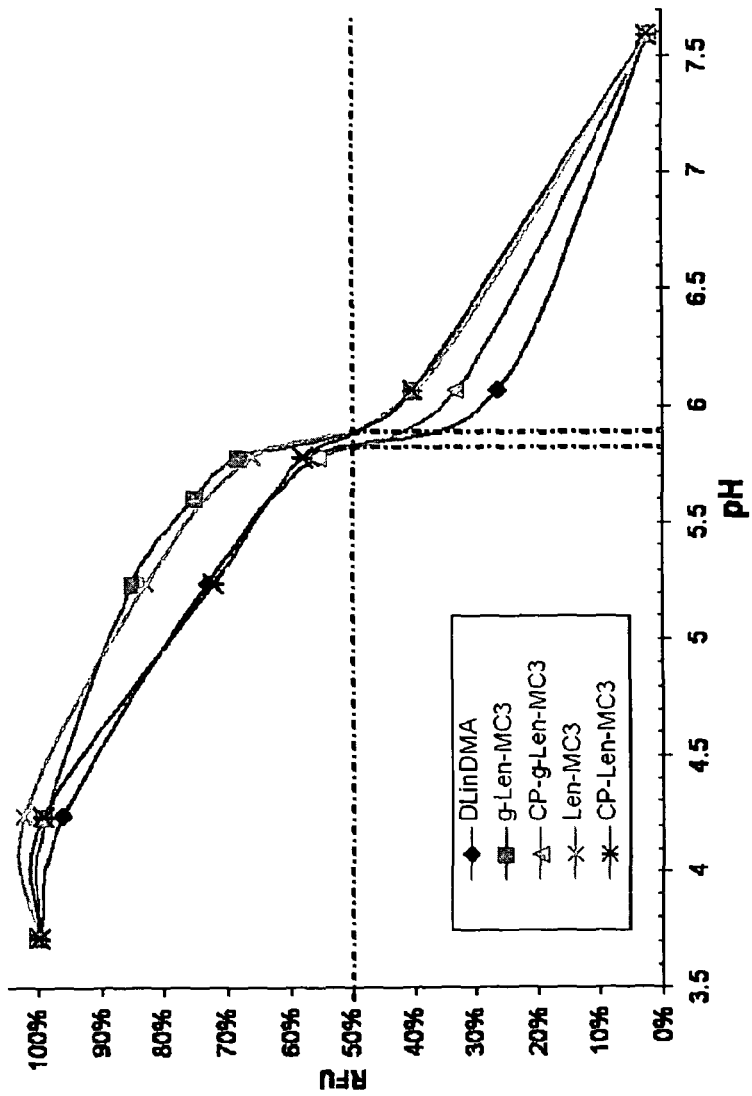
FIG. 2 shows the apparent $pK_a$ values of exemplary SNALP formulations containing cationic lipids of Formula III.

FIGS. 1-2 show the results of the TNS assays, wherein the 1:57 SNALP have the following pK$_a$ values: (1) DLinDMA ~5.8; (2) CP-DLinDMA ~5.8; (3) CP-DLenDMA ~5.85; (4) CP-g-DLenDMA ~5.8; (5) CP-DODMA ~5.8; (6) CP-DPetroDMA ~5.95; (7) C2-TLinDMA ~5.85; (8) g-Len-MC3~6.1; (9) CP-g-Len-MC3~6.0; (10) LenMC3~6.1; and (11) CP-LenMC3~6.1.

Example 16. Characterization of SNALP Formulations Containing Novel Cyclic Cationic Lipids This example demonstrates the efficacy of 1:57 SNALP formulations containing various novel cyclic cationic lipids of Formula I described herein with an siRNA targeting ApoB in a mouse liver model. The ApoB siRNA sequence used in this study is provided in Table 1.

1:57 SNALP formulations containing encapsulated ApoB siRNA were prepared as described in Section VI above with the following cationic lipids: (1) DLinDMA; (2) CP-DLinDMA; (3) CP-DLenDMA; (4) CP-γ-DLenDMA ("CP-g-DLenDMA"); (5) CP-DODMA; (6) CP-DPetroDMA; and (7) C2-TLinDMA. Table 2 provides exemplary features of these SNALP formulations, including particle size, polydispersity, and percent encapsulation.

TABLE 2

|  | Size (nm) | Poly | Encapsulation % |
|---|---|---|---|
| 1:57 DLinDMA | 76.11 | 0.045 | 81 |
| 1:57 CP-DODMA | 77.77 | 0.034 | 87 |
| 1:57 CP-DPetroDMA | 75.83 | 0.035 | 90 |
| 1:57 CP-DLinDMA | 72.39 | 0.028 | 90 |
| 1:57 CP-DLenDMA | 75.82 | 0.024 | 89 |
| 1:57 CP-g-DLenDMA | 68.15 | 0.062 | 83 |

Each SNALP formulation (6:1 L:D) was administered by intravenous (IV) injection at 0.1 mg/kg into female Balb/c mice (n=3 per group). Liver ApoB mRNA levels were evaluated at 48 hours after SNALP administration by a branched DNA assay (QuantiGene assay) to assess ApoB mRNA relative to the housekeeping gene GAPDH.

Figure 3:
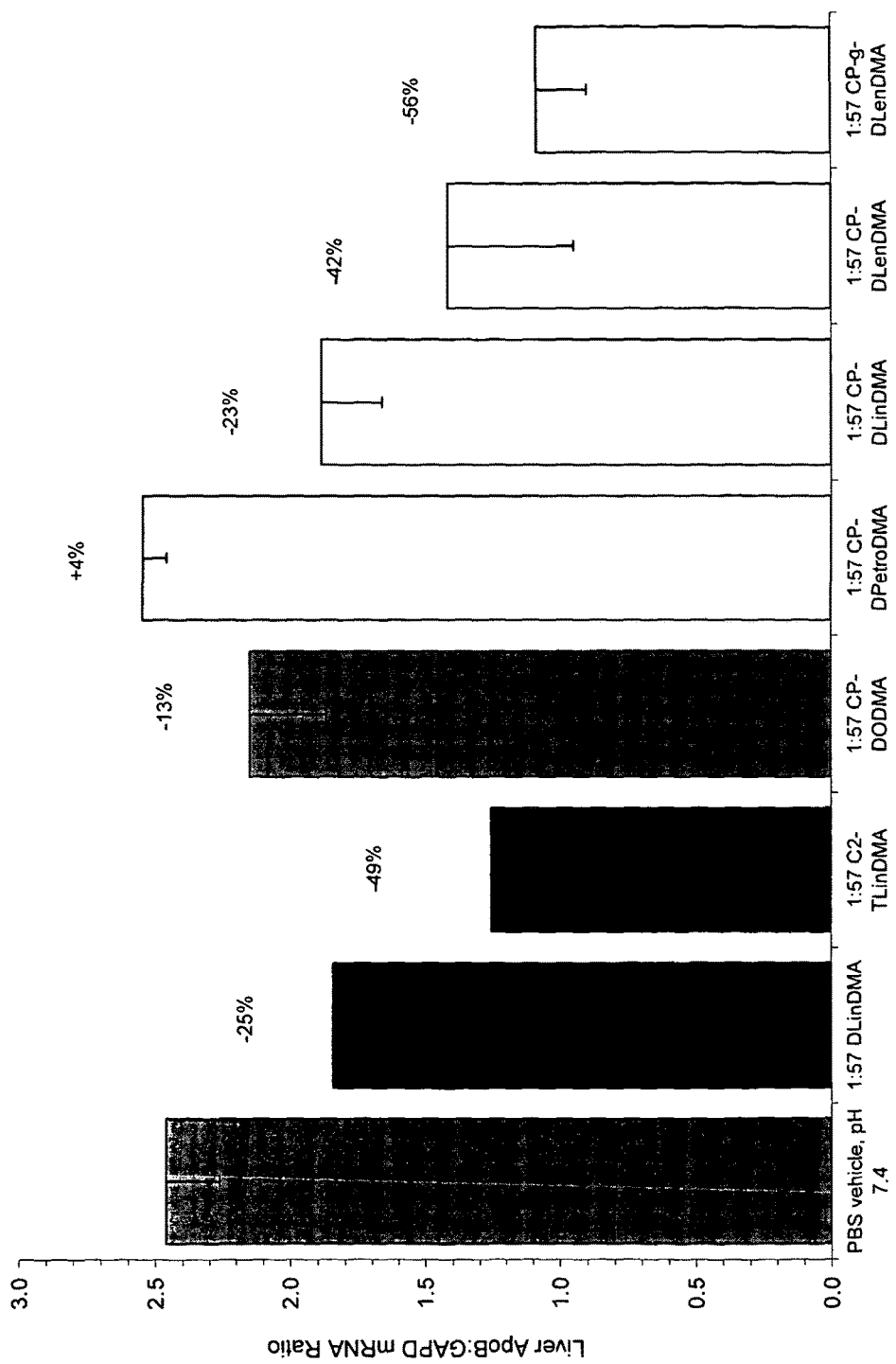
FIG. 3 shows a comparison of the liver ApoB mRNA knockdown activity of exemplary SNALP formulations containing cationic lipids of Formula I.

FIG. 3 shows a comparison of the liver ApoB mRNA knockdown activity of each of these SNALP formulations (Error bars=SD). In particular, FIG. 3 shows that a SNALP formulation containing either CP-DLinDMA, CP-DLenDMA, or CP-γ-DLenDMA displayed similar or greater ApoB silencing activity compared to a SNALP formulation containing the DLinDMA benchmark cationic lipid. Notably, SNALP formulations containing the novel cyclic cationic lipids of Formula I displayed improved stability over SNALP formulations containing their polyunsaturated counterparts when evaluated under various different storage conditions using techniques such as, e.g., analysis of any change in particle size over time and/or determination of any degradation of the nucleic acid payload and/or cationic lipid.

Example 17. Characterization of Additional SNALP Formulations Containing Novel Cyclic Cationic Lipids This example demonstrates the efficacy of 1:57 SNALP formulations containing various novel cyclic cationic lipids of Formula II described herein with an siRNA targeting ApoB in a mouse liver model. The ApoB siRNA sequence used in this study is provided in Table 1 above.

1:57 SNALP formulations containing encapsulated ApoB siRNA were prepared as described in Section VI above with

TABLE 1

| siRNA | ApoB siRNA Sequence | % 2'OMe-Modified | % Modified in DS Region |
|---|---|---|---|
| ApoB-10164 | 5'-AGUGUCAUCACACUGAAUACC-3' (SEQ ID NO: 1)<br>3'-GUUCACAGUAGUGUGACUUAU-5' (SEQ ID NO: 2) | 7/42 = 16.7% | 7/38 = 18.4% |

Column 1: The number after "ApoB" refers to the nucleotide position of the 5' base of the sense strand relative to the human ApoB mRNA sequence NM_000384.
Column 2: 2'OMe nucleotides are indicated in bold and underlined. The 3'-overhangs on one or both strands of the siRNA molecule may alternatively comprise 1-4 deoxythymidine (dT) nucleotides, 1-4 modified and/or unmodified uridine (U) ribonucleotides, or 1-2 additional ribonucleotides having complementarity to the target sequence or the complementary strand thereof.
Column 3: The number and percentage of 2'OMe-modified nucleotides in the siRNA molecule are provided.
Column 4: The number and percentage of modified nucleotides in the double-stranded (DS) region of the siRNA molecule are provided.

1:57 SNALP formulations containing encapsulated ApoB siRNA were prepared as described in Section VI above with the following cationic lipids: (1) DLin-C2K-DMA ("C2K"); (2) DLin-M-C3-DMA ("MC3"); (3) LenMC3 ("DLen- MC3"); (4) CP-LenMC3 ("CP-DLen-MC3"); (5) D-γ-Len-C2K-DMA ("g-DLen-C2K-DMA"); (6) CP-D-γ-Len-C2K-DMA ("CP-g-DLen-C2K-DMA"); (7) DLen-C2K-DMA; and (8) CP-DLen-C2K-DMA.

For dose response studies, SNALP formulations were administered by IV injection at 0.01 mg/kg, 0.033 mg/kg, or 0.1 mg/kg into female Balb/c mice (n=3 per group). Liver ApoB mRNA levels were evaluated at 48 hours after SNALP administration by a branched DNA assay (Quanti-Gene assay) to assess ApoB mRNA relative to the housekeeping gene GAPDH.

Figure 4:
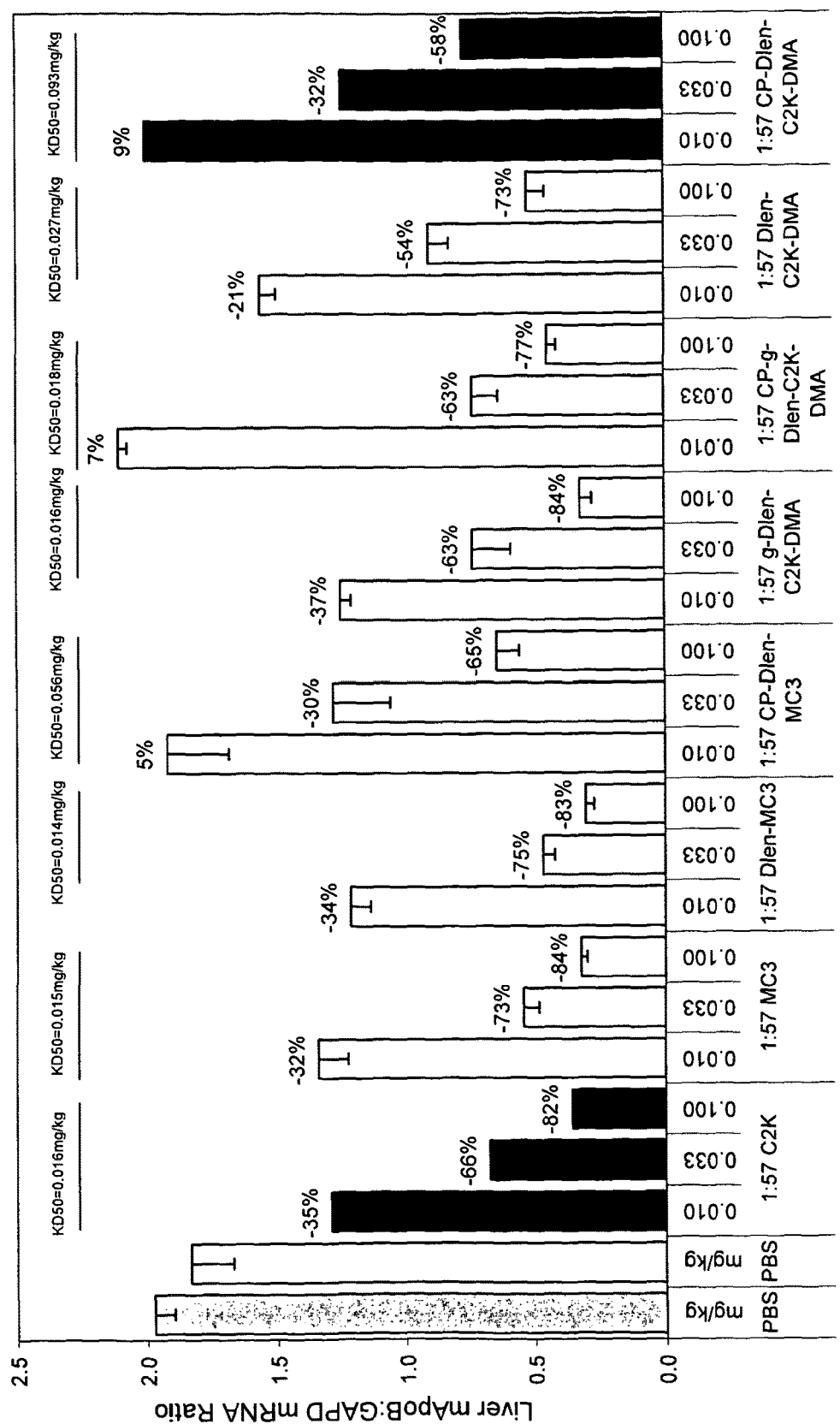
FIG. 4 shows a comparison of the liver ApoB mRNA knockdown activity of exemplary SNALP formulations containing cationic lipids of Formulas II-III.

FIG. 4 shows a comparison of the liver ApoB mRNA knockdown activity of each of these SNALP formulations at three different doses (Error bars=SD), as well as the KD50 values obtained for each of these formulations. In particular, FIG. 4 shows that a SNALP formulation containing CP-g-DLen-C2K-DMA displayed similar ApoB silencing activity at higher doses and similar KD50 value compared to a SNALP formulation containing the C2K benchmark cationic lipid. Furthermore, FIG. 4 shows that a SNALP formulation containing CP-DLen-C2K-DMA displayed considerable potency in silencing ApoB mRNA expression. Notably, SNALP formulations containing the novel cyclic cationic lipids of Formula II displayed improved stability over SNALP formulations containing their polyunsaturated counterparts when evaluated under various different storage conditions using techniques such as, e.g., analysis of any change in particle size over time and/or determination of any degradation of the nucleic acid payload and/or cationic lipid.

Example 18. Characterization of Additional SNALP Formulations Containing Novel Cyclic Cationic Lipids This example demonstrates the efficacy of 1:57 SNALP formulations containing various novel cyclic cationic lipids of Formula III described herein with an siRNA targeting ApoB in a mouse liver model. The ApoB siRNA sequence used in this study is provided in Table 1 above.

1:57 SNALP formulations containing encapsulated ApoB siRNA were prepared as described in Section VI above with the following cationic lipids: (1) DLin-C2K-DMA ("C2K"); (2) DLin-M-C3-DMA ("MC3"); (3) γ-LenMC3 ("g-Len-MC3"); (4) CP-γ-LenMC3 ("CP-g-Len-MC3"); (5) LenMC3; and (6) CP-LenMC3. Table 3 provides exemplary features of these SNALP formulations, including particle size, polydispersity, and percent encapsulation.

TABLE 3

| Formulation | Initial Size (nm) | Final Size (nm) | Poly | Encaps | Total siRNA (mg/ml) |
|---|---|---|---|---|---|
| 1:57 C2K | 80 | 88 | 0.030 | 98% | 5.2 |
| 1:57 MC3 | 80 | 84 | 0.034 | 99% | 4.6 |
| 1:57 g-Len-MC3 | 76 | 79 | 0.052 | 98% | 4.8 |
| 1:57 CP-g-Len-MC3 | 79 | 82 | 0.037 | 100% | 5.1 |
| 1:57 Len-MC3 | 79 | 84 | 0.049 | 98% | 5.8 |
| 1:57 CP-Len-MC3 | 76 | 83 | 0.029 | 100% | 5.6 |

For dose response studies, SNALP formulations were administered by IV injection at 0.01 mg/kg, 0.033 mg/kg, or 0.1 mg/kg into female Balb/c mice (n=3 per group). Liver ApoB mRNA levels were evaluated at 48 hours after SNALP administration by a branched DNA assay (Quanti-Gene assay) to assess ApoB mRNA relative to the housekeeping gene GAPDH.

Figure 5:
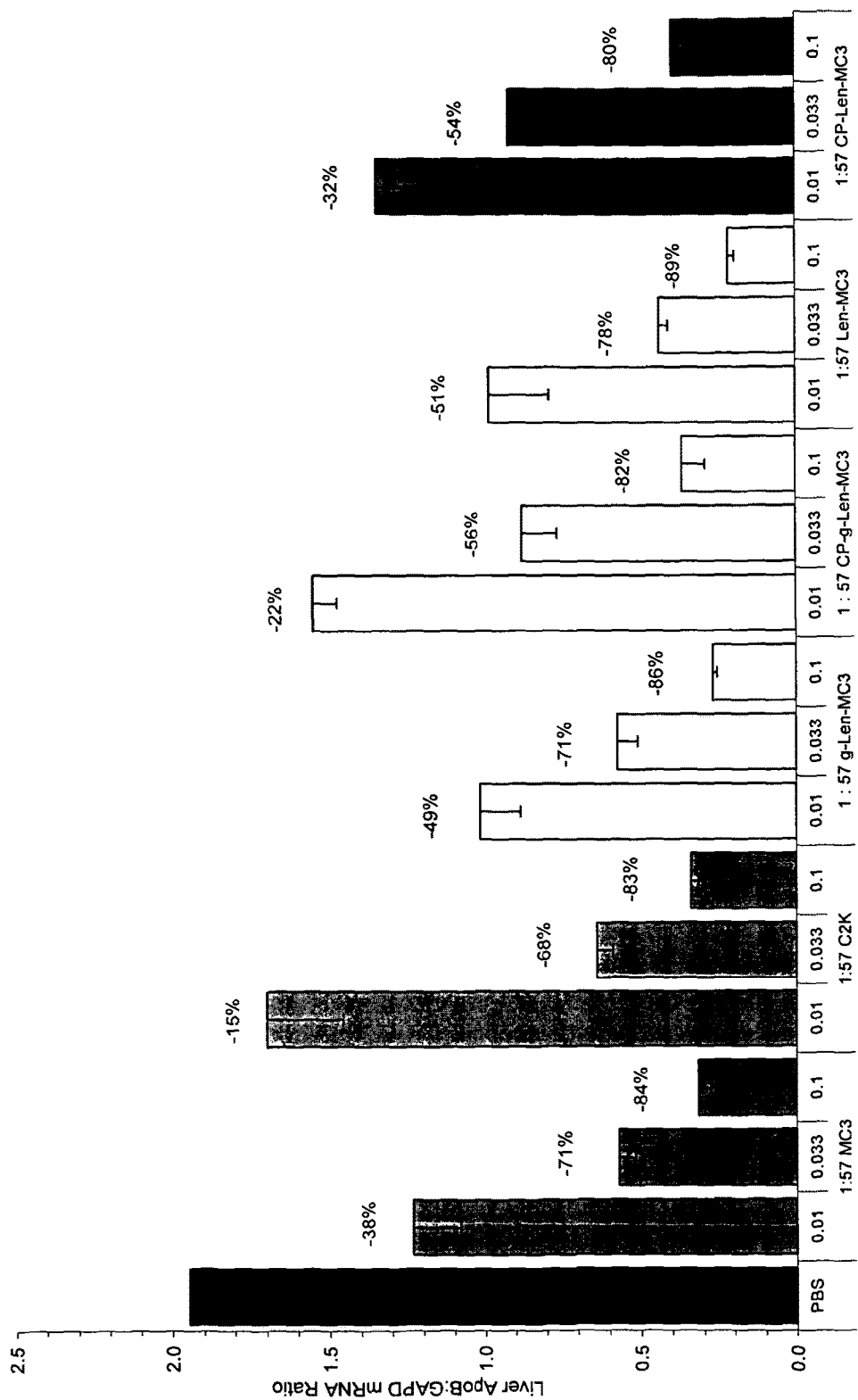
FIG. 5 shows a comparison of the liver ApoB mRNA knockdown activity of exemplary SNALP formulations containing cationic lipids of Formula III.
Figure 6:
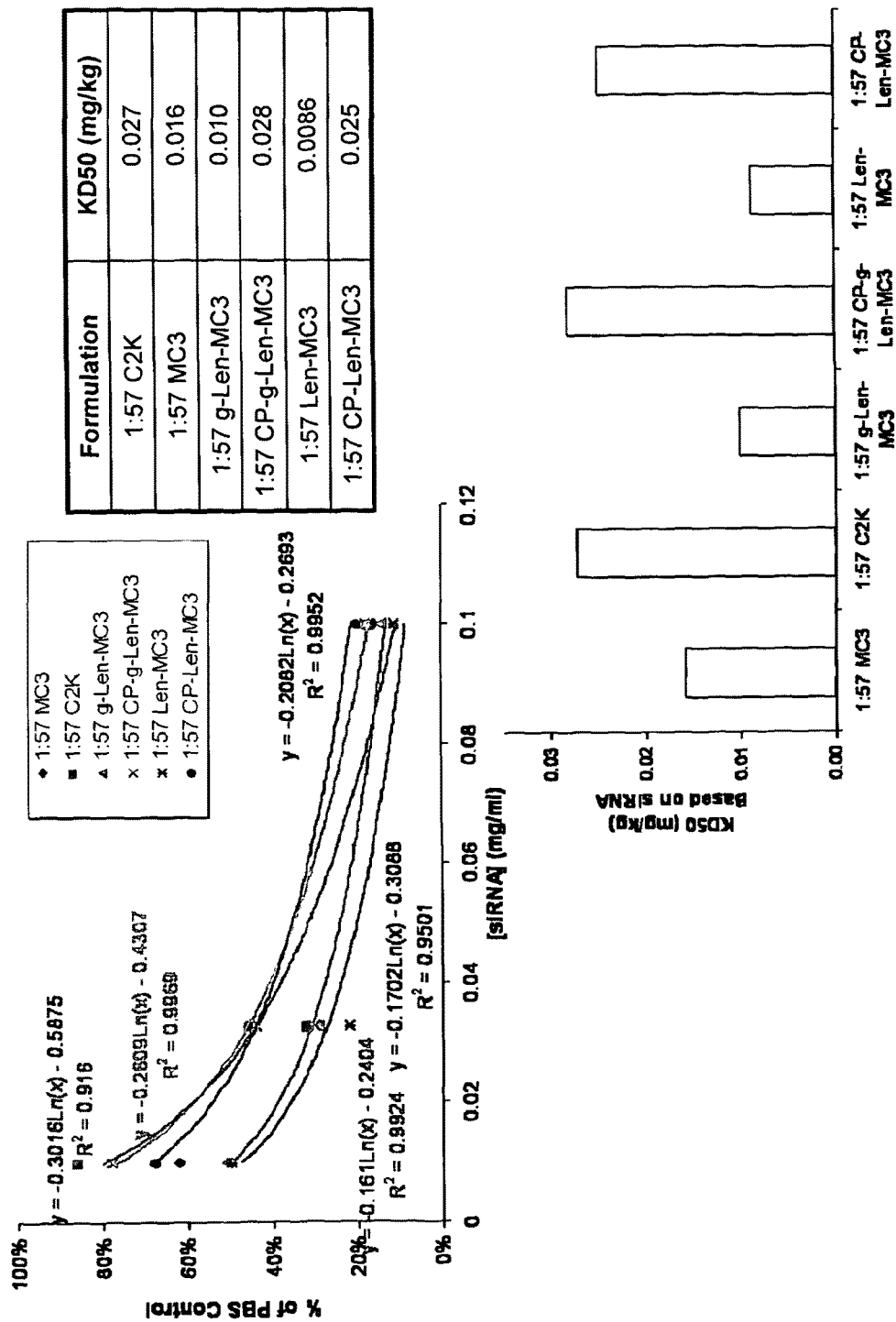
FIG. 6 shows the KD50 calculation and values obtained for each of the exemplary SNALP formulations containing cationic lipids of Formula III.

FIG. 5 shows a comparison of the liver ApoB mRNA knockdown activity of each of these SNALP formulations at three different doses (Error bars=SD). FIG. 6 shows the KD50 calculation and values obtained for each of these SNALP formulations. In particular, FIG. 5 shows that a SNALP formulation containing either CP-γ-LenMC3 or CP-LenMC3 displayed similar ApoB silencing activity compared to a SNALP formulation containing the C2K benchmark cationic lipid at all three doses. FIG. 6 shows that a SNALP formulation containing either CP-γ-LenMC3 or CP-LenMC3 displayed similar KD50 values compared to a SNALP formulation containing the C2K benchmark cationic lipid. Notably, SNALP formulations containing the novel cyclic cationic lipids of Formula III displayed improved stability over SNALP formulations containing their polyunsaturated counterparts when evaluated under various different storage conditions using techniques such as, e.g., analysis of any change in particle size over time and/or determination of any degradation of the nucleic acid payload and/or cationic lipid.

Example 19. Characterization of Additional SNALP Formulations Containing Novel Cyclic Cationic Lipids This example demonstrates the efficacy of 1:57 SNALP formulations containing various novel cyclic cationic lipids of Formula II-III described herein with an siRNA targeting ApoB in a mouse liver model. The ApoB siRNA sequence used in this study is provided in Table 1 above.

1:57 SNALP formulations containing encapsulated ApoB siRNA were prepared as described in Section VI above with the following cationic lipids: (1) DLin-C2K-DMA ("C2K"); (2) MC2MC; (3) MC3 Ether; (4) Pan-MC3; (5) CP-MC3; and (6) CP-C2K.

SNALP formulations were administered by IV injection at 0.05 mg/kg into female Balb/c mice (n=3 per group). Liver ApoB mRNA levels were evaluated at 48 hours after SNALP administration by a branched DNA assay (Quanti-Gene assay) to assess ApoB mRNA relative to the housekeeping gene GAPDH.

Figure 7:
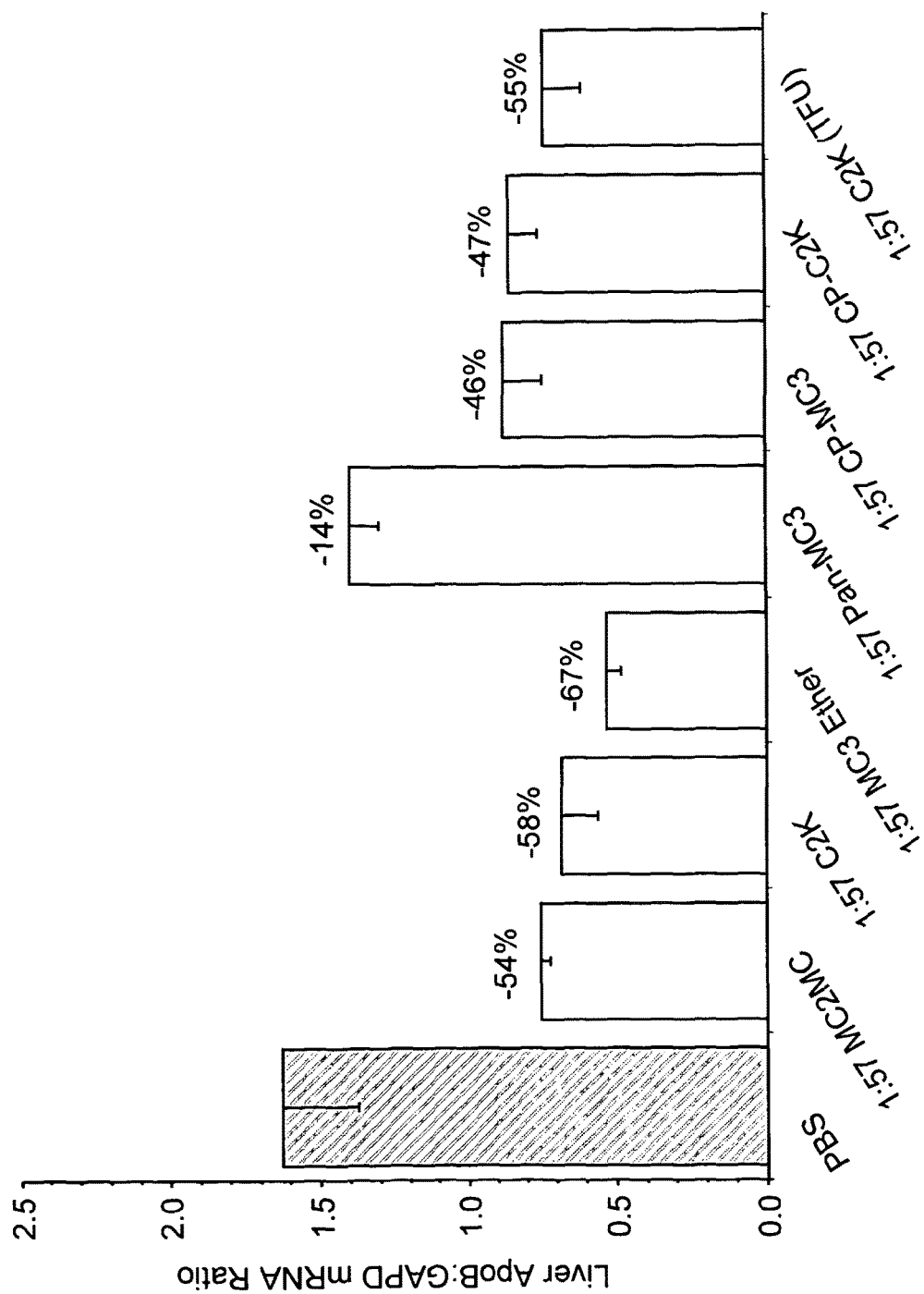
FIG. 7 shows a comparison of the liver ApoB mRNA knockdown activity of additional exemplary SNALP formulations containing cationic lipids of Formulas II-III.

FIG. 7 shows a comparison of the liver ApoB mRNA knockdown activity of each of these SNALP formulations (Error bars=SD). In particular, FIG. 7 shows that a SNALP formulation containing either CP-MC3 or CP-C2K displayed similar ApoB silencing activity compared to a SNALP formulation containing the C2K benchmark cationic lipid. Notably, SNALP formulations containing the novel cyclic cationic lipids of Formula II-III displayed improved stability over SNALP formulations containing their polyunsaturated counterparts when evaluated under various different storage conditions using techniques such as, e.g., analysis of any change in particle size over time and/or determination of any degradation of the nucleic acid payload and/or cationic lipid.

It is to be understood that the above description is intended to be illustrative and not restrictive. Many embodiments will be apparent to those of skill in the art upon reading the above description. The scope of the invention should, therefore, be determined not with reference to the above description, but should instead be determined with reference to the appended claims, along with the full scope of equivalents to which such claims are entitled. The disclosures of all articles and references, including patent applications, patents, PCT publications, and Genbank Accession Nos., are incorporated herein by reference for all purposes.

What is claimed is:

1. A cationic lipid of Formula III having the following structure:

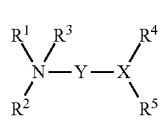

(III)

or salts thereof, wherein:

$R^1$ and $R^2$ are either the same or different and are independently hydrogen (H) or an optionally substituted $C_1$-$C_6$ alkyl, $C_2$-$C_6$ alkenyl, or $C_2$-$C_6$ alkynyl, or $R^1$ and $R^2$ may join to form an optionally substituted heterocyclic ring;

$R^3$ is either absent or is hydrogen (H) or a $C_1$-$C_6$ alkyl to provide a quaternary amine;

$R^4$ and $R^5$ are either the same or different and are independently an optionally substituted $C_{10}$-$C_{24}$ alkyl, $C_{10}$-$C_{24}$ alkenyl, $C_{10}$-$C_{24}$ alkynyl, or $C_{10}$-$C_{24}$ acyl, wherein at least one of $R^4$ and $R^5$ comprises at least one optionally substituted cyclic alkyl group;

X is O, S, N($R^6$), C(O), C(O)O, OC(O), C(O)N($R^6$), N($R^6$)C(O), OC(O)N($R^6$), C(O)O, C(O)S, C(S)O, S(O), S(O)(O), C(S), or an optionally substituted heterocyclic ring, wherein $R^6$ is hydrogen (H) or an optionally substituted $C_1$-$C_{10}$ alkyl, $C_2$-$C_{10}$ alkenyl, or $C_2$-$C_{10}$ alkynyl; and Y is either absent or is an optionally substituted $C_1$-$C_6$ alkyl, $C_2$-$C_6$ alkenyl, or $C_2$-$C_6$ alkynyl.

2. The cationic lipid of claim 1, wherein $R^1$ and $R^2$ are independently selected from the group consisting of a methyl group and an ethyl group.

3. The cationic lipid of claim 1, wherein X is C(O)O or O.

4. The cationic lipid of claim 1, wherein Y is $(CH_2)_n$ and n is 0, 1, 2, 3, 4, 5, or 6.

5. The cationic lipid of claim 4, wherein n is 2, 3, or 4.

6. The cationic lipid of claim 1, wherein the at least one optionally substituted cyclic alkyl group comprises an optionally substituted saturated cyclic alkyl group, an optionally substituted unsaturated cyclic alkyl group, or a combination thereof.

7. The cationic lipid of claim 6, wherein the optionally substituted saturated cyclic alkyl group comprises an optionally substituted $C_{3-8}$ cycloalkyl group.

8. The cationic lipid of claim 6, wherein the optionally substituted saturated cyclic alkyl group comprises a cyclopropyl group.

9. The cationic lipid of claim 6, wherein the optionally substituted unsaturated cyclic alkyl group comprises an optionally substituted $C_{3-8}$ cycloalkenyl group.

10. The cationic lipid of claim 1, wherein $R^4$ and $R^5$ both independently comprise at least one, two, or three optionally substituted cyclic alkyl groups.

11. The cationic lipid of claim 1, wherein $R^4$ and $R^5$ are both $C_{12}$-$C_{20}$ alkyl groups having at least one, two, or three optionally substituted cyclic alkyl groups.

12. The cationic lipid of claim 1, wherein $R^4$ and $R^5$ are both $C_{18}$ alkyl groups having at least one, two, or three optionally substituted cyclic alkyl groups.

13. The cationic lipid of claim 10, wherein the at least one, two, or three optionally substituted cyclic alkyl groups comprise cyclopropyl groups.

14. The cationic lipid of claim 1, wherein $R^4$ and $R^5$ both comprise the same number of optionally substituted cyclic alkyl groups.

15. The cationic lipid of claim 1, wherein $R^4$ and $R^5$ both comprise the same type(s) of optionally substituted cyclic alkyl groups.

16. A cationic lipid having a structure selected from the group consisting of:

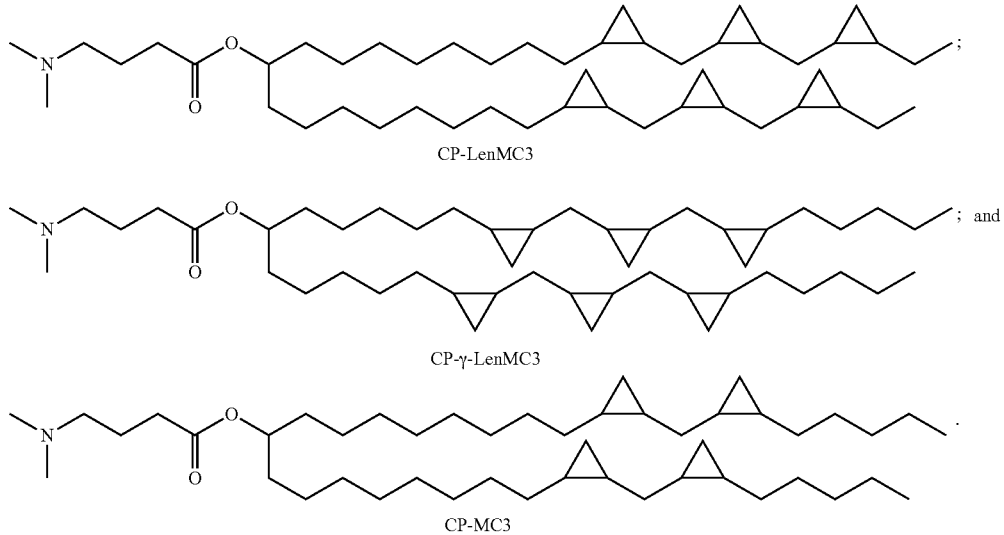

17. A lipid particle comprising a cationic lipid of claim 1.

18. The lipid particle of claim 17, wherein the particle further comprises a non-cationic lipid.

19. The lipid particle of claim 18, wherein the non-cationic lipid is selected from the group consisting of a phospholipid, cholesterol, or a mixture of a phospholipid and cholesterol.

20. The lipid particle of claim 17, wherein the particle further comprises a conjugated lipid that inhibits aggregation of particles.

21. The lipid particle of claim 20, wherein the conjugated lipid that inhibits aggregation of particles comprises a polyethyleneglycol (PEG)-lipid conjugate.

22. The lipid particle of claim 21, wherein the PEG-lipid conjugate comprises a PEG-diacylglycerol (PEG-DAG) conjugate, a PEG-dialkyloxypropyl (PEG-DAA) conjugate, or a mixture thereof.

23. The lipid particle of claim 17, wherein the particle further comprises a therapeutic agent.

24. The lipid particle of claim 23, wherein the therapeutic agent is a nucleic acid.

25. The lipid particle of claim 24, wherein the nucleic acid is an interfering RNA.

26. The lipid particle of claim 25, wherein the interfering RNA is an siRNA.

27. A pharmaceutical composition comprising a lipid particle of claim 17 and a pharmaceutically acceptable carrier.

28. A method for introducing a therapeutic agent into a mammalian cell, the method comprising:
contacting the cell with a lipid particle of claim 23.

29. A method for the in vivo delivery of a therapeutic agent, the method comprising:
administering to a mammal a lipid particle of claim 23.

30. The cationic lipid of claim 3, wherein X is C(O)O.

* * * * *